United States Patent
Kamiya et al.

(10) Patent No.: US 7,429,612 B2
(45) Date of Patent: Sep. 30, 2008

(54) INDOLINE COMPOUND AND MEDICINAL USE THEREOF

(75) Inventors: Shouji Kamiya, Kyoto (JP); Miho Ikai, Kyoto (JP); Kenji Takahash, Kyoto (JP); Tadatsugu Tarumi, Kyoto (JP); Masayasu Kasai, Kyoto (JP); Akihisa Yoshimi, Kyoto (JP); Hiroaki Shirahase, Kyoto (JP)

(73) Assignee: Kyoto Pharmaceutical Industries, Ltd., Kyoto (JP)

( * ) Notice: Subject to any disclaimer, the term of this patent is extended or adjusted under 35 U.S.C. 154(b) by 469 days.

(21) Appl. No.: 10/521,175

(22) PCT Filed: Jul. 16, 2003

(86) PCT No.: PCT/JP03/09012

§ 371 (c)(1),
(2), (4) Date: Mar. 14, 2005

(87) PCT Pub. No.: WO2004/007450

PCT Pub. Date: Jan. 22, 2004

(65) Prior Publication Data

US 2006/0128787 A1    Jun. 15, 2006

(30) Foreign Application Priority Data

Jul. 17, 2002    (JP) ............... 2002-208878

(51) Int. Cl.
*A61K 31/404*    (2006.01)
*C07D 209/04*    (2006.01)
(52) U.S. Cl. ............ 514/419; 548/469; 548/490; 548/491; 514/415
(58) Field of Classification Search ........... 548/469, 548/490, 491; 519/415, 419
See application file for complete search history.

(56) References Cited

U.S. PATENT DOCUMENTS

| | | | |
|---|---|---|---|
| 4,013,404 A * | 3/1977 | Parent et al. ............... 8/423 |
| 4,435,406 A * | 3/1984 | Krasso et al. ............... 514/338 |
| 4,599,347 A * | 7/1986 | Krasso et al. ............... 514/338 |
| 4,803,218 A | 2/1989 | Stanley et al. |
| 4,956,372 A | 9/1990 | Kojima et al. |
| 5,091,419 A | 2/1992 | Ito et al. |
| 5,143,919 A | 9/1992 | Meguro et al. |
| 5,153,226 A | 10/1992 | Chucholowski et al. |
| 5,166,429 A | 11/1992 | Ito et al. |
| 5,219,859 A | 6/1993 | Festal et al. |
| 5,227,492 A | 7/1993 | Ito et al. |
| 5,254,565 A | 10/1993 | Meguro et al. |
| 5,254,590 A | 10/1993 | Malen et al. |
| 5,256,782 A | 10/1993 | Meguro et al. |
| 5,258,405 A | 11/1993 | Ito et al. |
| 5,384,425 A | 1/1995 | Ito et al. |
| 5,420,348 A | 5/1995 | Ito et al. |
| 5,767,129 A | 6/1998 | Yuen |
| 5,990,150 A | 11/1999 | Matsui et al. |
| 5,994,040 A | 11/1999 | Morishima et al. |
| 6,063,806 A | 5/2000 | Kamiya et al. |
| 6,127,403 A * | 10/2000 | Matsui et al. ............... 514/414 |
| 6,169,107 B1 | 1/2001 | Kitano et al. |
| 6,200,988 B1 | 3/2001 | Kamiya et al. |
| 6,248,772 B1 | 6/2001 | Kitano et al. |
| 6,414,012 B1 | 7/2002 | Matsui et al. |
| 6,489,475 B2 | 12/2002 | Matsui et al. |

FOREIGN PATENT DOCUMENTS

| | | |
|---|---|---|
| EP | 0 512 570 | 11/1992 |
| EP | 0 622 356 | 11/1994 |
| EP | 0 708 091 | 4/1996 |
| EP | 0 782 986 | 7/1997 |
| EP | 0 793 140 | 9/1997 |
| JP | 2-117651 | 5/1990 |
| JP | 3-7259 | 1/1991 |
| JP | 3-148247 | 6/1991 |
| JP | 4-66568 | 3/1992 |
| JP | 4-234839 | 8/1992 |
| JP | 4-327564 | 11/1992 |
| JP | 5-32666 | 2/1993 |
| JP | 5-97802 | 4/1993 |
| JP | 5-140102 | 6/1993 |

(Continued)

OTHER PUBLICATIONS

V. DeVries et al., "Potential Antiatherosclerotic Agents .5.[1] An Acyl-CoA:Cholesterol O-Acyltransferase Inhibitor with Hypocholesterolemic Activity", J. Med. Chem., vol. 29, 1986, pp. 1131-1133.

(Continued)

*Primary Examiner*—Golam M Shameem
(74) *Attorney, Agent, or Firm*—Wenderoth, Lind & Ponack, LLP

(57) ABSTRACT

The present invention provides an indoline compound represented by the formula (I)

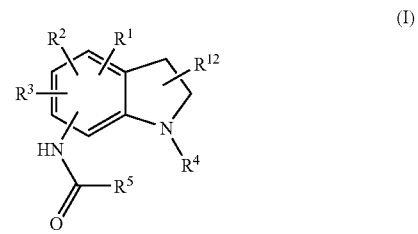

(I)

wherein each symbol is as defined in the DESCRIPTION, or a pharmaceutically acceptable salt thereof, and a pharmaceutical composition containing this indoline compound or a pharmaceutically acceptable salt thereof. The compound of the present invention shows superior ACAT inhibitory effect and superior lipoperoxidation inhibitory effect and is useful as an ACAT inhibitor or a lipoperoxidation inhibitor.

34 Claims, No Drawings

FOREIGN PATENT DOCUMENTS

| | | |
|---|---|---|
| JP | 8-92210 | 4/1996 |
| JP | 8-208602 | 8/1996 |
| JP | 2002-47269 | 2/2002 |
| JP | 2002-302481 | 10/2002 |
| WO | 96/09287 | 3/1996 |
| WO | 97/12860 | 4/1997 |
| WO | 2004/096767 | 11/2004 |

OTHER PUBLICATIONS

Fredrick J. Brown et al., "Evolution of a Series of Peptidoleukotriene Antagonists: Synthesis and Structure-Activity Relationships of 1,6-Disubstituted Indoles and Indazoles", J. Med. Chem., vol. 33 (6), 1990 pp. 1771-1781.

Victor G. Matassa et al., "Evolution of a Series of Peptidoleukotriene Antagonists: Synthesis and Structure/Activity Relationships of 1,3,5-Substituted Indoles and Indazoles", J. Med. Chem., vol. 33(6), 1990, pp. 1781-1790.

K. Yee et al., "Novel Series of Selective Leukotriene Antagonists: Exploration and Timization of the Acidic Region in 1,6-Disubstituted Indoles and Indazoles[1]", J. Med. Chem., vol. 33(9) 1990, pp. 2437-2451.

US 6,204,392, 03/2001, Matsui et al. (withdrawn)

* cited by examiner

INDOLINE COMPOUND AND MEDICINAL USE THEREOF

This application is a U.S. national stage of International Application No. PCT/JP03/09012 filed Jul. 16, 2003.

1. Technical Field

The present invention relates to a novel indoline compound and pharmaceutical use thereof. More particularly, the present invention relates to a novel indoline compound having an inhibitory activity on acyl-CoA: cholesterol acyltransferase (hereinafter ACAT) and lipoperoxidation inhibitory activity, or to pharmaceutical use thereof.

2. Background Art

It is a well-known fact that arteriosclerosis is an extremely important factor causing various circulatory diseases, and active studies have been undertaken in an attempt to achieve suppression of the evolution of arteriosclerosis or regression thereof.

In recent years, it has been clarified that cholesterol in blood is accumulated in arterial walls as a cholesterol ester, and that it significantly evolves arteriosclerosis. Therefore, a decrease in cholesterol level in blood leads to the reduction of accumulation of cholesterol ester in arterial walls, and is effective for the suppression of evolution of arteriosclerosis and regression thereof. As a pharmaceutical agent that decreases cholesterol in blood, a cholesterol synthesis inhibitor, a bile acid absorption inhibitor and the like are used and their effectiveness has been acknowledged. However, an ideal pharmaceutical agent that shows clear clinical effect and less side effects has not been realized yet.

Cholesterol in food is esterified in mucous membrane of small intestine, and taken into blood as chylomicron. ACAT is known to play an important role in the generation of cholesterol ester in mucous membrane of small intestine. In addition, cholesterol synthesized in the liver is esterified by ACAT and secreted into blood as a very low density lipoprotein (VLDL). Accordingly, suppression of esterification of cholesterol by inhibition of ACAT in the mucosal membrane of the small intestine and liver is considered to decrease cholesterol level of blood.

A pharmaceutical agent which more directly inhibits deposition of cholesterol in arterial walls has been desired as a pharmaceutical agent which more effectively prevents or treats arteriosclerosis, and studies in this field are thriving. Yet, an ideal pharmaceutical agent has not been developed. In arterial walls, ACAT in macrophages or smooth muscle cells esterifies cholesterol and causes accumulation of cholesterol ester. Therefore, inhibition of ACAT in arterial walls is expected to effectively suppress accumulation of cholesterol ester.

From the foregoing, it is concluded that an ACAT inhibitor will make an effective pharmaceutical agent for hyperlipemia and arteriosclerosis, as a result of suppression of absorption of cholesterol in small intestine, secretion of cholesterol from liver and accumulation of cholesterol in arterial walls.

Conventionally, there have been reported, for example, as such ACAT inhibitors, amide and urea derivatives [J. Med. Chem., 29: 1131(1986), Japanese Patent Unexamined Publication Nos. 117651/1990, 7259/1991, 234839/1992, 327564/1992 and 32666/1993]. However, creation and pharmacological studies of these compounds have been far from sufficient. First of all, in these compounds, it is not clear if the blood cholesterol lowering action and cholesterol accumulation suppressing effect in arterial wall due to an ACAT inhibitory effect is clinically sufficiently effective for the suppression of evolution of arteriosclerosis and regression thereof. Since most of the conventional ACAT inhibitors are extremely highly fat-soluble, oral absorption is often low, and when oral absorption is fine, organopathy in adrenal, liver and the like is feared to be induced. Furthermore, a highly fat-soluble, low absorptive ACAT inhibitor may clinically cause diarrhea.

Meanwhile, hyperoxidation of low density lipoprotein (LDL) is also highly responsible for intracellular incorporation of cholesterol accumulated as cholesterol ester in arterial walls.

In addition, it is known that hyperoxidation of lipids in a living organism is deeply concerned with the onset of arteriosclerosis and cerebrovascular and cardiovascular ischemic diseases.

Accordingly, a compound having both an ACAT inhibitory activity and lipoperoxidation inhibitory activity is highly useful as a pharmaceutical product, since it effectively and certainly reduces accumulation of cholesterol ester in arterial walls and inhibits lipoperoxidation in living organisms, thereby preventing and treating various vascular diseases caused thereby.

It is therefore an object of the present invention to provide a compound having ACAT inhibitory activity and lipoperoxidation inhibitory activity, as well as pharmaceutical use thereof, particularly ACAT inhibitor and lipoperoxidation inhibitor.

DISCLOSURE OF THE INVENTION

The present inventors have conducted intensive studies in an attempt to achieve the aforementioned objects and found that the novel indoline compound of the present invention not only has a strong ACAT inhibitory effect but also a lipoperoxidation inhibitory effect, superior oral absorbability, and a strong anti-hyperlipidemia effect and an anti-arteriosclerosis effect, which resulted in the completion of the present invention.

Accordingly, the present invention provides 1) a novel indoline compound represented by the formula (I)

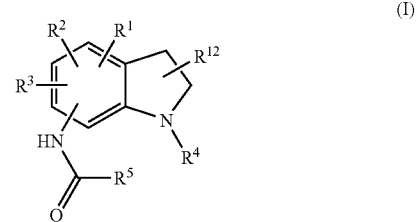

wherein $R^1$ and $R^3$ are the same or different and each is hydrogen atom, lower alkyl group or lower alkoxy group, $R^2$ is $-NO_2$, $-NHSO_2R^6$ [$R^6$ is alkyl group, aryl group or $-NHR^7$ ($R^7$ is hydrogen atom, $-COR^{13}$ ($R^{13}$ is hydrogen atom or lower alkyl group) or lower alkoxycarbonyl group)], $-NHCONH_2$ or lower alkyl group substituted by $-NHSO_2R^6$ [$R^6$ is alkyl group, aryl group or $-NHR^7$ ($R^7$ is hydrogen atom, $-COR^{13}$ ($R^{13}$ is hydrogen atom or lower alkyl group) or lower alkoxycarbonyl group)], $R^4$ is hydrogen atom, alkyl group optionally substituted by hydroxy group, $-COR^{13}$ ($R^{13}$ is hydrogen atom or lower alkyl group), lower alkenyl group, lower alkoxy lower alkyl group, lower alkylthio lower alkyl group, cycloalkyl group or cycloalkylalkyl group, $R^5$ is alkyl group, cycloalkyl group or aryl group, $R^{12}$ is hydrogen atom, lower alkyl group, lower alkoxy lower alkyl group or lower alkylthio lower alkyl group, or a pharmaceutically acceptable salt thereof, 2) the novel indoline compound of the above-mentioned 1), wherein, in the formula (I), $R^1$ and $R^3$ are the same or different and each is hydrogen atom, lower alkyl group or lower alkoxy group, $R^2$ is —$NO_2$, —$NHSO_2R^6$ [$R^6$ is alkyl group, aryl group or —$NHR^7$ ($R^7$ is hydrogen atom, —$COR^{13}$ ($R^{13}$ is hydrogen atom or lower alkyl group) or lower alkoxycarbonyl group)], —$NHCONH_2$ or lower alkyl group substituted by —$NHSO_2R^6$ [$R^6$ is alkyl group, aryl group or —$NHR^7$ ($R^7$ is hydrogen atom, —$COR^{13}$ ($R^{13}$ is hydrogen atom or lower alkyl group) or lower alkoxycarbonyl group)], $R^4$ is hydrogen atom, alkyl group, cycloalkyl group or cycloalkylalkyl group, $R^5$ is alkyl group, cycloalkyl group or aryl group, and $R^{12}$ is hydrogen atom, or a pharmaceutically acceptable salt thereof, 3) the novel indoline compound of the above-mentioned 1), wherein, in the formula (I), $R^2$ is —$NHSO_2R^6$ [$R^6$ is alkyl group or —$NHR^7$ ($R^7$ is hydrogen atom)], $R^4$ is alkyl group optionally substituted by hydroxy group, —$COR^{13}$ ($R^{13}$ is hydrogen atom or lower alkyl group), lower alkenyl group, lower alkoxy lower alkyl group or lower alkylthio lower alkyl group, $R^5$ is alkyl group, $R^{12}$ is hydrogen atom, lower alkyl group, lower alkoxy lower alkyl group or lower alkylthio lower alkyl group, or a pharmaceutically acceptable salt thereof, 4) the novel indoline compound of the above-mentioned 2), wherein, in the formula (I), $R^2$ is —$NHSO_2R^6$ [$R^6$ is alkyl group or —$NHR^7$ ($R^7$ is hydrogen atom)] or —$NHCONH_2$, or a pharmaceutically acceptable salt thereof, 5) the novel indoline compound of the above-mentioned 2), wherein, in the formula (I), $R^2$ or —$NHCOR^5$ is bonded to the 5-position of indoline, and the other is bonded to the 7-position of indoline, or a pharmaceutically acceptable salt thereof, 6) the novel indoline compound of the above-mentioned 3), wherein, in the formula (I), $R^2$ is bonded to the 5-position of indoline, and —$NHCOR^5$ is bonded to the 7-position of indoline, or a pharmaceutically acceptable salt thereof, 7) the novel indoline compound of the above-mentioned 4), wherein, in the formula (I), $R^2$ is bonded to the 5-position of indoline, and —$NHCOR^5$ is bonded to the 7-position of indoline, or a pharmaceutically acceptable salt thereof, 8) the novel indoline compound of the above-mentioned 6), wherein, in the formula (I), $R^4$ is lower alkoxy lower alkyl group or lower alkylthio lower alkyl group, and R is hydrogen atom or lower alkyl group, or a pharmaceutically acceptable salt thereof, 9) the novel indoline compound of the above-mentioned 8), wherein, in the formula (I), $R^1$ and $R^3$ are lower alkyl groups, or a pharmaceutically acceptable salt thereof, 10) the novel indoline compound of the above-mentioned 6), wherein, in the formula (I), $R^{12}$ is bonded to the 2-position of indoline, or a pharmaceutically acceptable salt thereof, 11) the novel indoline compound of the above-mentioned 10), wherein, in the formula (I), $R^4$ is alkyl group, $R^{12}$ is lower alkoxy lower alkyl group or lower alkylthio lower alkyl group, or a pharmaceutically acceptable salt thereof, 12) the novel indoline compound of the above-mentioned 11), wherein, in the formula (I), $R^3$ and $R^3$ are lower alkyl groups, or a pharmaceutically acceptable salt thereof, 13) the novel indoline compound of the above-mentioned 7), wherein, in the formula (I), $R^1$ and $R^3$ are lower alkyl groups, and $R^5$ is alkyl group, or a pharmaceutically acceptable salt thereof, 14) the novel indoline compound of the above-mentioned 13), wherein, in the formula (I), $R^2$ is —$NHSO_2R^6$ ($R^6$ is alkyl group), or a pharmaceutically acceptable salt thereof, 15) the novel indoline compound of the above-mentioned 13), wherein, in the formula (I), $R^2$ is —$NHSO_2R^6$ [$R^6$ is —$NHR^7$ ($R^7$ is hydrogen atom)], or a pharmaceutically acceptable salt thereof, 16) the novel indoline compound of the above-mentioned 13), wherein, in the formula (I), $R^2$ is —$NHCONH_2$, or a pharmaceutically acceptable salt thereof, 17) the novel indoline compound of the above-mentioned 2), wherein the compound of the formula (I) is any of the following (1)-(5), or a pharmaceutically acceptable salt thereof:

(1) N-(5-methanesulfonylamino-4,6-dimethyl-1-propylindolin-7-yl)-2,2-dimethylpropanamide, (2) N-[5-methanesulfonylamino-4,6-dimethyl-1-(2-methylpropyl)indolin-7-yl]-2,2-dimethylpropanamide, (3) N-(1-butyl-5-methanesulfonylamino-4,6-dimethylindolin-7-yl)-2,2-dimethylpropanamide, (4) N-[5-methanesulfonylamino-4,6-dimethyl-1-(3-methylbutyl)indolin-7-yl]-2,2-dimethylpropanamide, (5) N-(5-methanesulfonylamino-4,6-dimethyl-1-pentylindolin-7-yl)-2,2-dimethylpropanamide, 18) the novel indoline compound of the above-mentioned 2), wherein the compound of the formula (I) is the following (1) or, (2), or a pharmaceutically acceptable salt thereof:

(1) N-(5-methanesulfonylamino-4,6-dimethyl-1-octylindolin-7-yl)-2,2-dimethylpropanamide, (2) N-(1-hexyl-5-methanesulfonylamino-4,6-dimethylindolin-7-yl)-2,2-dimethylpropanamide, 19) the novel indoline compound of the above-mentioned 2), wherein the compound of the formula (I) is the following (1) or (2), or a pharmaceutically acceptable salt thereof:

(1) N-(1-ethyl-5-methanesulfonylamino-4,6-dimethylindolin-7-yl)-2,2-dimethylpropanamide, (2) N-(5-methanesulfonylamino-1,4,6-trimethylindolin-7-yl)-2,2-dimethylpropanamide, 20) the novel indoline compound of the above-mentioned 2), wherein the compound of the formula (I) is any of the following (1)-(6), or a pharmaceutically acceptable salt thereof:

(1) N-(4,6-dimethyl-1-octyl-5-sulfamoylaminoindolin-7-yl)-2,2-dimethylpropanamide, (2) N-(4,6-dimethyl-1-propyl-5-sulfamoylaminoindolin-7-yl)-2,2-dimethylpropanamide, (3) N-(4,6-dimethyl-1-pentyl-5-sulfamoylaminoindolin-7-yl)-2,2-dimethylpropanamide, (4) N-[4,6-dimethyl-1-(2-methylpropyl)-5-sulfamoylaminoindolin-7-yl]-2,2-dimethylpropanamide, (5) N-(1-butyl-4,6-dimethyl-5-sulfamoylaminoindolin-7-yl)-2,2-dimethylpropanamide, (6) N-[4,6-dimethyl-1-(3-methylbutyl)-5-sulfamoylaminoindolin-7-yl]-2,2-dimethylpropanamide, 21) the novel indoline compound of the above-mentioned 2), wherein the compound of the formula (I) is any of the following (1)-(7), or a pharmaceutically acceptable salt thereof:

(1) N-(7-methanesulfonylamino-1,4,6-trimethylindolin-5-yl)-2,2-dimethylundecanamide, (2) N-(7-methanesulfonylamino-4,6-dimethylindolin-5-yl)-2,2-dimethylundecanamide, (3) N-[7-(2-propanesulfonylamino)-4,6-dimethylindolin-5-yl]-2,2-dimethylundecanamide, (4) N-[7-(2-propanesulfonylamino)-4,6-dimethylindolin-5-yl]-2,2-dimethyloctanamide, (5) N-[4,6-dimethyl-7-(p-toluene)sulfonylaminoindolin-5-yl]-2,2-dimethylundecanamide,
(6) N-(4,6-dimethyl-7-sulfamoylaminoindolin-5-yl)-2,2-dimethylundecanamide,
(7) N-(4,6-dimethyl-7-ureidoindolin-5-yl)-2,2-dimethylundecanamide, 22) the novel indoline compound of the above-mentioned 2), wherein the compound of the formula (I) is any of the following (1)-(5), or a pharmaceutically acceptable salt thereof:
(1) N-(4,6-dimethyl-5-nitro-1-octylindolin-7-yl)-2,2-dimethylpropanamide,
(2) N-(5-methanesulfonylaminomethyl-4,6-dimethyl-1-octylindolin-7-yl)-2,2-dimethylpropanamide,
(3) N-(4,6-dimethyl-1-octyl-5-ureidoindolin-7-yl)-2,2-dimethylpropanamide,
(4) N-[5-(N-acetylsulfamoylamino)-4,6-dimethyl-1-octylindolin-7-yl]-2,2-dimethylpropanamide,
(5) N-[5-(N-methoxycarbonylsulfamoylamino)-4,6-dimethyl-1-octylindolin-7-yl]-2,2-dimethylpropanamide, 23) the novel indoline compound of the above-mentioned 9) or 12), wherein, in the formula (I), $R^2$ is —$NHSO_2R^6$ ($R^6$ is alkyl group), or a pharmaceutically acceptable salt thereof, 24) the novel indoline compound of the above-mentioned 9) or 12), wherein, in the formula (I), $R^2$ is —$NHSO_2R^6$ [$R^6$ is —$NHR^7$ ($R^7$ is hydrogen atom)], or a pharmaceutically acceptable salt thereof, 25) the novel indoline compound of the above-mentioned 2), wherein the compound of the formula (I) is any-of the following (1)-(6), or a pharmaceutically acceptable salt thereof:
(1) N-(1-isopropyl-5-methanesulfonylamino-4,6-dimethylindoline 7-yl)-2,2-dimethylpropanamide,
(2) N-[1-(2,2-dimethylpropyl)-5-methanesulfonylamino-4,6-dimethylindolin-7-yl]-2,2-dimethylpropanamide,
(3) N-(1-cyclobutylmethyl-5-methanesulfonylamino-4,6-dimethylindolin-7-yl)-2,2-dimethylpropanamide,
(4) N-(1-cyclopentyl-5-methanesulfonylamino-4,6-dimethylindolin-7-yl)-2,2-dimethylpropanamide,
(5) N-(1-cyclopentyl-4,6-dimethyl-5-sulfamoylaminoindolin-7-yl)-2,2-dimethylpropanamide,
(6) N-(1-cyclopropylmethyl-5-methanesulfonylamino-4,6-dimethylindolin-7-yl)-2,2-dimethylpropanamide, 26) the novel indoline compound of the above-mentioned 3), wherein the compound of the formula (I) is N-[5-methanesulfonylamino-4,6-dimethyl-1-(3-methyl-2-butenyl)indolin-7-yl]-2,2-dimethylpropanamide, or a pharmaceutically acceptable salt thereof, 27) the novel indoline compound of the above-mentioned 3), wherein the compound of the formula (I) any of the following (1)-(6), or a pharmaceutically acceptable salt thereof:
(1) N-[1-(2-ethoxyethyl)-4,6-dimethyl-5-sulfamoylaminoindolin-7-yl]-2,2-dimethylpropanamide,
(2) N-[1-(2-ethoxyethyl)-2,4,6-trimethyl-5-sulfamoylaminoindolin-7-yl]-2,2-dimethylpropanamide,
(3) N-[1-(2-methoxyethyl)-4,6-dimethyl-5-sulfamoylaminoindolin-7-yl]-2,2-dimethylpropanamide,
(4) N-[1-(2-methoxyethyl)-2,4,6-trimethyl-5-sulfamoylaminoindolin-7-yl]-2,2-dimethylpropanamide,
(5) N-[1-(2-ethylthioethyl)-4,6-dimethyl-5-sulfamoylaminoindolin-7-yl]-2,2-dimethylpropanamide hydrochloride,
(6) N-[4,6-dimethyl-1-(2-methylthioethyl)-5-sulfamoylaminoindolin-7-yl]-2,2-dimethylpropanamide hydrochloride, 28) the novel indoline compound of the above-mentioned 3), wherein the compound of the formula (I) is any of the following (1)-(4), or a pharmaceutically acceptable salt thereof:
(1) N-(2-methoxymethyl-4,6-dimethyl-1-propyl-5-sulfamoylaminoindolin-7-yl)-2,2-dimethylpropanamide,
(2) N-(2-ethoxymethyl-4,6-dimethyl-1-propyl-5-sulfamoylaminoindolin-7-yl)-2,2-dimethylpropanamide,
(3) N-(2-methylthiomethyl-4,6-dimethyl-1-propyl-5-sulfamoylaminoindolin-7-yl)-2,2-dimethylpropanamide,
(4) N-(2-ethylthiomethyl-4,6-dimethyl-1-propyl-5-sulfamoylaminoindolin-7-yl)-2,2-dimethylpropanamide, 29) the novel indoline compound of the above-mentioned 3), wherein the compound of the formula (I) is the following (1) or (2), or a pharmaceutically acceptable salt thereof:
(1) N-[1-(2-ethoxyethyl)-5-methanesulfonylamino-4,6-dimethylindolin-7-yl]-2,2-dimethylpropanamide,
(2) N-[1-(2-methoxyethyl)-5-methanesulfonylamino-4,6-dimethylindolin-7-yl]-2,2-dimethylpropanamide, 30) a pharmaceutical composition comprising a novel indoline compound of any of the above-mentioned 1)-29), or a pharmaceutically acceptable salt thereof, 31) an acyl-coenzyme A: cholesterol acyl transferase inhibitor comprising a novel indoline compound of any of the above-mentioned 1)-29), or a pharmaceutically acceptable salt thereof, 32) a lipoperoxidation inhibitor comprising a novel indoline compound of any of the above-mentioned 1)-29), or a pharmaceutically acceptable salt thereof, and the like.

MODE OF EMBODIMENTS OF THE INVENTION

Each symbol used in the present specification is explained in the following.

The lower alkyl group for $R^1$, $R^2$ or $R^{13}$ preferably has 1 to 6 carbon atoms and may be linear or branched chain. For example, methyl, ethyl, propyl, isopropyl, butyl, isobutyl, sec-butyl, tert-butyl, pentyl, isopentyl, neopentyl, hexyl and the like can be mentioned.

The lower alkoxy group for $R^1$ or $R^3$ preferably has 1 to 6 carbon atoms and may be linear or branched chain. For example, methoxy, ethoxy, propoxy, isopropoxy, butoxy, isobutoxy, sec-butoxy, tert-butoxy, pentyloxy, isopentyloxy, neopentyloxy, hexyloxy and the like can be mentioned.

The lower alkyl group of the lower alkyl group substituted by —$NHSO_2R^6$ for $R^2$ preferably has 1 to 6 carbon atoms and may be linear or branched chain. For example, methyl, ethyl, propyl, butyl, pentyl, hexyl, 1-methylethyl, 1,1-dimethylethyl, 2,2-dimethylpropyl and the like can be mentioned. The lower alkyl group is substituted by one —$NHSO_2R^6$ at a substitutable position.

The alkyl group of the alkyl group optionally substituted by hydroxy group for $R^4$ preferably has 1 to 20 carbon atoms, and may be linear or branched chain. For example, methyl, ethyl, propyl, isopropyl, butyl, isobutyl, sec-butyl, tert-butyl, pentyl, isopentyl, neopentylhexyl, heptyl, octyl, nonyl, decyl, undecyl, dodecyl, tridecyl, tetradecyl, pentadecyl, hexadecyl, heptadecyl, nonadecyl, icosyl, 1,1-dimethylpropyl, 1,1-dimethylbutyl, 1,1-dimethylhexyl, 1,1-dimethylheptyl, 3,3-dimethylbutyl, 4,4-dimethylpentyl and the like can be mentioned. The lower alkyl group is substituted by one or two hydroxy groups at substitutable positions.

The lower alkenyl group for $R^4$ preferably has 3 to 6 carbon atoms and may be linear or branched chain. For example, 2-propenyl, 2-butenyl, 3-butenyl, 2-pentenyl, 3-pentenyl, 4-pentenyl, 2-hexenyl, 3-hexenyl, 3-methyl-2-butenyl and the like can be mentioned.

As for the lower alkoxy lower alkyl group for $R^4$ or $R^{12}$, its lower alkoxy moiety preferably has 1 to 6 carbon atoms, and may be linear or branched chain. As the lower alkyl moiety, the lower alkyl group described above can be mentioned. For example, methoxymethyl, methoxyethyl, methoxypropyl, methoxybutyl, methoxypentyl, methoxyhexyl, ethoxymethyl, ethoxyethyl, ethoxypropyl, ethoxybutyl, propoxymethyl, propoxyethyl, isopropoxymethyl, isopropoxyethyl, butoxymethyl, butoxyethyl and the like can be mentioned.

As for the lower alkylthio lower alkyl group for $R^4$ or $R^{12}$, its alkyl moiety of the lower alkylthio moiety preferably has 1 to 6 carbon atoms, and may be linear or branched chain. As the lower alkyl moiety, the lower alkyl group described above can be mentioned. For example, methylthiomethyl, methylthioethyl, methylthiopropyl, methylthiobutyl, ethylthioethyl, ethylthiopropyl, propylthiomethyl, propylthioethyl, isopropylthiomethyl, isopropylthioethyl, butylthiomethyl, butylthioethyl, tert-butylthiomethyl, tert-butylthioethyl, pentylthiomethyl, pentylthioethyl, hexylthiomethyl and the like can be mentioned.

The cycloalkyl group for $R^4$ or $R^5$ preferably has 3 to 8 carbon atoms. For example, cyclopropyl, cyclobutyl, cyclopentyl, cyclohexyl, cycloheptyl, cyclooctyl and the like can be mentioned.

As for the cycloalkylalkyl group for $R^4$, its cycloalkyl moiety preferably has 3 to 8 carbon atoms, and the alkyl moiety preferably has 1 to 3 carbon atoms. For example, cyclopropylmethyl, cyclobutylmethyl, cyclopentylmethyl, cyclohexylmethyl, cyclopropylethyl, cyclopropylpropyl, cycloheptylmethyl, cyclooctylmethyl and the like can be mentioned.

The alkyl group for $R^5$ or $R^6$ preferably has 1 to 20 carbon atoms, and may be linear or branched chain. For example, methyl, ethyl, propyl, isopropyl, butyl, isobutyl, sec-butyl, tert-butyl, pentyl, isopentyl, neopentylhexyl, heptyl, octyl, nonyl, decyl, undecyl, dodecyl, tridecyl, tetradecyl, pentadecyl, hexadecyl, heptadecyl, nonadecyl, icosyl, 1,1-dimethylpropyl, 1,1-dimethylbutyl, 1,1-dimethylhexyl, 1,1-dimethylheptyl, 3,3-dimethylbutyl, 4,4-dimethylpentyl and the like can be mentioned.

As the aryl group for $R^5$ or $R^6$, for example, phenyl, naphthyl and the like can be mentioned.

As the lower alkoxycarbonyl group for $R^7$, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like can be mentioned.

Specific examples of preferable novel indoline compound of the formula (I) include N-(5-methanesulfonylamino-4,6-dimethyl-1-propylindolin-7-yl)-2,2-dimethylpropanamide, N-[5-methanesulfonylamino-4,6-dimethyl-1-(2-methylpropyl)indolin-7-yl]-2,2-dimethylpropanamide, N-(1-butyl-5-methanesulfonylamino-4,6-dimethylindolin-7-yl)-2,2-dimethylpropanamide, N-[5-methanesulfonylamino-4,6-dimethyl-1-(3-methylbutyl)indolin-7-yl]-2,2-dimethylpropanamide, N-(5-methanesulfonylamino-4,6-dimethyl-1-pentylindolin-7-yl)-2,2-dimethylpropanamide, N-(5-methanesulfonylamino-4,6-dimethyl-1-octylindolin-7-yl)-2,2-dimethylpropanamide, N-(1-hexyl-5-methanesulfonylamino-4,6-dimethylindolin-7-yl)-2,2-dimethylpropanamide, N-(1-ethyl-5-methanesulfonylamino-4,6-dimethylindolin-7-yl)-2,2-dimethylpropanamide, N-(5-methanesulfonylamino-1,4,6-trimethylindolin-7-yl)-2,2-dimethylpropanamide, N-(4,6-dimethyl-1-octyl-5-sulfamoylaminoindolin-7-yl)-2,2-dimethylpropanamide, N-(4,16-dimethyl-1-propyl-5-sulfamoylaminoindolin-7-yl)-2,2-dimethylpropanamide, N-(4,6-dimethyl-1-pentyl-5-sulfamoylaminoindolin-7-yl)-2,2-dimethylpropanamide, N-[4,6-dimethyl-1-(2-methylpropyl)-5-sulfamoylaminoindolin-7-yl]-2,2-dimethylpropanamide, N-(1-butyl-4,6-dimethyl-5-sulfamoylaminoindolin-7-yl)-2,2-dimethylpropanamide, N-[4,6-dimethyl-1-(3-methylbutyl)-5-sulfamoylaminoindolin-7-yl]-2,2-dimethylpropanamide, N-(7-methanesulfonylamino-1,4,6-trimethylindolin-5-yl)-2,2-dimethylundecanamide, N-(7-methanesulfonylamino-4,6-dimethylindolin-5-yl)-2,2-dimethylundecanamide, N-[7-(2-propanesulfonylamino)-4,6-dimethylindolin-5-yl]-2,2-dimethylundecanamide, N-[7-(2-propanesulfonylamino)-4,6-dimethylindolin-5-yl]-2,2-dimethyloctanamide, N-[4,6-dimethyl-7-(p-toluene)sulfonylaminoindolin-5-yl]-2,2-dimethylundecanamide, N-(4,6-dimethyl-7-sulfamoylaminoindolin-5-yl)-2,2-dimethylundecanamide, N-(4,6-dimethyl-7-ureidoindolin-5-yl)-2,2-dimethylundecanamide, N-(4,6-dimethyl-5-nitro-1-octylindolin-7-yl)-2,2-dimethylpropanamide, N-(5-methanesulfonylaminomethyl-4,6-dimethyl-1-octylindolin-7-yl)-2,2-dimethylpropanamide, N-(4,6-dimethyl-1-octyl-5-ureidoindolin-7-yl)-2,2-dimethylpropanamide, N-[5-(N-acetylsulfamoylamino)-4,6-dimethyl-1-octylindolin-7-yl]-2,2-dimethylpropanamide, N-[5-(N-methoxycarbonylsulfamoylamino)-4,6-dimethyl-1-octylindolin-7-yl]-2,2-dimethylpropanamide, N-(1-isopropyl-5-methanesulfonylamino-4,6-dimethylindolin-7-yl)-2,2-dimethylpropanamide, N-[1-(2,2-dimethylpropyl)-5-methanesulfonylamino-4,6-dimethylindolin-7-yl]-2,2-dimethylpropanamide, N-(1-cyclobutylmethyl-5-methanesulfonylamino-4,6-dimethylindolin-7-yl)-2,2-dimethylpropanamide, N-(1-cyclopentyl-5-methanesulfonylamino-4,6-dimethylindolin-7-yl)-2,2-dimethylpropanamide, N-[5-methanesulfonylamino-4,6-dimethyl-1-(3-methyl-2-butenyl)indolin-7-yl]-2,2-dimethylpropanamide, N-(1-cyclopentyl-4,6-dimethyl-5-sulfamoylaminoindolin-7-yl)-2,2-dimethylpropanamide, N-(1-cyclopropylmethyl-5-methanesulfonylamino-4,6-dimethylindolin-7-yl)-2,2-dimethylpropanamide, N-[1-(2-ethoxyethyl)-4,6-dimethyl-5-sulfamoylaminoindolin-7-yl]-2,2-dimethylpropanamide, N-[1-(2-ethoxyethyl)-2,4,6-trimethyl-5-sulfamoylaminoindolin-7-yl]-2,2-dimethylpropanamide, N-[1-(2-methoxyethyl)-4,6-dimethyl-5-sulfamoylaminoindolin-7-yl]-2,2-dimethylpropanamide, N-[1-(2-methoxyethyl)-2,4,6-trimethyl-5-sulfamoylaminoindolin-7-yl]-2,2-dimethylpropanamide, N-[1-(2-ethylthioethyl)-4,6-dimethyl-5-sulfamoylaminoindolin-7-yl]-2,2-dimethylpropanamide hydrochloride, N-[4,6-dimethyl-1-(2-methylthioethyl)-5-sulfamoylaminoindolin-7-yl]-2,2-dimethylpropanamide hydrochloride, N-(2-methoxymethyl-4,6-dimethyl-1-propyl-5-sulfamoylaminoindolin-7-yl)-2,2-dimethylpropanamide, N-(2-ethoxymethyl-4,6-dimethyl-1-propyl-5-sulfamoylaminoindolin-7-yl)-2,2-dimethylpropanamide, N-(2-methylthiomethyl-4,6-dimethyl-1-propyl-5-sulfamoylaminoindolin-7-yl)-2,2-dimethylpropanamide, N-(2-ethylthiomethyl-4,6-dimethyl-1-propyl-5-sulfamoylaminoindolin-7-yl)-2,2-dimethylpropanamide, N-[1-(2-ethoxyethyl)-5-methanesulfonylamino-4,6-dimethylindolin-7-yl]-2,2-dimethylpropanamide, N-[1-(2-methoxyethyl)-5-methanesulfonylamino-4,6-dimethylindolin-7-yl]-2,2-dimethylpropanamide and the like, or a pharmaceutically acceptable salt thereof.

The compound (I) may form a pharmaceutically acceptable salt. When compound (I) has a basic group, an acid addition salt can be formed, wherein an acid to form an acid addition salt is free of particular limitation, as long as it can form a salt with a basic moiety and is pharmaceutically acceptable. As such acid, inorganic acids such as hydrochloric acid, sulfuric acid, phosphoric acid, nitric acid and the like, and organic acids such as oxalic acid, fumaric acid, maleic acid, citric acid, tartaric acid, methanesulfonic acid, toluenesulfonic acid and the like can be mentioned.

The novel indoline compound (I) and a pharmaceutically acceptable salt thereof of the present invention can be produced by any of the following production methods.

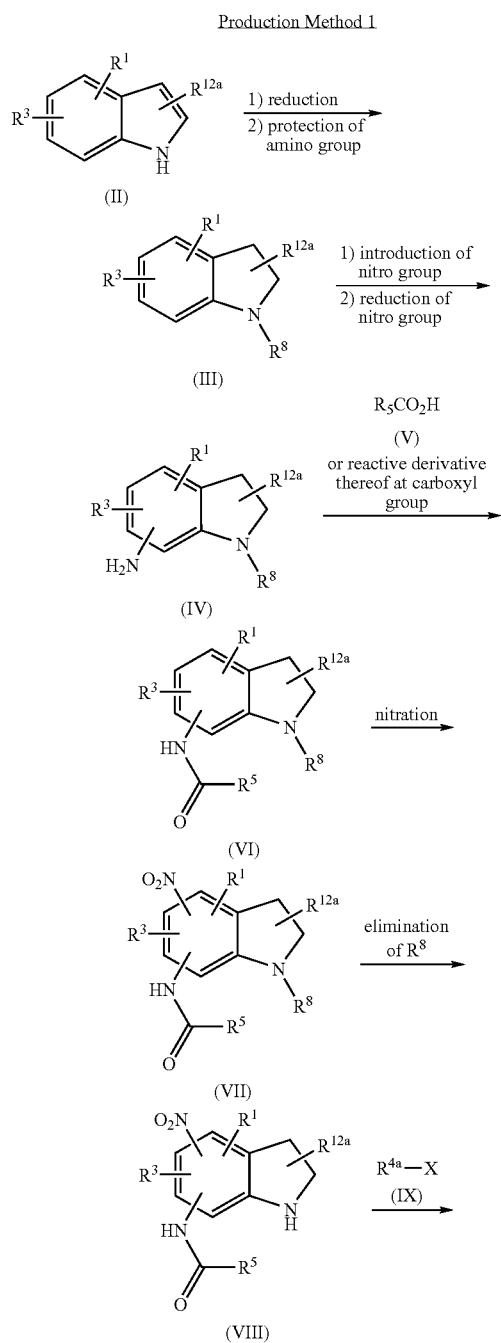

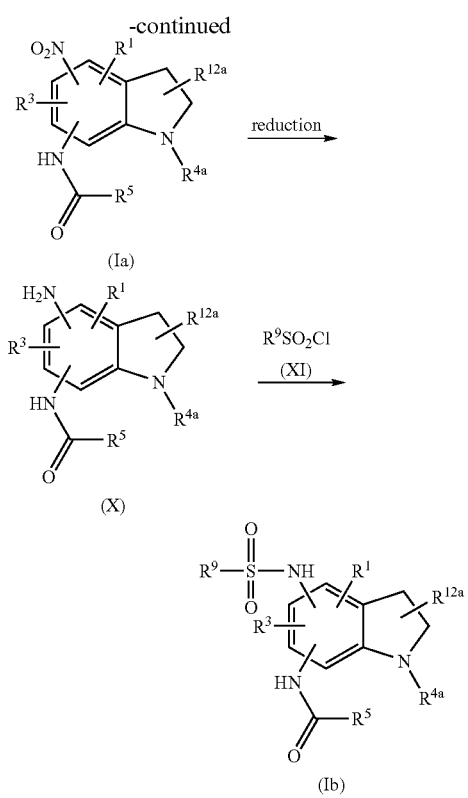

wherein $R^1$, $R^3$ and $R^5$ are each as defined above, $R^{4a}$ is alkyl group, cycloalkyl group, cycloalkylalkyl group or lower alkoxy lower alkyl group, $R^8$ is amino protecting group, $R^9$ is alkyl group or aryl group, $R^{12a}$ is hydrogen atom, lower alkyl group or lower alkoxy lower alkyl group and X is a leaving group such as halogen atom (chlorine atom, bromine atom or iodine atom), alkanesulfonyloxy (e.g., methanesulfonyloxy, ethanesulfonyloxy, propanesulfonyloxy or trifluoromethanesulfonyloxy etc.) or arylsulfonyloxy (e.g., phenylsulfonyloxy or tolylsulfonyloxy etc.) and the like.

In Production Method 1, novel indoline compound (Ia) and (Ib), wherein $R^2$ is —$NO_2$ or —$NHSO_2R^9$ ($R^9$ is alkyl group or aryl group), are produced.

As the amino protecting group for $R^8$, for example, formyl, acetyl, monochloroacetyl, dichloroacetyl, trichloroacetyl, trifluoroacetyl, methoxycarbonyl, ethoxycarbonyl, benzyloxycarbonyl, p-nitrobenzyloxycarbonyl, diphenylmethyloxycarbonyl, methoxymethylcarbonyl, methoxymethyloxycarbonyl, 2,2,2-trichloroethoxycarbonyl, 2-methylsulfonylethyloxycarbonyl, tert-butoxycarbonyl (hereinafter to be referred to as Boc), benzyl, trimethylsilyl, trityl and the like can be mentioned.

The compound (III) wherein $R^{12a}$ is hydrogen atom can be produced by reducing compound (II) wherein $R^{12a}$ is hydrogen atom [J. Eric Nordlander, et al., J. Org. Chem., 46, 778-782 (1981), Robin D. Clark, et al., Heterocycle, 22, 195-221 (1984), Vernon H. Brown, et al., J. Heterocycle. Chem., 6(4), 539-543 (1969)] to convert to an indoline skeleton, and then protecting the amino group.

The compound (III) wherein $R^{12a}$ is lower alkyl group can be produced from compound (II) wherein $R^{12a}$ is lower alkyl group [Beil 20, 311] by similar steps as mentioned above.

The compound (III) wherein $R^{12a}$ is lower alkoxy lower alkyl group can be produced by the method shown in Production Method 1-a.

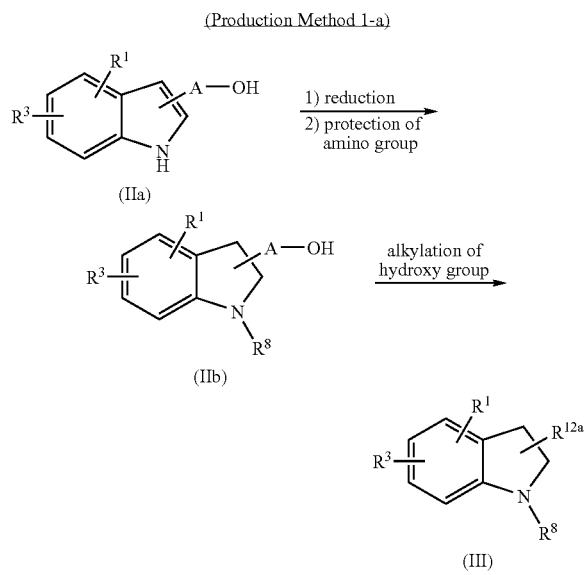

wherein $R^1$, $R^3$ and $R^8$ are each as defined above, $R^{12a}$ is lower alkoxy lower alkyl group, and A is lower alkylene group.

The compound (III) wherein $R^{12a}$ is lower alkoxy lower alkyl group can be produced by reducing compound (IIa) [Christopher A. Demerson, et al., J. Med. Chem., 19, 391-395 (1976), Gilbverto Spadoni, et al., J. Med. Chem., 41, 3624-3634 (1998)] to give indoline compound, protecting amino group to give compound (IIb), and then alkylating hydroxy group by a method known per se.

The compound (IV) of Production Method 1 can be produced by introducing nitro group onto a benzene ring of compound (III) by a method known per se and reducing the nitro group using a catalyst such as palladium-carbon and the like.

The compound (VI) can be produced by reacting compound (IV) with compound (V) or reactive derivative thereof at carboxyl group.

This reaction is generally carried out in an inert solvent. As the inert solvent, acetone, dioxane, acetonitrile, chloroform, benzene, methylene chloride, ethylene chloride, tetrahydrofuran, ethyl acetate, N,N-dimethylformamide, pyridine, water and the like, a mixture of these and the like can be specifically mentioned. In addition, a base such as triethylamine, pyridine, 4-dimethylaminopyridine, potassium carbonate and the like can be used.

The reaction temperature is generally −10° C. to 160° C., preferably 0° C. to 60° C., and the reaction time is generally 30 min to 10 hr.

The compound (V) is used for this reaction as a free carboxylic acid, or as a reactive derivative thereof, and both embodiments are encompassed in this reaction. To be specific, it is subjected to this reaction as a free acid or a salt with a base such as sodium, potassium, calcium, triethylamine, pyridine and the like, or a reactive derivative thereof such as an acid halide (acid chloride, acid bromide etc.), an acid anhydride, a mixed acid anhydride [a mixed acid anhydride with substituted phosphoric acid (dialkylphosphoric acid etc.), an alkyl carbonate (monoethyl carbonate etc.) and the like], an active amide (amide with imidazole and the like), an ester (cyanomethyl ester, 4-nitrophenyl ester etc.) and the like.

In this reaction, when compound (V) is used in the form of a free acid or salt, the reaction is preferably carried out in the presence of a condensing agent. As the condensing agent, for example, dehydrating agents such as N,N'-disubstituted carbodiimides (e.g., N,N'-dicyclohexylcarbodiimide etc.); carbodiimide compounds (e.g., 1-ethyl-3-(3'-dimethylaminopropyl)carbodiimide, N-cyclohexyl-N'-morpholinoethylcarbodiimide, N-cyclohexyl-N'-(4-diethylaminocyclohexyl)carbodiimide etc.); azolide compounds (e.g., N,N'-carbonyldiimidazole, N,N'-thionyldiimidazole etc.) and the like are used. When these condensing agents are used, the reaction is considered to proceed via a reactive derivative of carboxylic acid.

The compound (VIII) can be produced by nitrating compound (VI) by a method known per se to give compound (VII), and eliminating the amino protecting group for $R^8$ from the obtained compound (VII).

The amino protecting group can be eliminated by a method known per se, and as the elimination method, depending on the kind of the protecting group, for example, a method comprising treatment with an acid (hydrochloric acid, trifluoroacetic acid etc.) when, for example, it is formyl, tert-butoxycarbonyl, trityl and the like, a method comprising treatment with a base (sodium hydroxide, potassium hydroxide, sodium carbonate, sodium bicarbonate etc.), when, for example, it is acetyl, dichloroacetyl, trifluoroacetyl and the like, a method comprising catalytic reduction using palladium-carbon and the like as a catalyst when, for example, it is benzyl, benzyloxycarbonyl and the like, and the like can be mentioned.

The compound (Ia) can be produced by reacting compound (VIII) with compound (IX).

This reaction is carried out in a solvent that does not inhibit the reaction, such as acetone, dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide, pyridine, water and the like, and a mixture of these, in the presence of a base.

The molar ratio of compound (VIII) and compound (IX) to be used is not particularly limited, and 1 to 5 mol, preferably 1 to 3 mol, of compound (IX) is preferably used, per 1 mol of compound (VIII).

The base to be used for this reaction is not particularly limited, and inorganic bases such as alkali metal carbonates (e.g., sodium carbonate, sodium hydrogencarbonate, potassium carbonate, potassium hydrogencarbonate and the like), alkali metal hydroxides (e.g., sodium hydroxide, potassium hydroxide and the like) and the like, and organic bases such as alkali metal alcoholates (e.g., sodium methoxide, sodium ethoxide, potassium-tert-butoxide and the like), metal hydride compounds (e.g., sodium hydride, potassium hydride, calcium hydride and the like), triethylamine, diisopropylethylamine and the like can be mentioned.

The reaction temperature is generally −10° C. to 100° C., preferably 0° C. to 60° C., and the reaction time is generally 30 min to 10 hr.

The compound (Ib) can be produced by reducing nitro group of compound (Ia) by a method known per se to give compound (X) and reacting the obtained compound (X) with compound (XI).

The reaction between compound (X) and compound (XI), is carried out in a solvent that does not inhibit the reaction, such as acetone, dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide, pyridine, water and the like, or a mixture of these, in the presence of a base.

The molar ratio of compound (X) and compound (XI) to be used is not particularly limited, and 1 to 5 mol, preferably 1 to 3 mol, of compound (XI) is preferably used per 1 mol of compound (X).

The base to be used for this reaction is not particularly limited, and inorganic bases such as alkali metal carbonates (e.g., sodium carbonate, sodium hydrogencarbonate, potassium carbonate, potassium hydrogencarbonate and the like), alkali metal hydroxides (e.g., sodium hydroxide, potassium hydroxide and the like) and the like, and organic bases such as alkali metal alcoholates (e.g., sodium methoxide, sodium ethoxide, potassium-tert-butoxide and the like), metal hydride compounds (e.g., sodium hydride, potassium hydride, calcium hydride and the like), triethylamine, diisopropylethylamine and the like can be mentioned.

The molar ratio of compound (X) and base to be used is not particularly limited, and 1 to 5 mol, preferably 1 to 3 mol, of base is preferably used per 1 mol of compound (X).

While the reaction conditions such as reaction temperature, reaction time and the like vary depending on the reaction reagent, reaction solvent and the like to be used, the reaction is carried out generally at −30° C. to 150° C. for 30 min to several dozen hours.

wherein $R^1$, $R^3$, $R^{4a}$, $R^5$ and $R^{12a}$ are each as defined above and $R^{10}$ is lower alkyl group or lower alkoxy group.

In Production Method 2, novel indoline compounds (Ic) and (Id) wherein $R^2$ is —NHSO$_2$NHCOR$^{10}$ ($R^{10}$ is lower alkyl group or lower alkoxy group) or —NHSO$_2$NH$_2$ are produced.

The compound (Ic) can be produced by reacting compound (X) with compound (XII).

This reaction is carried out in a solvent that does not inhibit the reaction, such as acetone, dioxane, acetonitrile, tetrahydrofuran, chloroform, methylene chloride, ethylene chloride, benzene, toluene, xylene, ethyl acetate, N,N-dimethylformamide, N,N-dimethylacetamide, dimethyl sulfoxide, pyridine, water and the like, or a mixture of these, in the presence of a base.

The molar ratio of compound (X) and compound (XII) to be used is not particularly limited, and 1 to 5 mol, preferably 1 to 3 mol, of compound (XII) is preferably used per 1 mol of compound (X).

The base to be used for this reaction is not particularly limited, and inorganic bases such as alkali metal carbonates (e.g., sodium carbonate, sodium hydrogencarbonate, potassium carbonate, potassium hydrogencarbonate and the like), alkali metal hydroxides (e.g., sodium hydroxide, potassium hydroxide and the like) and the like, and organic bases such as alkali metal alcoholates (e.g., sodium methoxide, sodium ethoxide, potassium-tert-butoxide and the like), metal hydride compounds (e.g., sodium hydride, potassium hydride, calcium hydride and the like), triethylamine, diisopropylethylamine and the like can be mentioned.

The reaction temperature is generally −10° C. to 100° C., preferably 0° C. to 60° C. and the reaction time is generally 30 min to 10 hr.

The compound (Id) can be produced by hydrolyzing —COR$^{10}$ group of compound (Ic) by a method known per se under acidic or alkaline condition.

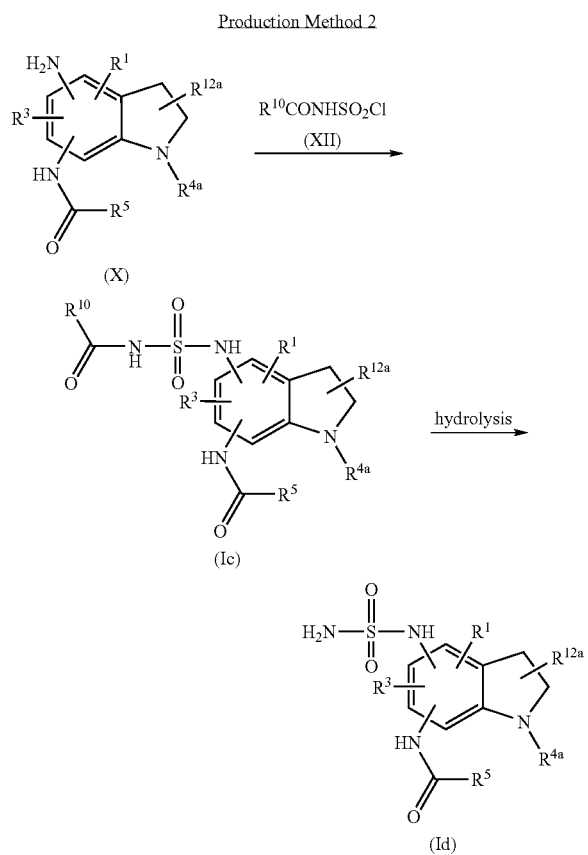

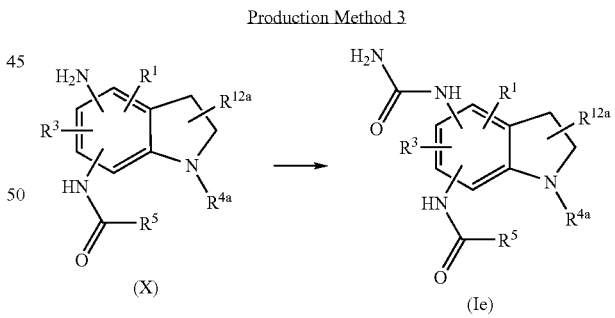

wherein $R^1$, $R^3$, $R^{4a}$, $R^5$ and $R^{12a}$ are each as defined above.

In Production Method 3, novel indoline compound (Ie) wherein $R^2$ is —NHCONH$_2$ is produced.

The compound (Ie) can be produced from compound (X) according to general synthetic methods of ureas such as addition reaction with isocyanates such as cyanic acid, chlorosulfonyl isocyanate and the like, condensation reaction with urea and the like [S. R. Sandler, W. Karo, "Organic Functional Group Preparation", Vol. 2, Academic Press (1971), Chapt. 6].

Production Method 4

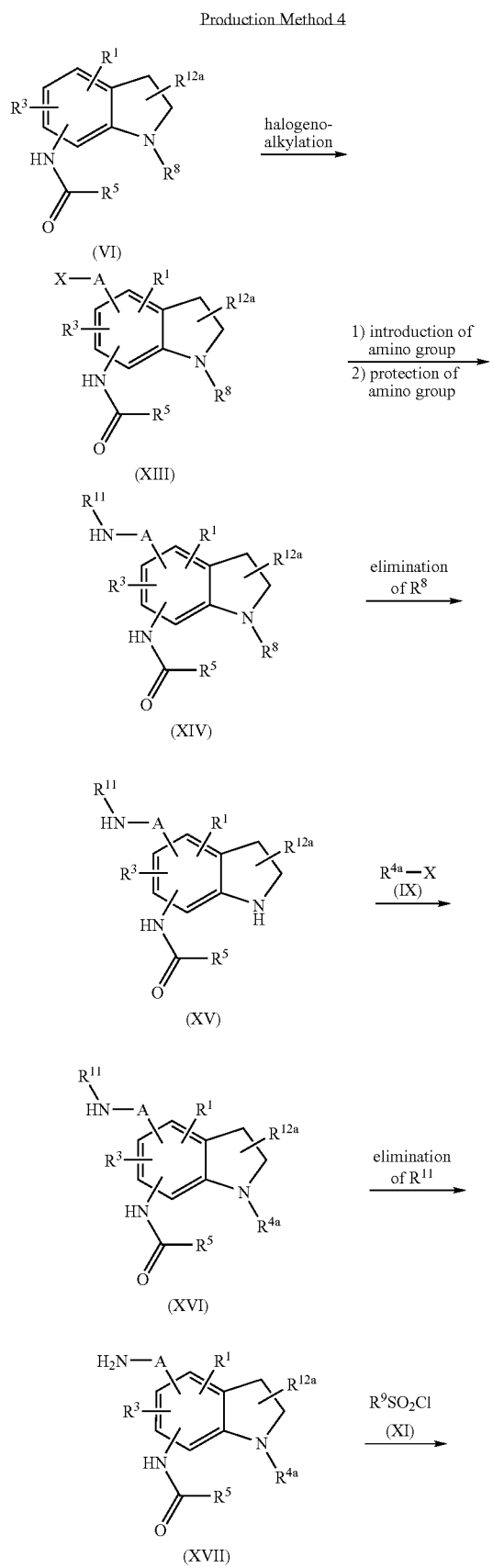

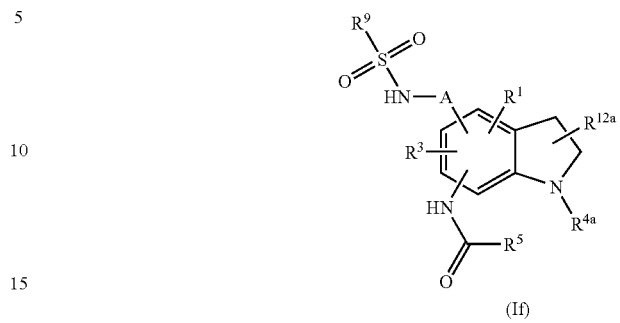

(If)

wherein $R^1$, $R^3$, $R^{4a}$, $R^5$, $R^8$, $R^9$, $R^{12a}$ and X are each as defined above, $R^{11}$ is amino protecting group, and A is lower alkylene group.

In Production Method 4, novel indoline compound (If) wherein $R^2$ is lower alkyl group substituted by —$NHSO_2R^9$ ($R^9$ is alkyl group or aryl group) is produced.

Compound (XIII) having halogenomethyl group can be produced by subjecting compound (VI) to halogenomethylation [R. C. Fuson. et al., Org. React., 1, 63 (1969), G. A. Olah. et al., "Friedel Crafts and Related Reaction" Vol. 2, 659 (1964)], and compound (XIII) having halogenoethyl group can be produced by converting halogen atom of the introduced halogenomethyl group to cyano group by a method known per se and hydrolyzing the cyano group to convert to carboxyl group or alkoxycarbonyl group, reducing the obtained carboxyl group or alkoxycarbonyl group by a method known per se to give an alcohol form and halogenating hydroxy group of the alcohol form. By repeating this step, compounds (XIII) having halogenopropyl group, halogenobutyl group and the like can be respectively produced.

The compound (XIV) can be produced by introducing amino group into compound (XIII) by a substituent conversion reaction known per se and protecting the amino group thereof. In this stage, compound (XIV) wherein both $R^8$ and $R^{11}$ are amino protecting groups is obtained. As $R^8$ and $R^{11}$, for example, formyl, acetyl, monochloroacetyl, dichloroacetyl, trichloroacetyl, trifluoroacetyl, methoxycarbonyl, ethoxycarbonyl, benzyloxycarbonyl, p-nitrobenzyloxycarbonyl, diphenylmethyloxycarbonyl, methoxymethylcarbonyl, methoxymethyloxycarbonyl, 2,2,2-trichloroethoxycarbonyl, 2-methylsulfonylethyloxycarbonyl, Boc, benzyl, trimethylsilyl, trityl and the like are used. It is essential that $R^8$ and $R^{11}$ are different and selectively eliminatable amino protecting groups.

The compound (XVI) can be produced from compound (XIV) by a method similar to the method of producing compound (Ia) from the compound (VII) via compound (VIII) in Production Method 1.

The compound (XVII) can be produced by eliminating the amino protecting group $R^{11}$ of compound (XVI) by a method known per se.

The compound (If) can be produced from compound (XVII) by a method similar to the method of producing compound (Ib) by reacting compound (X) with compound (XI) in Production Method 1.

Production Method 5

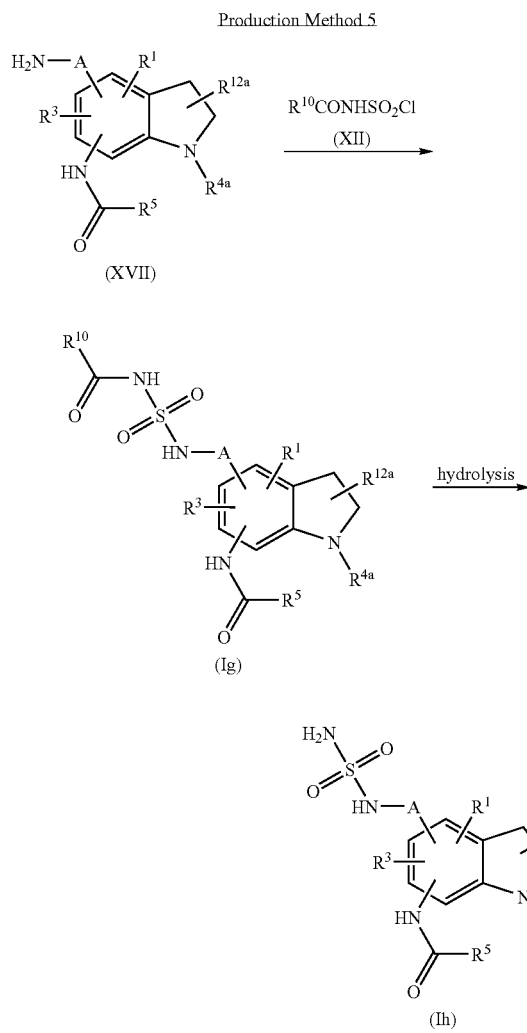

wherein $R^1$, $R^3$, $R^{4a}$, $R^5$, $R^{10}$, $R^{12a}$ and A are each as defined above.

In Production Method 5, novel indoline compounds (Ig) and (Ih) wherein $R^2$ is —NHSO$_2$NHCOR$^{10}$ ($R^{10}$ is lower alkyl group or lower alkoxy group) or lower alkyl group substituted by —NHSO$_2$NH$_2$ are produced.

The compounds (Ig) and (Ih) can be produced from compound (XVII) by a method similar to Production Method 2.

Production Method 6

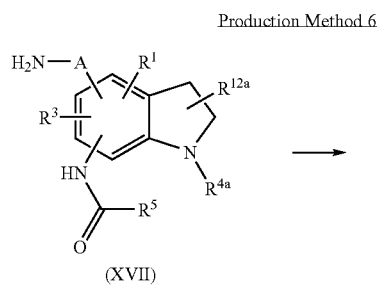

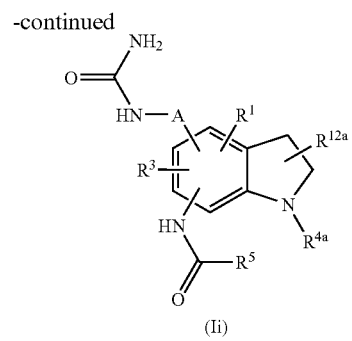

wherein $R^1$, $R^3$, $R^{4a}$, $R^{12a}$ and A are each as defined above.

In production method 6, novel indoline compound (Ii) wherein $R^2$ is lower alkyl group substituted by —NHCONH$_2$ is produced.

The compounds (Ii) can be produced from compound (XVII) by a method similar to Production Method 3.

Production Method 7

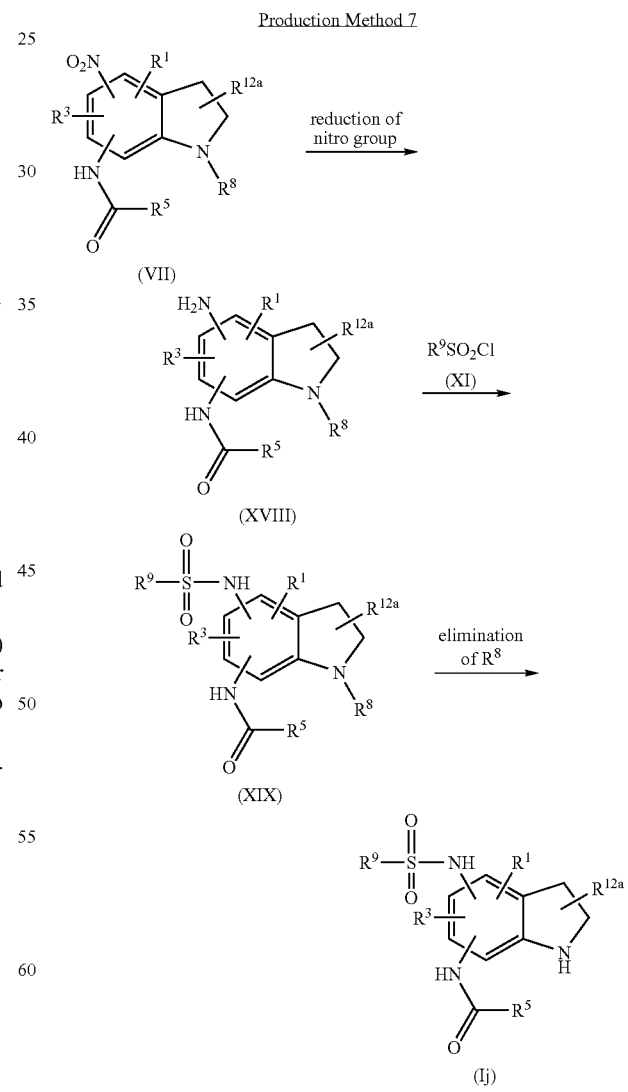

wherein $R^1$, $R^3$, $R^5$, $R^8$, $R^9$ and $R^{12a}$ are as defined above.

In Production Method 7, novel indoline compound (Ij) wherein $R^2$ is —$NHSO_2R^9$ ($R^9$ is alkyl group or aryl group) and $R^4$ is hydrogen atom is produced.

The compound (XIX) can be produced from compound (VII) by a method similar to the method of producing compound (Ib) from compound (Ia) via compound (X) in Production Method 1.

The compound (Ij) can be produced by eliminating the amino protecting group $R^8$ of compound (XIX) by a method known per se.

In Production Method 8, novel indoline compounds (Ik) and (II) wherein $R^2$ is —$NHSO_2NHCOR^{10}$ ($R^{10}$ is lower alkyl group or lower alkoxy group) or —$NHSO_2NH_2$ and $R^4$ is hydrogen atom are produced.

The compound (XX) can be produced from compound (XVIII) by a method similar to the method of producing compound (Ic) from compound (X) in Production Method 2.

The compound (Ik) can be produced by eliminating the amino protecting group $R^8$ of compound (XX) by a method known per se.

The compound (II) can be produced by hydrolyzing the —$COR^{10}$ group of compound (Ik) under acidic or alkaline condition by a method known per se.

Production Method 8

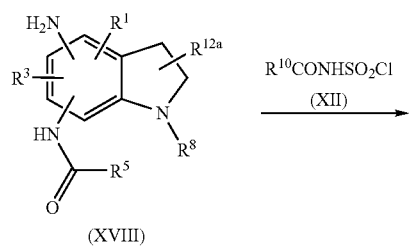

(XVIII)

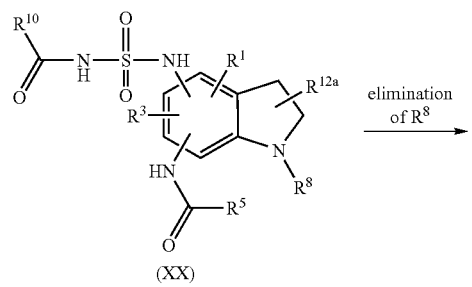

(XX)

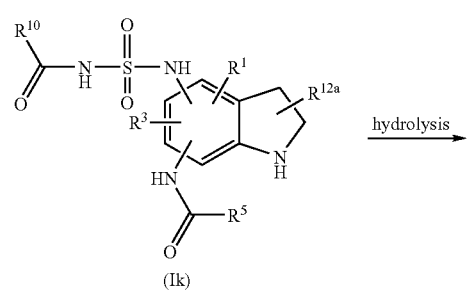

(Ik)

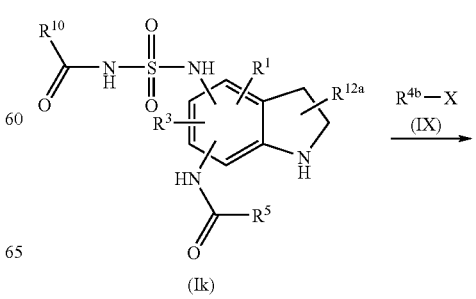

(II)

wherein $R^1$, $R^3$, $R^5$, $R^8$, $R^{10}$ and $R^{12a}$ are as defined above.

Production Method 9

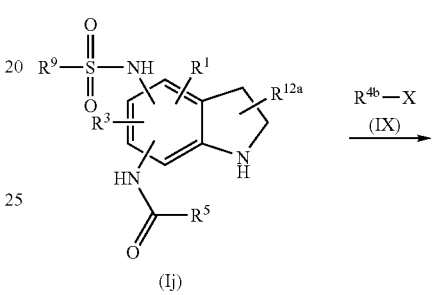

(Ij)

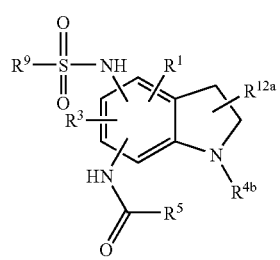

(Ib')

wherein $R^1$, $R^3$, $R^5$, $R^9$ and $R^{12a}$ are as defined above, and $R^{4b}$ is alkyl group, cycloalkyl group, cycloalkylalkyl group, lower alkenyl group or lower alkoxy lower alkyl group.

In Production Method 9, a novel indoline compound (Ib') is produced from compound (Ij).

The compound (Ib') can be produced by a method similar to the method of producing compound (Ia) by reacting compound (VIII) with compound (IX) in Production Method 1.

Production Method 10

-continued

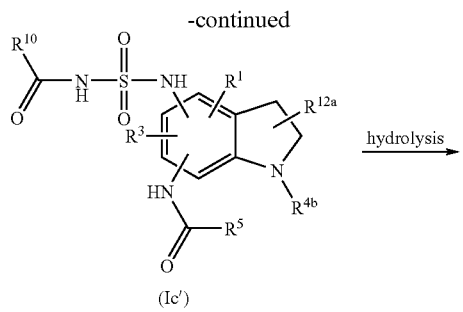

(Ic')

hydrolysis

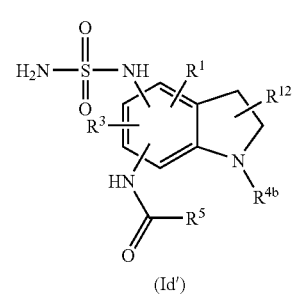

(Id')

wherein $R^1$, $R^3$, $R^{4b}$, $R^5$, $R^{10}$ and $R^{12a}$ are as defined above.

In Production Method 10, novel indoline compounds (Ic') and (Id') are produced from compound (Ik).

The compound (Ic') can be produced by a method similar to the method of producing compound (Ia) by reacting compound (VIII) with compound (IX) in Production Method 1 in the same manner as in Production Method 9.

The compound (Id') can be produced by hydrolyzing the —$COR^{10}$ group of compound (Ic') under acidic or alkaline condition by a method known per se.

Production Method 11

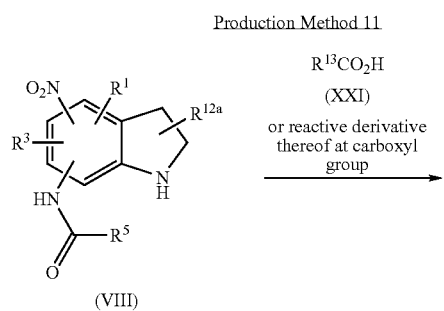

(VIII)

$R^{13}CO_2H$
(XXI)
or reactive derivative thereof at carboxyl group
→

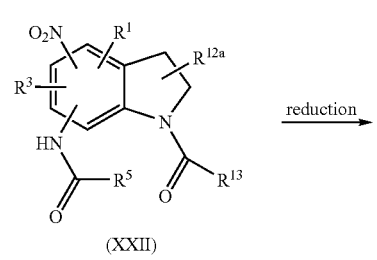

(XXII)

reduction →

-continued

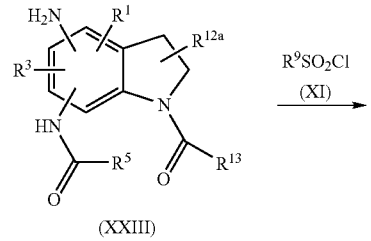

(XXIII)

$R^9SO_2Cl$
(XI)
→

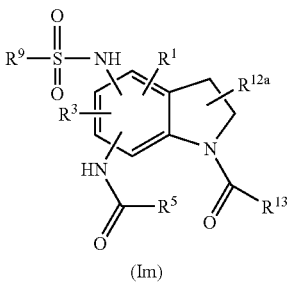

(Im)

wherein $R^1$, $R^3$, $R^5$, $R^9$ and $R^{12a}$ are as defined above, and $R^{13}$ is hydrogen atom or lower alkyl group.

In Production Method 11, novel indoline compound (Im) wherein $R^2$ is —$NHSO_2R^9$ ($R^9$ is alkyl group or aryl group) and $R^4$ is —$COR^{13}$ ($R^{13}$ is hydrogen atom or lower alkyl group) is produced.

The compound (XXII) can be produced from compound (VIII) and compound (XXI) by a method similar to the method of producing compound (VI) from the compound (IV) in Production Method 1.

The compound (Im) can be produced from compound (XXII) by a method similar to the method of producing compound (Ib) from the compound (Ia) via compound (X) in Production Method 1.

Production Method 12

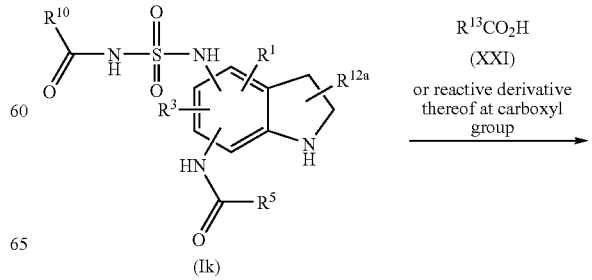

(Ik)

$R^{13}CO_2H$
(XXI)
or reactive derivative thereof at carboxyl group
→

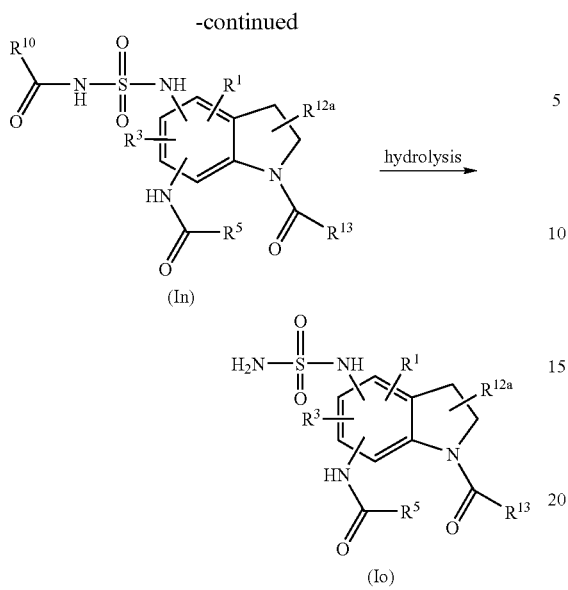

wherein $R^1$, $R^3$, $R^5$, $R^8$, $R^{10}$, $R^{12a}$ and $R^{13}$ are as defined above.

In Production Method 12, novel indoline compounds (In) and (Io) wherein, in the formula (I), $R^2$ is —NHSO$_2$NHCOR$^{10}$ ($R^{10}$ is lower alkyl group or lower alkoxy group) or —NHSO$_2$NH$_2$, and $R^4$ is —COR$^{13}$ ($R^{13}$ is hydrogen atom or lower alkyl group) are produced.

The compound (In) can be produced from compound (Ik) and compound (XXI) by a method similar to the method of producing compound (VI) from the compound (IV) in Production Method 1 in the same manner as in Production Method 11.

The compound (Io) can be produced by hydrolyzing the —COR$^{10}$ group of compound (In) under acidic or alkaline condition by a method known per se.

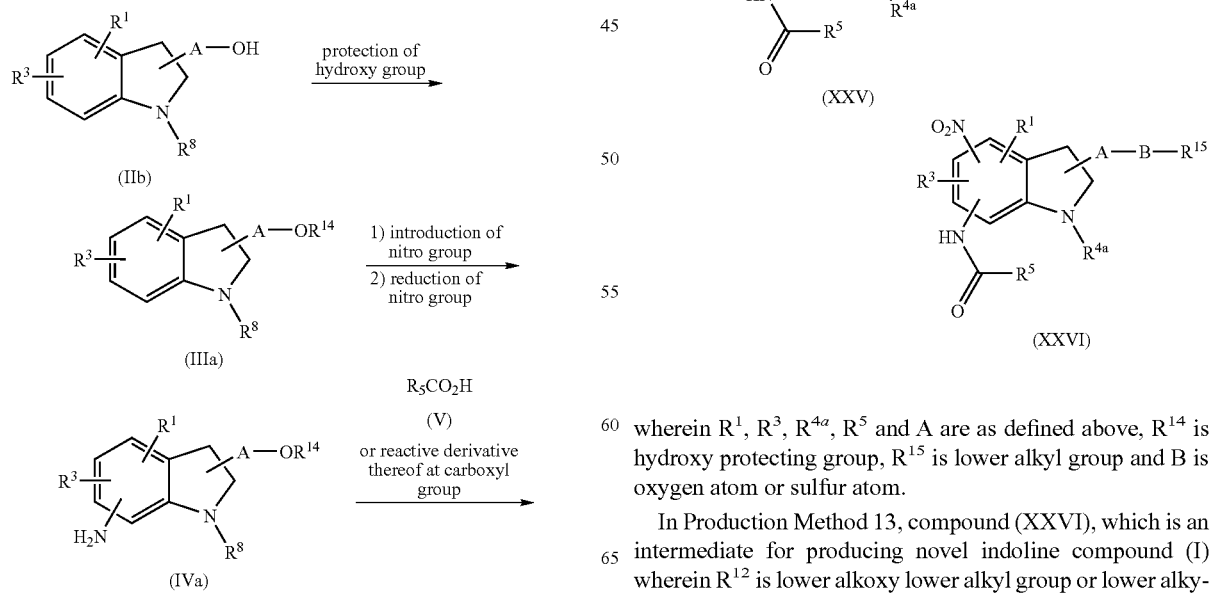

wherein $R^1$, $R^3$, $R^{4a}$, $R^5$ and A are as defined above, $R^{14}$ is hydroxy protecting group, $R^{15}$ is lower alkyl group and B is oxygen atom or sulfur atom.

In Production Method 13, compound (XXVI), which is an intermediate for producing novel indoline compound (I) wherein $R^{12}$ is lower alkoxy lower alkyl group or lower alkylthio lower alkyl group, is produced.

As the hydroxy protecting group for $R^{14}$, for example, a group capable of forming ethers and acetals, such as methyl, isopropyl, tert-butyl, benzyl, allyl, methoxymethyl, tetrahydropyranyl, p-bromophenacyl, trimethylsilyl and the like, a group capable of forming esters, such as formyl, acetyl, monochloroacetyl, dichloroacetyl, trifluoroacetyl, methoxycarbonyl, ethoxycarbonyl, benzyloxycarbonyl, p-nitrobenzyloxycarbonyl, 2,2,2-trichloroethoxycarbonyl, benzoyl, methanesulfonyl, benzenesulfonyl, p-toluenesulfonyl and the like, and the like can be mentioned.

The compound (IVa) can be produced by protecting the hydroxy group of compound (IIb) by a method known per se to give compound (IIIa), and by a method similar to the method of producing compound (IV) from the compound (III) in Production Method 1.

The compound (XXIV) can be produced from compound (IVa) by a method similar to the method of producing compound (Ia) from the compound (IV) in Production Method 1.

The compound (XXV) can be produced by eliminating the hydroxy protecting group $R^{14}$ of compound (XXIV). While the method of eliminating a hydroxy protecting group varies depending on the kind thereof, generally, a method known per se as the technique in this field can be used for the elimination.

The compound (XXVI) wherein -A-B—$R^{15}$ is lower alkoxy lower alkyl group or lower alkylthio lower alkyl can be produced by a method known per se, which comprises converting the hydroxy group of compound (XXV) to a leaving group such as halogen atom (chlorine atom, bromine atom or iodine atom), alkanesulfonyloxy (e.g., methanesulfonyloxy, ethanesulfonyloxy, propanesulfonyloxy, trifluoromethanesulfonyloxy etc.), arylsulfonyloxy (e.g., phenylsulfonyloxy, tolylsulfonyloxy etc.) and the like, and reacting the compound with lower alcohol or lower alkylthiol compound in the presence of a base.

In addition, compound (XXVI) wherein -A-B—$R^{15}$ is lower alkoxy lower alkyl group can be also produced by a method known per se, which comprises reacting compound (XXV) with $R^5$—X (compound (XXVII)) wherein $R^{15}$ and X are as defined above.

Moreover, compound (XXVI) wherein -A-B—$R^{15}$ is lower alkylthio lower alkyl group can be also produced by converting the hydroxy group of compound (XXV) to thiol group by a method known per se and reacting the compound with compound (XXVII).

The compound (XXVI) produced by Production Method 13 is used as an intermediate in Production Method 1-3 or Production Method 7-12 and can produce the corresponding novel indoline compound (I).

Production Method 14

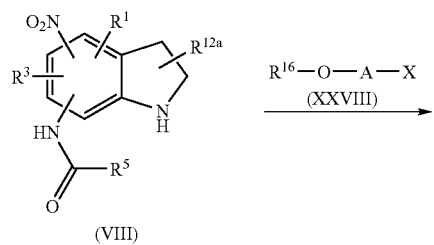

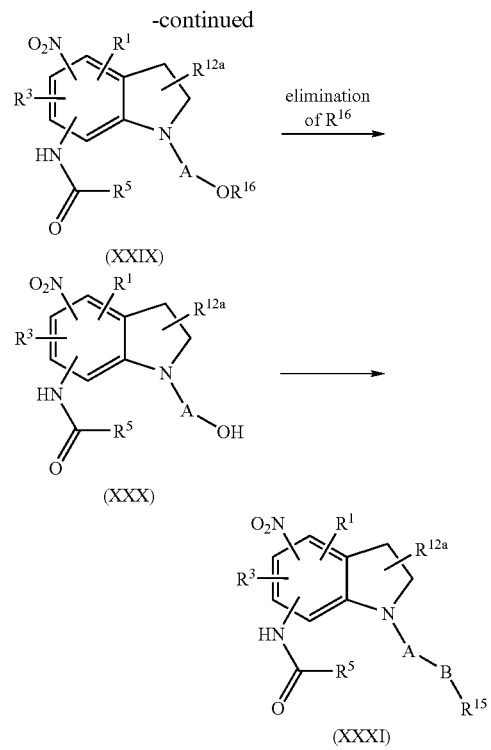

wherein $R^1$, $R^3$, $R^5$, $R^{12a}$, $R^{15}$, X, A and B are as defined above and $R^{16}$ is hydrogen atom or hydroxy protecting group.

In Production Method 14, compound (XXXI), which is an intermediate for producing novel indoline compound (I) wherein $R^4$ is lower alkoxy lower alkyl group or lower alkylthio lower alkyl group, is produced.

The compound (XXIX) can be produced from compound (VIII) and compound (XXVIII) by a method similar to the method of producing compound (Ia) from the compound (VIII) and compound (IX) in Production Method 1.

When $R^{16}$ is hydroxy protecting group, compound (XXX) can be produced by eliminating the hydroxy protecting group $R^{16}$ of compound (XXIX) by a method known per se.

In addition, compound (XXX) can be also produced from compound (VIII) and compound (XXVIII) wherein $R^{16}$ is hydrogen atom.

The compound (XXXI) can be produced from compound (XXX) by a method similar to the method of producing compound (XXVI) from the compound (XXV) in Production Method 13.

The compound (XXXI) produced by Production Method 14 is used as an intermediate in Production Methods 1-3 or Production Methods 7-12 and produces the corresponding novel indoline compound (I).

Production Method 15

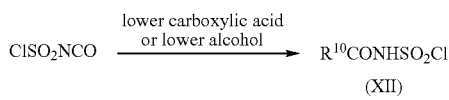

wherein $R^{10}$ is as defined above.

In Production Method 15, compound (XII) to be used for Production Methods 2, 5 and 8 is produced.

The compound (XII) can be produced from chlorosulfonyl isocyanate by a method known per se, or reacted with lower carboxylic acid to give compound (XII) wherein $R^{10}$ is lower alkyl group, and reacted with lower alcohol to give compound (XII) wherein $R^{10}$ is lower alkoxy group.

When $R^{12}$, which is a substituent at the 5-membered ring of the indoline skeleton of compound (I), is lower alkyl group, lower alkoxy lower alkyl group or lower alkylthio lower alkyl group, the carbon atom substituted by $R^{12}$ becomes an asymmetric carbon. In this case, compound (I) contains stereoisomers based on the asymmetric carbon, which are also encompassed in the present invention.

The compound of the present invention (I) obtained as mentioned above can be purified by conventionally known methods (e.g., chromatography, recrystallization etc.).

Moreover, compound (I) can be converted to a pharmaceutically acceptable salt thereof by a method known per se.

While the dose of compound (I) and a pharmaceutically acceptable salt thereof of the present invention varies depending on the subject of administration, conditions, and other factors, when orally administered to, for example, adult patients with hypercholesterolemia, a single dose of 0.1 mg to 50 mg/kg body weight can be administered about 1 to 3 times a day.

EXAMPLES

The present invention is explained in detail in the following by referring to Examples, which are not to be construed as limitative.

Example 1

N-(4,6-dimethyl-5-nitro-1-octylindolin-7-yl)-2,2-dimethylpropanamide (1) 4,6-Dimethylindole (160 g) was dissolved in acetic acid (800 mL), and sodium cyanoborohydride (138 g) was added in portions under ice-cooling over 1 hr. The mixture was stirred at the same temperature for 2 hr. The reaction solution was poured into ice water (3 L) and ethyl acetate (2 L) was added. The mixture was neutralized with aqueous sodium hydroxide solution at not more than 20° C. and the aqueous layer was saturated with sodium chloride. The ethyl acetate layer was separated and dried over sodium sulfate, and ethyl acetate was evaporated under reduced pressure. The obtained residue was dissolved in benzene (600 mL) and acetic anhydride (135 g) was added. The mixture was stirred at room temperature for 1 hr and the precipitated crystals were collected by filtration. The solvent of the filtrate was evaporated under reduced pressure, and the residue was dissolved in chloroform, washed successively with saturated aqueous sodium hydrogencarbonate and saturated brine, and dried over sodium sulfate. Chloroform was evaporated under reduced pressure and the residue was combined with the crystals obtained earlier to give 1-acetyl-4,6-dimethylindoline as crystals (208 g).

IR ν (Nujol) cm$^{-1}$; 1655, 1595. $^1$H-NMR (CDCl$_3$) δ (ppm); 2.18 (6H, s), 2.30 (3H, s), 3.00 (2H, t, J=8.5 Hz), 4.03 (2H, t, J=8.5 Hz), 6.66 (1H, s), 7.89 (1H, s).

(2) The compound (200 g) obtained in (1) was dissolved in acetic acid (4 L) and bromine (85 mL) was added dropwise under ice-cooling. The mixture was stirred at room temperature for 30 min. The reaction solution was poured into ice water (20 L), sodium hydrogensulfite (5 g) was added, and the mixture was stirred for 30 min. The precipitated crystals were collected by filtration, dissolved in chloroform (2 L), washed successively with water and saturated brine and dried over sodium sulfate. Chloroform was evaporated under reduced pressure and the obtained crystalline residue was recrystallized from methanol to give 1-acetyl-5-bromo-4,6-dimethylindoline as white crystals (185 g).

IR ν (Nujol) cm$^{-1}$; 1660. $^1$H-NMR (CDCl$_3$) δ (ppm); 2.19 (3H, s), 2.27 (3H, s), 2.39 (3H, s), 3.06 (2H, t, J=8.5 Hz), 4.03 (2H, t, J=8.5 Hz), 7.99 (1H, s).

(3) To a mixture of fumed nitric acid (44 mL), acetic acid (500 mL) and concentrated sulfuric acid (500 mL) was added the compound (185 g) obtained in (2) in portions at −5 to 0° C. over 1 hr, and the mixture was stirred under ice-cooling for 3 hr. The reaction solution was poured into ice water (6 L), and the precipitated crystals were collected by filtration. The obtained crystals were dissolved in chloroform (3 L), washed successively with water and saturated brine and dried over sodium sulfate. Chloroform was evaporated under reduced pressure to give 1-acetyl-5-bromo-4,6-dimethyl-7-nitroindoline as crystals (209 g).

IR ν (Nujol) cm$^{-1}$; 1672, 1654. $^1$H-NMR (CDCl$_3$) δ (ppm); 2.20 (3H, s), 2.35 (3H, s), 2.45 (3H, s), 3.12 (2H, t, J=8.5 Hz), 4.16 (2H, t, J=8.5 Hz).

(4) The compound (75 g) obtained in (3) was dissolved in a mixture (1 L) of chloroform-methanol (1:1). 5% Palladium-carbon (10 g) was added, and the mixture was subjected to catalytic hydrogenation at 40° C. for 2 days at ordinary pressure. Partly precipitated 1-acetyl-7-amino-4,6-dimethylindoline bromate was filtered off together with palladium-carbon and the obtained solid was neutralized with saturated aqueous sodium hydrogencarbonate, and extracted with chloroform (0.5 L). The solvent in the filtrate was evaporated under reduced pressure and the residue was similarly neutralized with saturated aqueous sodium hydrogencarbonate and extracted with chloroform (1 L). The extract was combined with the chloroform layer mentioned earlier, washed with saturated brine and dried over sodium sulfate, and chloroform was evaporated under reduced pressure. The obtained residue was dissolved in chloroform (300 mL). Pivaloyl chloride (27.7 g) was added and triethylamine (29.1 g) was added dropwise at not more than 20° C., and the mixture was stirred at room temperature for 1 hr. Chloroform (1 L) was added and the mixture was washed successively with 5% aqueous citric acid and saturated brine (each 500 mL) and dried over sodium sulfate. Chloroform was evaporated under reduced pressure and n-hexane (200 mL) was added to the obtained crystalline residue. The crystals were washed by stirring the mixture and filtered to give N-(1-acetyl-4,6-dimethylindolin-7-yl)-2,2-dimethylpropanamide as crystals (49 g).

IR ν (Nujol) cm$^{-1}$; 1677, 1639. $^1$H-NMR (CDCl$_3$) δ (ppm); 1.27 (9H, s), 2.17 (6H, s), 2.29 (3H, s), 2.94 (2H, t, J=8.5 Hz), 4.09 (2H, t, J=8.5 Hz), 6.87 (1H, s), 9.09 (1H, br-s).

(5) The compound (1.99 g) obtained in (4) was dissolved in acetic acid (20 mL) and fumed nitric acid (0.41 mL) was added dropwise under ice-cooling. The mixture was stirred at 50° C. for 4 hr and the reaction mixture was poured into ice water. The precipitated crystals were collected by filtration, and the obtained crystals were dissolved in chloroform (300 mL). The solution was washed successively with saturated aqueous sodium hydrogencarbonate and saturated brine and dried over sodium sulfate. Chloroform was evaporated under reduced pressure and the obtained residue was purified by silica gel column chromatography to give N-(1-acetyl-4,6-dimethyl-5-nitroindolin-7-yl)-2,2-dimethylpropanamide (2.2 g).

IR ν (Nujol) cm⁻¹; 1670, 1641, 1583, 1528. ¹H-NMR (CDCl₃) δ (ppm); 1.27 (9H, s), 2.11 (3H, s), 2.15 (3H, s), 2.32 (3H, s), 3.04 (2H, t, J=8.0 Hz), 4.16 (2H, t, J=8.0 Hz), 9.07 (1H, br-s).

(6) The compound (0.8 g) obtained in (5) was dissolved in methanol (8 mL) and 4M aqueous sodium hydroxide solution (3 mL) was added. The mixture was stirred at 80° C. for 15 mm. The solvent was evaporated under reduced pressure and the obtained residue was dissolved in chloroform (50 mL). The solution was washed successively with water and saturated brine and dried over sodium sulfate. Chloroform was evaporated under reduced pressure and the obtained residue was purified by silica gel column chromatography to give N-(4,6-dimethyl-5-nitroindolin-7-yl)-2,2-dimethylpropanamide (0.68 g).

IR ν (Nujol) cm⁻¹; 1643, 1597, 1508. ¹H-NMR (CDCl₃) δ (ppm); 1.35 (9H, s), 2.14 (3H, s), 2.16 (3H, s), 3.01 (2H, t, J=8.5 Hz), 3.67 (2H, t, J=8.5 Hz), 4.26 (1H, br), 7.03 (1H, br-s).

(7) The compound (3.5 g) obtained in (6) was dissolved in N,N-dimethylformamide (40 mL) and sodium hydride (60% oil suspension) (576 mg) was added in portions under a nitrogen atmosphere and under ice-cooling. After stirring at room temperature for 10 min, octyl iodide (2.6 mL) was added and the mixture was at the same temperature for 17 hr. Water (100 mL) was added and the mixture was extracted with diethyl ether (300 mL). The diethyl ether layer was washed successively with water and saturated brine and dried over sodium sulfate. Diethyl ether was evaporated under reduced pressure and the obtained residue was purified by silica gel column chromatography to give the title compound as crystals (3.2 g).

IR ν (Nujol) cm⁻¹; 1649, 1597, 1560, 1516. ¹H-NMR (CDCl₃) δ (ppm); 0.88 (3H, br-t), 1.08-1.51 (12H, m), 1.33 (9H, s), 2.03 (3H, s), 2.10 (3H, s), 2.86 (2H, t), 3.23 (2H, br-t), 3.54 (2H, t, J=8.5 Hz), 6.74 (1H, br-s).

Example 2

N-(5-methanesulfonylamino-4,6-dimethyl-1-octylindolin-7-yl)-2,2-dimethylpropanamide The compound (3.2 g) obtained Example 1 was dissolved in a mixture (120 mL) of methanol-toluene (3:1) and 5% palladium-carbon (0.48 g) was added. The mixture was subjected to catalytic hydrogenation at room temperature and 2 kgf/cm² for 17 hr. Palladium-carbon was filtered off and the solvent was evaporated under reduced pressure. The obtained residue was dissolved in chloroform (300 mL), washed with saturated brine and dried over sodium sulfate. Chloroform was evaporated under reduced pressure and the obtained residue was dissolved in chloroform (30 mL). Triethylamine (3.32 mL) was added, methanesulfonyl chloride (1.23 mL) was added dropwise under ice-cooling, and the mixture was stirred at room temperature for 3 hr. Chloroform (100 mL) was added, washed successively with 5% aqueous citric acid, water and saturated brine and dried over sodium sulfate. Chloroform was evaporated under reduced pressure and the obtained residue was purified by silica gel column chromatography to give the title compound as crystals (3.0 g).

IR ν (Nujol) cm⁻¹; 3358, 1665, 1597, 1502. ¹H-NMR (CDCl₃) δ (ppm); 0.88 (3H, br-t), 1.18-1.58 (12H, m), 1.34 (9H, s), 2.10 (3H, s), 2.15 (3H, s), 2.86 (2H, t, J=8.3 Hz), 2.97 (3H, s), 3.15 (2H, br-t), 3.24 (2H, t, J=8.3 Hz), 6.10 (1H, br), 6.85 (1H, br-s).

Example 3

N-[5-(N-acetylsulfamoylamino)-4,6-dimethyl-1-octylindolin-7-yl]-2,2-dimethylpropanamide (1) Chlorosulfonyl isocyanate (3.04 mL) was added dropwise to acetic acid (2.0 mL) under ice-cooling and n-hexane was added. The precipitated crystals were collected by filtration to give acetylsulfamoyl chloride as crystals (5.31 g).

(2) The compound (3.0 g) obtained in Example 1 was dissolved in a mixture (110 mL) of methanol-toluene (3:1), and 5% palladium-carbon (0.45 g) was added. The mixture was subjected to catalytic hydrogenation at room temperature and 2 kgf/cm² for 17 hr. Palladium-carbon was filtered off, and the solvent was evaporated under reduced pressure. The obtained residue was dissolved in chloroform (300 mL). The solution was washed with saturated brine and dried over sodium sulfate. Chloroform was evaporated under reduced pressure. The obtained residue (N-(5-amino-4,6-dimethyl-1-octylindolin-7-yl)-2,2-dimethylpropanamide) (2.67 g) was dissolved in chloroform (27 mL) and triethylamine (1.2 mL) and the compound (2.25 g) obtained in (1) were added at −10° C. The mixture was stirred at room temperature for 30 min. 10% Aqueous citric acid was added to the reaction mixture and the mixture was extracted with chloroform (100 mL). The chloroform layer was washed successively with saturated aqueous sodium hydrogencarbonate and saturated brine and dried over sodium-sulfate. Chloroform was evaporated under reduced pressure and the obtained residue was purified by silica gel column chromatography. The obtained crystals were recrystallized from toluene (50 mL) to give the title compound as crystals (1.84 g).

IR ν (Nujol) cm⁻¹; 3302, 1701, 1649, 1163. ¹H-NMR (CDCl₃) δ (ppm); 0.88 (3H, br-t), 1.00-1.70 (12H, m), 1.29 (9H, s), 1.93 (3H, s), 1.97 (3H, s), 2.08 (3H, s), 2.77 (2H, t, J=8.2 Hz), 3.14 (2H, t, J=4.5 Hz), 3.40 (2H, t, J=8.2 Hz), 5.00 (1H, br-s), 6.80 (1H, br-s), 7.09 (1H, s).

Example 4

N-[5-(N-methoxycarbonylsulfamoylamino)-4,6-dimethyl-1-octylindolin-7-yl]-2,2-dimethylpropanamide Methanol (0.13 mL) was added to methylene chloride (2.6 mL) and chlorosulfonyl isocyanate (0.29 mL) was added at −20° C. The mixture was stirred at −20° C. to 10° C. for 20 min. N-(5-Amino-4,6-dimethyl-1-octylindolin-7-yl)-2,2-dimethylpropanamide (612 mg) and triethylamine (0.46 mL) were added to the reaction mixture and the mixture was further stirred at −9° C. for 30 min. Methylene chloride was added to the reaction mixture, and the mixture was washed successively with 10% aqueous citric acid, saturated aqueous sodium hydrogencarbonate and saturated brine and dried over sodium sulfate. Methylene chloride was evaporated under reduced pressure. The obtained residue was purified by silica gel column chromatography to give the title compound as crystals. (601 mg).

IR ν (Nujol) cm⁻¹; 3300, 1736, 1655, 1597. ¹H-NMR (CDCl₃) δ (ppm); 0.87 (3H, br-t), 1.00-1.60 (12H, m), 1.95 (3H, s), 2.10 (3H, s), 2.77 (2H, t, J=8.0 Hz), 3.15 (2H, br-t), 3.42 (2H, t, J=8.0 Hz), 3.78 (3H, s), 6.70 (1H, br-s), 7.03 (1H, br-s), 7.26 (1H, br-s).

Example 5

N-[5-(N-tert-butoxycarbonylsulfamoylamino)-4,6-dimethyl-1-octylindolin-7-yl]-2,2-dimethylpropanamide tert-Butanol (0.85 mL) was dissolved in methylene chloride (17 mL) and chlorosulfonyl isocyanate (0.77 mL) was added at −18° C. The mixture was stirred at the same temperature for 30 min and N-(5-amino-4,6-dimethyl-1-octylindolin-7-yl)-2,2-dimethylpropanamide (1.66 g) and triethylamine (1.24 mL) were added. The mixture was further stirred at −5° C. for 30 min. Methylene chloride (50 mL) was added, and the mixture was washed successively with 10% aqueous citric acid, saturated aqueous sodium hydrogencarbonate, and then saturated brine (50 mL) and dried over sodium sulfate. Then, methylene chloride was evaporated under reduced pressure. The obtained residue was purified by silica gel column chromatography to give the title compound as crystals (1.9 g).

IR ν (Nujol) cm$^{-1}$; 3371, 3167, 1755, 1728, 1655, 1597. $^1$H-NMR (DMSO-d$_6$) δ (ppm); 0.88 (3H, br-t), 1.05-1.80 (21H, m), 1.49 (9H, s), 1.98 (3H, s), 2.14 (3H, s), 2.78 (2H, br-t), 3.17 (2H, br-t), 3.39 (2H, br-t), 6.69 (1H, br-s), 7.16 (2H, br-s).

Example 6

N-(4,6-dimethyl-1-octyl-5-sulfamoylaminoindolin-7-yl)-2,2-dimethylpropanamide hydrochloride The compound (1.86 g) obtained in Example 5 was dissolved in formic acid (7.5 mL) and 8.51 M hydrogen chloride—2-propanol solution (1.98 mL) was added under ice-cooling. The mixture was stirred at the same temperature for 20 min. Diethyl ether (50 mL) was added, and the precipitated crystals were collected by filtration to give the title compound as crystals (1.34 g).

IR ν (Nujol) cm$^{-1}$; 3290, 3225, 3059, 1676, 1508. $^1$H-NMR (DMSO-d$_6$) δ (ppm); 0.84 (3H, br-t), 1.00-1.95 (21H, m), 2.13 (3H, s), 2.30 (3H, s), 2.95-3.50 (4H, m), 3.81 (2H, br-t), 5.50-9.00 (3H, br), 8.55 (1H, br-s), 9.37 (1H, br-s).

Example 7

N-(4,6-dimethyl-1-octyl-5-ureidoindolin-7-yl)-2,2-dimethylpropanamide hydrochloride N-(5-Amino-4,6-dimethyl-1-octylindolin-7-yl)-2,2-dimethylpropanamide (500 mg) was dissolved in methylene chloride (5.0 mL), and chlorosulfonyl isocyanate (0.14 mL) was added dropwise at −60° C. The mixture was stirred at the same temperature for 3 hr and 6M hydrochloric acid (0.45 mL) was added. The mixture was stirred at room temperature for 30 min. Water (50 mL) was added to the reaction solution and the mixture was extracted with chloroform (100 mL). The chloroform layer was washed with saturated brine and dried over sodium sulfate. Chloroform was evaporated under reduced pressure and the obtained crystalline residue was recrystallized from a mixture of chloroform-diisopropyl ether to give the title compound as crystals (407 mg).

IR ν (Nujol) cm$^{-1}$; 3510, 3364, 1701, 1672, 1654, 1516. $^1$H-NMR (CDCl$_3$) δ (ppm); 0.87 (3H, br-t), 1.00-1.60 (12H, m), 1.41 (9H, s), 2.04 (3H, s), 2.16 (3H, s), 2.90-3.40 (4H, br), 3.60-4.10 (2H, br), 4.00-5.60 (3H, br), 7.10 (1H, s), 9.35 (1H, br).

Example 8

N-(7-methanesulfonylamino-4,6-dimethylindolin-5-yl)-2,2-dimethylundecanamide (1) The compound (11.0 g) obtained in Example 1 (1) was dissolved in acetic acid (55 mL) and fumed nitric acid (3.7 mL) was added while timely cooling the mixture so that the reaction temperature would not exceed 50° C. After stirring at the same temperature for 30 min, diethyl ether (200 mL) was added, and the mixture was further stirred under ice-cooling for 20 min. The precipitated crystals were collected by filtration to give 1-acetyl-4,6-dimethyl-5-nitroindoline as crystals (10.7 g).

IR ν (Nujol) cm$^{-1}$; 1663, 1520. $^1$H-NMR (CDCl$_3$) δ (ppm); 2.17 (3H, s), 2.24 (3H, s), 2.30 (3H, s), 3.08 (2H, t, J=8.5 Hz), 4.12 (2H, t, J=8.5 Hz), 8.00 (1H, s).

(2) 10% Palladium-carbon (1.4 g) was suspended in methanol (300 mL) and the compound (10.3 g) obtained (1) was added. The mixture was subjected to catalytic hydrogenation at 40° C. and 4 kgf/cm$^2$ for 4 hr. The precipitated crystals were dissolved in chloroform and palladium-carbon was filtered off. The filtrate was concentrated under reduced pressure. Chloroform (50 mL) was added to the obtained residue and the mixture was washed successively with saturated aqueous sodium hydrogencarbonate (125 mL) and saturated brine (100 mL), and dried over sodium sulfate. Chloroform was evaporated under reduced pressure to give 1-acetyl-5-amino-4,6-dimethylindoline as crystals (8.74 g).

IR ν (Nujol) cm$^{-1}$; 1626. $^1$H-NMR (CDCl$_3$) δ (ppm); 2.06 (3H, s), 2.16 (6H, s), 3.03 (2H, t, J=8.5 Hz), 3.42 (2H, br-s), 3.97 (2H, t, J=8.5 Hz), 7.87 (1H, s).

(3) The compound (5.0 g) obtained in (2) was suspended in chloroform (50 mL), and triethylamine (4.4 mL) and 2,2-dimethylundecanoyl chloride (6.4 g) were added under ice-cooling. The mixture was stirred at room temperature for 30 min. Chloroform (50 mL) was added to the reaction mixture and the mixture was washed successively with 5% aqueous citric acid (100 mL) and saturated brine (50 mL) and dried over sodium sulfate. Chloroform was evaporated under reduced pressure to give N-(1-acetyl-4,6-dimethylindolin-5-yl)-2,2-dimethylundecanamide as an oil (10.7 g). The obtained oil (10.7 g) was dissolved in acetic acid (50 mL) and fumed nitric acid (1.5 mL) was added under ice-cooling. The mixture was stirred at room temperature for 1 hr. After the completion of the reaction, water (250 mL) was added and the mixture was stirred for 30 min. The precipitated crystals were collected by filtration and the crystals were dissolved in chloroform (100 mL). The solution was washed with saturated aqueous sodium hydrogencarbonate (100 mL) and saturated brine (50 mL) and dried over sodium sulfate. Chloroform was evaporated under reduced pressure. Diisopropyl ether (50 mL) was added to the obtained crystalline residue and the crystals were collected by filtration to give N-(1-acetyl-4,6-dimethyl-7-nitroindolin-5-yl)-2,2-dimethylundecanamide as crystals (8.73 g).

IR ν (Nujol) cm$^{-1}$; 1659, 1532. $^1$H-NMR (CDCl$_3$) δ (ppm); 0.81-0.93 (3H, m), 1.18-1.72 (22H, m), 2.08 (6H, s), 2.21 (3H, s), 3.04 (2H, t, J=8.0 Hz), 4.14 (2H, t, J=8.0 Hz), 7.21 (1H, br-s).

(4) 10% Palladium-carbon (1.2 g) was suspended in methanol (250 mL) and the compound (8.73 g) obtained in (3) was added. The mixture was subjected to catalytic hydrogenation at 40° C., 4 kgf/cm$^2$ for 24 hr. Palladium-carbon was filtered off, and methanol was evaporated under reduced pressure. Chloroform (50 mL) was added to the obtained residue, washed with saturated aqueous sodium hydrogencarbonate (50 mL) and saturated brine (50 mL) and dried over sodium sulfate. Chloroform was evaporated under reduced pressure. Diisopropyl ether (40 mL) was added to the obtained crystalline residue and the crystals were collected by filtration to give N-(1-acetyl-7-amino-4,6-dimethylindolin-5-yl)-2,2-dimethylundecanamide as crystals (7.49 g).

IR ν (Nujol) cm$^{-1}$; 1643, 1620, 1589, 1512. $^1$H-NMR (CDCl$_3$) δ (ppm); 0.81-0.93 (3H, m), 1.19-1.64 (22H, m), 2.00 (6H, s), 2.21 (3H, s), 2.92 (2H, t, J=8.0 Hz), 4.03 (2H, t, J=8.0 Hz), 4.20-4.90 (2H, br), 6.93 (1H, br-s).

(5) The compound (1.0 g) obtained in (4) was dissolved in methylene chloride (10 mL), and triethylamine (0.37 mL) and methanesulfonyl chloride (0.2 mL) were added under ice-cooling. The mixture was stirred at room temperature for 1 hr. Chloroform (20 mL) was added to the reaction mixture and the mixture was washed successively with 5% aqueous citric acid (20 mL) and saturated brine (20 mL) and dried over sodium sulfate. The solvent was evaporated under reduced pressure to give N-(1-acetyl-7-methanesulfonylamino-4,6-dimethylindolin-5-yl)-2,2-dimethylundecanamide as a powder (1.16 g).

IR ν (Nujol) cm$^{-1}$; 1651, 1645, 1634, 1155. $^1$H-NMR (CDCl$_3$) δ (ppm); 0.81-0.93 (3H, m), 1.18-1.70 (22H, m), 2.08 (3H, s), 2.33 (6H, s), 2.79 (3H, s), 3.04 (2H, t, J=7.5 Hz), 4.15 (2H, t, J=7.5 Hz), 6.96 (1H, br-s), 8.77-8.92 (1H, br).

(6) The compound (1.04 g) obtained in (5) was suspended in methanol (10 ml) and a solution of sodium hydroxide (0.42 g) in water (2.5 mL) was added at room temperature. The mixture was refluxed under nitrogen atmosphere for 18 hr. After allowing to cool, methanol was evaporated. Ethyl acetate (50 mL) was added, and the mixture was washed successively with 5% aqueous citric acid (50 mL), saturated aqueous sodium hydrogencarbonate (50 mL) and saturated brine (50 mL) and dried over sodium sulfate. Ethyl acetate was evaporated under reduced pressure. The obtained residue was dissolved in ethyl acetate (10 mL) with heating and n-hexane (10 mL) was added. The mixture was stood still in a freezer for 1 hr to allow crystallization and the precipitated crystals were collected by filtration to give the title compound as crystals (767 mg).

IR ν (Nujol) cm$^{-1}$; 1636, 1609, 1508, 1151. $^1$H-NMR (CDCl$_3$) δ (ppm); 0.81-0.94 (3H, m), 1.17-1.64 (22H, m), 1.98 (3H, s), 2.02 (3H, s), 2.90-3.00 (5H, m), 3.45 (2H, t, J=8.0 Hz), 3.60-4.40 (1H, br), 6.99 (2H, br-s).

Example 9

N-(7-methanesulfonylamino-1,4,6-trimethylindolin-5-yl)-2,2-dimethylundecanamide (1) N-(1-Acetyl-7-amino-4,6-dimethylindolin-5-yl)-2,2-dimethylundecanamide (5.0 g) was dissolved in chloroform (50 mL) and di-tert-butyl dicarbonate (5.3 g) was added at room temperature. The mixture was stirred at the same temperature for 17 hr. Chloroform was evaporated under reduced pressure and the obtained residue was purified by column chromatography to give N-(1-acetyl-7-tert-butoxycarbonylamino-4,6-dimethylindolin-5-yl)-2,2-dimethylundecanamide as a powder (6.22 g).

$^1$H-NMR (CDCl$_3$) δ (ppm); 0.81-0.93 (3H, m), 1.07-1.77 (31H, m), 2.04 (3H, s), 2.13 (3H, s), 2.30 (3H, s), 3.00 (2H, t, J=7.5 Hz), 4.11 (2H, t, J=7.5 Hz), 6.91 (1H, br-s), 8.20 (1H, br-s).

(2) The compound (6.22 g) obtained in (1) was dissolved in methanol (60 mL), and a solution of sodium hydroxide (2.4 g) in water (15 mL) was added at room temperature. The mixture was refluxed under nitrogen atmosphere for 1.5 hr. After allowing to cool, methanol was evaporated. Chloroform (100 mL) was added to the obtained residue, and the mixture was washed successively with 5% aqueous citric acid (80 mL), saturated aqueous sodium hydrogencarbonate (30 mL) and saturated brine (30 mL) and dried over sodium sulfate. Chloroform was evaporated under reduced pressure. n-Hexane (30 mL) was added to the obtained crystalline residue and the crystals were collected by filtration to give N-(7-tert-butoxycarbonylamino-4,6-dimethylindolin-5-yl)-2,2-dimethylundecanamide as crystals (4.81 g).

IR ν (Nujol) cm$^{-1}$; 1672, 1639, 1543, 1514. $^1$H-NMR (CDCl$_3$) δ (ppm); 0.81-0.94 (3H, m), 1.29-1.77 (31H, m), 1.95 (3H, s), 2.01 (3H, s), 2.50-4.60 (1H, br), 2.96 (2H, t, J=8.0 Hz), 3.58 (2H, t, J=8.0 Hz), 6.13 (1H, br-s), 6.88 (1H, br-s).

(3) The compound (2.03 g) obtained in (2) was dissolved in acetone (20 mL), and potassium carbonate (1.18 g) and methyl iodide (0.4 mL) were added at room temperature under nitrogen atmosphere. The mixture was stirred at the same temperature for 2 hr. 5% Aqueous citric acid (10 mL) was added and acetone was evaporated under reduced pressure. Ethyl acetate (50 mL) was added to the obtained residue and the mixture was washed successively with 5% aqueous citric acid (20 mL) and saturated brine (20 mL) and dried over sodium sulfate. Ethyl acetate was evaporated under reduced pressure and the obtained residue was purified by column chromatography to give N-(7-tert-butoxycarbonylamino-1,4,6-trimethylindolin-5-yl)-2,2-dimethylundecanamide as crystals (1.25 g).

IR ν (Nujol) cm$^{-1}$; 1672, 1639, 1603, 1520. $^1$H-NMR (CDCl$_3$) δ (ppm); 0.80-0.93 (3H, m), 1.28-1.64 (31H, m), 1.96 (3H, s), 1.98 (3H, s), 2.82 (2H, t, J=8.0 Hz), 2.89 (3H, s), 3.33 (2H, t, J=8.0 Hz), 5.96 (1H, br-s), 6.82 (1H, br-s).

(4) The compound (1.23 g) obtained in (3) was dissolved in formic acid (6 mL), and 8.51 M hydrogen chloride—2-propanol solution (1.5 mL) was added under nitrogen atmosphere and under ice-cooling. The mixture was stirred at the same temperature for 15 min, neutralized with saturated aqueous sodium hydrogencarbonate, extracted with chloroform (50 mL), washed with saturated brine (20 mL) and dried over sodium sulfate. Chloroform was evaporated under reduced pressure and the obtained residue was purified by column chromatography. n-Hexane was added to the obtained crystalline residue and the crystals were collected by filtration to give N-(7-amino-1,4,6-trimethylindolin-5-yl)-2,2-dimethylundecanamide as crystals (713 mg).

IR ν (Nujol) cm$^{-1}$; 1641, 1522. $^1$H-NMR (CDCl$_3$) δ (ppm); 0.80-0.93 (3H, m), 1.17-1.66 (22H, m), 2.01 (6H, s), 2.75-2.99 (4H, m), 2.79 (3H, s), 3.37 (2H, t, J=7.5 Hz), 6.80 (1H, br-s).

(5) The compound (703 mg) obtained in (4) was dissolved in methylene chloride (7 mL), and methanesulfonyl chloride (0.18 mL) and triethylamine (1.0 mL) were added under nitrogen atmosphere and under ice-cooling. The mixture was stirred at the same temperature for 10 min. Chloroform (30 mL) was added to the reaction mixture, and the mixture was washed successively with 5% aqueous citric acid (30 mL) twice and saturated brine (20 mL) and dried over sodium sulfate. The solvent was evaporated under reduced pressure and the obtained residue was purified by column chromatography to give the title compound as crystals (510 mg).

IR ν (Nujol) cm$^{-1}$; 1641, 1528, 1148. $^1$H-NMR (CDCl$_3$) δ (ppm); 0.81-0.94 (3H, m), 1.20-1.72 (22H, m), 2.01 (3H, s), 2.13 (3H, s), 2.82-3.03 (2H, m), 2.97 (3H, s), 3.02 (3H, s), 3.43 (2H, t, J=7.5 Hz), 6.13 (1H, br-s), 6.80 (1H, 20 br-s).

Example 10

N-(5-methanesulfonylaminomethyl-4,6-dimethyl-1-octylindolin-7-yl)-2,2-dimethylpropanamide hydrochloride (1) The compound (10.0 g) obtained in Example 1 (4) was dissolved in concentrated hydrochloric acid (50 mL), and 35% formalin (4.2 g) and zinc chloride (900 mg) were added. The mixture was stirred while introducing a hydrogen chloride gas at 50° C. for 2 hr. The reaction solution was poured into ice water (200 mL) and the mixture was extracted twice with chloroform (150 mL). The chloroform layers were combined, washed with saturated brine (150 mL) and dried over sodium sulfate. Chloroform was evaporated under reduced pressure and the obtained N-(1-acetyl-5-chloromethyl-4,6-dimethylindolin-7-yl)-2,2-dimethylpropanamide (10.0 g) was suspended in N,N-dimethylformamide (50 mL). Potassium phthalimide (6.7 g) was added, and the mixture was stirred at room temperature for 20 hr. Ethyl acetate (700 mL) was added, and the mixture was washed with water (500 mL) and saturated brine (300 mL), dried over sodium sulfate and concentrated under reduced pressure. The precipitated crystals were collected by filtration to give N-(1-acetyl-4,6-dimethyl-5-phthalimidomethylindolin-7-yl)-2,2-dimethylpropanamide (12.4 g).

IR ν (Nujol) cm$^{-1}$; 1770, 1708, 1674, 1647. $^1$H-NMR (CDCl$_3$) δ (ppm); 1.25 (9H, s), 2.23 (3H, s), 2.28 (3H, s), 2.36 (3H, s), 2.80-3.30 (2H, br), 3.90-4.30 (2H, br), 4.98 (2H, s), 7.50-7.90 (4H, m), 9.13 (1H, br-s).

(2) The compound (12.0 g) obtained in (1) was dissolved in a mixture of methanol (100 mL) and chloroform (50 mL) and hydrazine monohydrate (2.1 g) was added. The mixture was refluxed for 3 hr. The solvent was evaporated under reduced pressure and the obtained residue was dissolved in chloroform (200 mL). The mixture was washed successively with saturated aqueous sodium hydrogencarbonate (100 mL), saturated brine (100 mL) and dried over sodium sulfate. Chloroform was evaporated under reduced pressure and the obtained N-(1-acetyl-5-aminomethyl-4,6-dimethylindolin-7-yl)-2,2-dimethylpropanamide was dissolved in chloroform (100 mL). Di-tert-butyl dicarbonate (6.0 g) was added, and the mixture was stirred at room temperature for 1 hr, washed with saturated brine (100 mL) and dried over sodium sulfate. Chloroform was evaporated under reduced pressure and the obtained residue was purified by column chromatography to give N-(1-acetyl-5-tert-butoxycarbonylaminomethyl-4,6-dimethylindolin-7-yl)-2,2-dimethylpropanamide as crystals (11.5 g).

IR ν (Nujol) cm$^{-1}$; 1678, 1645, 1514. $^1$H-NMR (CDCl$_3$) δ (ppm); 1.27 (9H, s), 1.44 (9H, s), 2.19 (3H, s), 2.24 (3H, s), 2.30 (3H, s), 2.80-3.30 (2H, br), 3.90-4.30 (2H, br), 4.36 (2H, s), 4.40 (1H, br), 9.12 (1H, br-s).

(3) The compound (11.5 g) obtained in (2) was dissolved in methanol (200 mL) and 2.42 M aqueous sodium hydroxide solution (60 mL) was added. The mixture was stirred at 50° C. for 15 hr. Methanol was evaporated under reduced pressure and the residue was dissolved in chloroform (200 mL). The mixture was washed successively with water (100 mL) and saturated brine (100 mL) and dried over sodium sulfate. Chloroform was evaporated under reduced pressure and the obtained N-(5-tert-butoxycarbonylaminomethyl-4,6-dimethylindolin-7-yl)-2,2-dimethylpropanamide was dissolved in N,N-dimethylformamide (50 mL). Octyl iodide (11.4 g) and potassium carbonate (6.6 g) were added and the mixture was stirred at 40° C. for 15 hr. Ethyl acetate (300 mL) was added, and the mixture was washed successively with water (100 mL) and saturated brine (100 mL) and dried over sodium sulfate. Ethyl acetate was evaporated under reduced pressure and the obtained residue was purified by column chromatography to give N-(5-tert-butoxycarbonylaminomethyl-4,6-dimethyl-1-octylindolin-7-yl)-2,2-dimethylpropanamide as crystals (7.9 g).

IR ν (Nujol) cm$^{-1}$; 1695, 1674, 1649, 1541. $^1$H-NMR (CDCl$_3$) δ (ppm); 0.88 (3H, br-t), 1.10-1.90 (12H, m), 1.34 (9H, s), 1.44 (9H, s), 2.08 (3H, s), 2.16 (3H, s), 2.83 (2H, t, J=8.5 Hz), 3.13 (2H, t, J=7.1 Hz), 3.42 (2H, t, J=8.5 Hz), 4.26 (2H, s), 4.30 (1H, br-s), 6.80 (1H, br-s).

(4) The compound (4.0 g) obtained in (3) was dissolved in chloroform (100 mL), and 8M hydrogen chloride—2-propanol solution (11 mL) was added under ice-cooling. The mixture was stirred at room temperature for 1 hr, washed successively with saturated aqueous sodium hydrogencarbonate (70 mL) and saturated brine (70 mL) and dried over sodium sulfate. Methanesulfonyl chloride (939 mg) and triethylamine (830 mg) were added to the obtained solution under ice-cooling and the mixture was stirred at the same temperature for 30 min, washed successively with 5% aqueous citric acid (70 mL) and saturated brine (70 mL) and dried over sodium sulfate. Chloroform was evaporated under reduced pressure. The obtained residue was purified by column chromatography and the obtained oil (1.5 g) was dissolved in chloroform (30 mL). 8M hydrogen chloride-2-propanol solution (0.48 mL) was added under ice-cooling. chloroform was evaporated under reduced pressure to give the title compound as a powder (1.2 g).

IR ν (Nujol) cm$^{-1}$; 1666. $^1$H-NMR (CDCl$_3$) δ (ppm); 0.79 (3H, br-t), 1.10-1.90 (12H, m), 1.34 (9H, s), 2.18 (3H, s), 2.29 (3H, s), 2.60-3.20 (4H, m), 2.89 (3H, s), 3.40-4.20 (3H, br), 4.29 (2H, s), 4.98 (1H, br-s), 9.34 (1H, br-s).

According to Examples 1 to 10, the compounds of Examples 11 to 45 were synthesized.

Example 11

N-(5-methanesulfonylamino-4,6-dimethyl-1-pentyl-indolin-7-yl)-2,2-dimethylpropanamide IR ν (Nujol) cm$^{-1}$; 3203, 1666, 1510. $^1$H-NMR (CDCl$_3$) δ (ppm); 0.90 (3H, br-t), 1.10-1.80 (6H, m), 1.33 (9H, s), 2.10 (3H, s), 2.15 (3H, s), 2.83 (2H, t, J=8.4 Hz), 2.97 (3H, s), 3.18 (2H, t, J=8.0 Hz), 3.45 (2H, t, J=8.4 Hz), 6.04 (1H, br-s), 6.83 (1H, br-s).

Example 12

N-(1-butyl-5-methanesulfonylamino-4,6-dimethylindolin-7-yl)-2,2-dimethylpropanamide IR ν (Nujol) cm$^{-1}$; 3124, 1652, 1506. $^1$H-NMR (CDCl$_3$) δ (ppm); 0.93 (3H, br-t), 1.10-1.70 (4H, m), 1.33 (9H, s), 2.10 (3H, s), 2.14 (3H, s), 2.83 (2H, t, J=8.4 Hz), 2.97 (3H, s), 3.18 (2H, t, J=8.0 Hz), 3.45 (2H, t, J=8.4 Hz), 6.09 (1H, br-s), 6.84 (1H, br-s).

Example 13

N-[5-methanesulfonylamino-4,6-dimethyl-1-(3-methylbutyl)indolin-7-yl]-2,2-dimethylpropanamide IR ν (Nujol) cm$^{-1}$; 3205, 1666, 1504. $^1$H-NMR (CDCl$_3$) δ (ppm); 0.92 (6H, d, J=6.0 Hz), 1.20-1.60 (3H, m), 1.34 (9H, s), 2.09 (3H, s), 2.14 (3H, s), 2.81 (2H, t, J=8.3 Hz), 2.96 (3H, s), 3.19 (2H, br-t), 3.43 (2H, t, J=8.3 Hz), 6.15 (1H, br-s), 6.86 (1H, br-s).

Example 14

N-(5-methanesulfonylamino-4,6-dimethyl-1-propylindolin-7-yl)-2,2-dimethylpropanamide IR ν (Nujol) cm$^{-1}$; 3205, 1662, 1506. $^1$H-NMR (CDCl$_3$) δ (ppm); 0.90 (3H, t, J=7.2 Hz), 1.30-1.80 (2H, m), 1.34 (9H, s), 2.07 (3H, s), 2.10 (3H, s), 2.81 (2H, t, J=8.4 Hz), 2.95 (3H, s), 3.14 (2H, t, J=7.2 Hz), 3.44 (2H, t, J=8.4 Hz), 6.23 (1H, br-s), 6.88 (1H, br-s).

Example 15

N-[5-methanesulfonylamino-4,6-dimethyl-1-(2-methylpropyl)indolin-7-yl]-2,2-dimethylpropanamide IR ν (Nujol) cm$^{-1}$; 3269, 1658, 1596. $^1$H-NMR (CDCl$_3$) δ (ppm); 0.93 (6H, d, J=6.4 Hz), 1.20-1.60 (1H, m), 1.34 (9H, s), 2.06 (3H, s), 2.09 (3H, s), 2.82 (2H, t, J=8.4 Hz), 2.96 (3H, s), 3.01 (2H, d, J=6.4 Hz), 3.41 (2H, t, J=8.4 Hz), 6.27 (1H, br-s), 6.81 (1H, br-s).

Example 16

N-(1-ethyl-5-methanesulfonylamino-4,6-dimethylindolin-7-yl)-2,2-dimethylpropanamide IR ν (Nujol) cm$^{-1}$; 3197, 1664, 1506. $^1$H-NMR (CDCl$_3$) δ (ppm); 0.94 (3H, t, J=7.0 Hz), 1.21 (9H, s), 1.99 (3H, s), 2.11 (3H, s), 2.77 (2H, br-t), 2.88 (3H, s), 3.19 (2H, br-t), 3.37 (2H, br-t), 8.52 (1H, br-s), 8.67 (1H, br-s).

Example 17

N-(4,6-dimethyl-1-propyl-5-sulfamoylaminoindolin-7-yl)-2,2-dimethylpropanamide hydrochloride IR ν (Nujol) cm$^{-1}$; 3448, 3336, 3240, 3163, 2501, 1674, 1340, 1180, 1163. $^1$H-NMR (DMSO-d$_6$) δ (ppm); 0.86 (3H, t, J=7.4 Hz), 1.30 (9H, s), 1.50-2.00 (2H, m), 2.14 (3H, s), 2.30 (3H, s), 2.90-3.40 (4H, m), 3.60-4.00 (2H, br-t), 5.00-8.00 (3H, br), 8.53 (1H, br-s), 9.32 (1H, br-s).

Example 18

N-(4,6-dimethyl-1-pentyl-5-sulfamoylaminoindolin-7-yl)-2,2-dimethylpropanamide hydrochloride IR ν (Nujol) cm$^{-1}$; 3589, 3471, 3340, 3230, 3138, 2528, 1672, 1340, 1186, 1164. $^1$H-NMR (DMSO-d$_6$) δ (ppm); 0.85 (3H, t, J=5.7 Hz), 1.00-2.00 (6H, m), 1.30 (9H, s), 2.14 (3H, s), 2.30 (3H, s), 2.90-3.40 (4H, m), 3.60-4.00 (2H, br-t), 5.00-8.00 (3H, br), 8.54 (1H, br-s), 9.32 (1H, br-s).

Example 19

N-(1-butyl-4,6-dimethyl-5-sulfamoylaminoindolin-7-yl)-2,2-dimethylpropanamide hydrochloride IR ν (Nujol) cm$^{-1}$; 3456, 3340, 3244, 3136, 2732, 2522, 1674, 1627, 1377, 1338, 1180, 1163. $^1$H-NMR (DMSO-d$_6$) δ (ppm); 0.87 (3H, br-t), 0.90-2.00 (4H, m), 1.30 (9H, s), 2.14 (3H, s), 2.30 (3H, s), 2.90-3.40 (4H, m), 3.60-4.00 (2H, br-t), 4.20-8.20 (3H, br), 8.55 (1H, br-s), 9.33 (1H, br-s).

Example 20

N-[1-(3-methylbutyl)-4,6-dimethyl-5-sulfamoylaminoindolin-7-yl]-2,2-dimethylpropanamide hydrochloride.

IR ν (Nujol) cm$^{-1}$; 3233, 3105, 2472, 2362, 1672, 1629, 1165. $^1$H-NMR (DMSO-d$_6$) δ (ppm); 0.85 (6H, d, J=5.0 Hz), 1.30 (9H, s), 1.30-1.80 (3H, m), 2.14 (3H, s), 2.30 (3H, s), 2.90-3.40 (4H, m), 3.60-4.00 (2H, br), 5.00-8.50 (3H, br), 8.54 (1H, br-s), 9.30 (1H, br-s).

Example 21

N-[1-(2-methylpropyl)-4,6-dimethyl-5-sulfamoylaminoindolin-7-yl]-2,2-dimethylpropanamide hydrochloride IR ν (Nujol) cm$^{-1}$; 3608, 3446, 3342, 3249, 3141, 2729, 2567, 2526, 1668, 1627, 1377, 1338, 1180, 1163. $^1$H-NMR (DMSO-d$_6$) δ (ppm); 0.98 (6H, d, J=5.0 Hz), 1.29 (9H, s), 1.80-2.50 (1H, m), 2.12 (3H, s), 2.29 (3H, s), 2.80-3.40 (4H, m), 3.60-3.90 (2H, br), 5.00-8.00 (3H, br), 8.48 (1H, br-s), 9.27 (1H, br-s).

Example 22

N-(1-hexyl-5-methanesulfonylamino-4,6-dimethylindolin-7-yl)-2,2-dimethylpropanamide IR ν (Nujol) cm$^{-1}$; 3360, 1665. $^1$H-NMR (CDCl$_3$) δ (ppm); 0.88 (3H, br-t), 1.16-1.69 (8H, m), 1.33 (9H, s), 2.10 (3H, s), 2.14 (3H, s), 2.73-3.55 (6H, m), 2.97 (3H, s), 6.09 (1H, br-s), 6.83 (1H, br-s).

Example 23

N-[4,6-dimethyl-7-(2-propanesulfonylamino)indolin-5-yl]-2,2-dimethylundecanamide hydrochloride IR ν (Nujol) cm$^{-1}$; 1647, 1142. $^1$H-NMR (DMSO-d$_6$) δ (ppm); 0.80-0.95 (3H, m), 1.00-1.80 (28H, m), 2.03 (3H, s), 2.14 (3H, s), 3.00-3.80 (5H, m), 3.50-7.50 (2H, br), 8.95 (1H, br-s), 9.29 (1H, br-s).

Example 24

N-[4,6-dimethyl-7-(2-propanesulfonylamino)indolin-5-yl]-2,2-dimethyloctanamide.

IR ν (Nujol) cm$^{-1}$; 1643, 1620. $^1$H-NMR (CDCl$_3$) δ (ppm); 0.80-0.95 (3H, m), 1.00-1.80 (16H, m) 1.40 (6H, d, J=7.0 Hz), 1.97 (3H, s), 2.00 (3H, s), 2.60-3.80 (6H, m), 6.70-7.10 (1H, br), 6.98 (1H, br-s).

Example 25

N-[4,6-dimethyl-7-(p-toluene)sulfonylaminoindolin-5-yl]-2,2-dimethylundecanamide IR ν (Nujol) cm$^{-1}$; 1639, 1165. $^1$H-NMR (CDCl$_3$) δ (ppm); 0.81-0.94 (3H, m), 1.20-1.80 (22H, m), 1.46 (3H, s), 1.94 (3H, s), 2.38 (3H, s), 2.60-4.20 (2H, br), 2.88 (2H, t, J=8.0 Hz), 3.34 (2H, t, J=8.0 Hz), 6.86 (1H, br-s), 7.21 (2H, d, J=8.0 Hz), 7.64 (2H, d, J=8.0 Hz).

Example 26

N-(4,6-dimethyl-7-sulfamoylaminoindolin-5-yl)-2,2-dimethylundecanamide hydrochloride IR ν (Nujol) cm$^{-1}$; 1645, 1159. $^1$H-NMR (DMSO-d$_6$) δ (ppm); 0.80-0.95 (3H, m), 1.10-1.80 (22H, m), 2.03 (3H, s), 2.15 (3H, s), 3.00-3.20 (2H, m), 3.20-7.80 (4H, br), 3.60-3.80 (2H, m), 8.80-9.00 (2H, br-s).

Example 27

N-(4,6-dimethyl-7-ureidoindolin-5-yl)-2,2-dimethylundecanamide

IR ν (Nujol) cm$^{-1}$; 1670, 1638. $^1$H-NMR (CDCl$_3$) δ (ppm); 0.80-0.95 (3H, m), 1.10-1.80 (22H, m), 1.72 (3H, s), 1.88 (3H, s), 2.80-3.80 (5H, m), 5.06 (2H, br-s), 6.70-6.90 (1H, br), 7.35 (1H, br-s).

Example 28

N-[4,6-dimethyl-7-(2-propanesulfonylamino)indolin-5-yl]-cyclohexanecarboxamide

IR ν (Nujol) cm$^{-1}$; 3330, 3204, 1649, 1512, 1377, 1145, 1136. $^1$H-NMR (CDCl$_3$) δ (ppm); 1.20-2.50 (11H, m), 1.40 (6H, d, J=6.8 Hz), 1.96 (6H, s), 2.91 (2H, t, J=8.2 Hz), 3.25 (1H, septet, J=6.8 Hz), 3.49 (2H, t, J=8.2 Hz), 4.74 (1H, br), 6.64 (1H, br), 7.26 (1H, br).

Example 29

N-[4,6-dimethyl-7-(1-octanesulfonylamino)indolin-5-yl]-2,2-dimethylpropanamide

IR ν (Nujol) cm$^{-1}$; 3327, 3165, 1632, 1607, 1510. $^1$H-NMR (CDCl$_3$) δ (ppm); 0.87 (3H, br-t), 1.10-1.60 (12H, m), 1.36 (9H, s), 1.96 (3H, s), 2.03 (3H, s), 2.70-3.20 (4H, m), 3.43 (2H, t, J=8.1 Hz), 4.80 (1H, br), 6.83 (1H, br), 7.00 (1H, br).

Example 30

N-[4,6-dimethyl-7-(2-propanesulfonylamino)indolin-5-yl]-benzamide

IR ν (Nujol) cm$^{-1}$; 1645, 1528, 1138. $^1$H-NMR (DMSO-d$_6$) δ (ppm); 1.31 (6H, d, J=6.5 Hz), 1.98 (3H, s), 2.10 (3H, s), 2.80-3.70 (5H, m), 4.80-5.20 (1H, br), 7.40-7.70 (3H, m), 7.80-8.10 (2H, m), 8.42 (1H, br-s), 9.53 (1H, br-s).

Example 31

N-(5-methanesulfonylamino-1,4,6-trimethylindolin-7-yl)-2,2-dimethylpropanamide

IR ν (Nujol) cm$^{-1}$; 3193, 1662, 1506. $^1$H-NMR (DMSO-d$_6$) δ (ppm); 1.20 (9H, s), 1.98 (3H, s), 2.12 (3H, s), 2.60-3.00 (2H, m), 2.80 (3H, s), 2.87 (3H, s), 3,26 (2H, br-t), 8.53 (1H, s), 8.67 (1H, s).

Example 32

N-(1-butyl-5-methanesulfonylamino-4,6-dimethylindolin-7-yl)-2,2-dimethylpropanamide hydrochloride IR ν (Nujol) cm$^{-1}$; 3184, 3099, 1690, 1510, 1329, 1180, 1155. $^1$H-NMR (CDCl$_3$) δ (ppm); 0.96 (3H, br-t), 1.10-2.30 (5H, m), 1.44 (9H, s), 2.18 (3H, s), 2.21 (3H, s), 2.90-3.40 (4H, m), 3.02 (3H, s), 3.50-4.20 (2H, m), 7.34 (1H, br-s), 9.59 (1H, br-s).

Example 33

N-[5-methanesulfonylamino-4,6-dimethyl-1-(2-methylpropyl)indolin-7-yl]-2,2-dimethylpropanamide hydrochloride IR ν (Nujol) cm$^{-1}$; 3236, 3032, 1692, 1506, 1321, 1175, 1155. $^1$H-NMR (CDCl$_3$) δ (ppm); 0.95-1.35 (6H, m), 1.43 (9H, s), 1.60-2.00 (1H, br), 2.10-2.55 (1H, m), 2.16 (3H, s), 2.19 (3H, s), 2.85-3.40 (4H, m), 3.01 (3H, s), 3.60-4.30 (2H, m), 7.50 (1H, br-s), 9.66 (1H, br-s).

Example 34

N-(5-methanesulfonylamino-4,6-dimethyl-1-pentylindolin-7-yl)-2,2-dimethylpropanamide hydrochloride IR ν (Nujol) cm$^{-1}$; 3211, 3148, 1670, 1508, 1325, 1157. $^1$H-NMR (CDCl$_3$) δ (ppm); 0.91 (3H, br-t), 1.20-2.40 (7H, m), 1.44 (9H, s), 2.18 (3H, s), 2.21 (3H, s), 2.90-3.40 (4H, m), 3.02 (3H, s), 3.60-4.20 (2H, m), 7.36 (1H, br-s), 9.58 (1H, br-s).

Example 35

N-[5-methanesulfonylamino-4,6-dimethyl-1-(3-methylbutyl)indolin-7-yl]-2,2-dimethylpropanamide hydrochloride IR ν (Nujol) cm$^{-1}$; 3219, 3080, 1686, 1666, 1506, 1325, 1157. $^1$H-NMR (CDCl$_3$) δ (ppm); 0.94 (6H, d, J=5.7 Hz), 1.20-2.40 (4H, m), 1.43 (9H, s), 2.18 (3H, s), 2.26 (3H, s), 2.90-3.40 (4H, m), 3.03 (3H, s), 3.60-4.20 (2H, m), 7.12 (1H, br-s), 9.52 (1H, br-s).

Example 36

N-(1-butyl-5-methanesulfonylamino-4,6-dimethylindolin-7-yl)-2,2-dimethylbutanamide IR ν (Nujol) cm$^{-1}$; 3360, 3202, 1661, 1504, 1377, 1321, 1151. $^1$H-NMR (CDCl$_3$) δ (ppm); 0.70-1.10 (6H, m), 1.10-1.90 (6H, m), 1.29 (6H, s), 2.11 (3H, s), 2.13 (3H, s), 2.84 (2H, t, J=8.4 Hz), 2.96 (3H, s), 3.18 (2H, t, J=6.8 Hz), 3.44 (2H, t, J=8.4 Hz), 6.16 (1H, br-s), 6.85 (1H, br-s).

Example 37

N-(1-butyl-5-methanesulfonylamino-4,6-dimethylindolin-7-yl)-2-methylpropanamide

IR ν (Nujol) cm$^{-1}$; 3263, 1657, 1520, 1377, 1310, 1155, 1144. $^1$H-NMR (DMSO-d$_6$) δ (ppm); 0.77-1.90 (7H, m), 1.10 (6H, d, J=6.6 Hz), 1.90-2.35 (1H, m), 2.00 (3H, s), 2.11 (3H, s), 2.40-3.60 (6H, m), 2.89 (3H, s), 8.51 (1H, br-s), 8.93 (1H, br-s).

Example 38

N-(1-isopropyl-5-methanesulfonylamino-4,6-dimethylindolin-7-yl)-2,2-dimethylpropanamide IR ν (Nujol) cm$^{-1}$; 3176, 1656. $^1$H-NMR (CDCl$_3$) δ (ppm); 1.03 (6H, d, J=6.6 Hz), 1.21 (9H, s), 2.00 (3H, s), 2.12 (3H, s), 2.76 (2H, br-t), 2.89 (3H, s), 3.37 (2H, br-t), 4.00-4.20 (1H, m), 8.53 (1H, br-s), 8.70 (1H, br-s).

Example 39

N-[1-(2,2-dimethylpropyl)-5-methanesulfonylamino-4,6-dimethylindolin-7-yl]-2,2-dimethylpropanamide hydrochloride IR ν (Nujol) cm$^{-1}$; 3348, 2467, 2361, 1668, 1319, 1184, 1150. $^1$H-NMR (CDCl$_3$) δ (ppm); 1.21 (9H, s), 1.48 (9H, s), 1.50-1.70 (1H, br), 2.16 (3H, s), 2.26 (3H, s), 3.03 (5H, br-s), 3.10-3.40 (2H, m), 3.80-4.30 (2H, m), 7.27 (1H, br-s), 9.50-7.70 (1H, br).

Example 40

N-(1-cyclobutylmethyl-5-methanesulfonylamino-4,6-dimethylindolin-7-yl)-2,2-dimethylpropanamide IR ν (Nujol) cm$^{-1}$; 3205, 1662. $^1$H-NMR (DMSO-d$_6$) δ (ppm); 1.21 (9H, s), 1.50-2.10 (7H, m), 1.99 (3H, s), 2.11 (3H, s), 2.75 (2H, br-t), 2.88 (3H, s), 3.10-3.60 (4H, m), 8.52 (1H, br-s), 8.63 (1H, br-s).

Example 41

N-(1-cyclopentyl-5-methanesulfonylamino-4,6-dimethylindolin-7-yl)-2,2-dimethylpropanamide IR ν (Nujol) cm$^{-1}$; 3219, 1647. $^1$H-NMR (DMSO-d$_6$) δ (ppm); 1.21 (9H, s), 1.30-1.80 (8H, m), 1.98 (3H, s), 2.10 (3H, s), 2.70 (2H, br-t), 2.77 (3H, s), 3.37 (2H, br-t), 4.20-4.60 (1H, m), 8.51 (1H, br-s), 8.68 (1H, br-s).

Example 42

N-(1-cyclopropylmethyl-5-methanesulfonylamino-4,6-dimethylindolin-7-yl)-2,2-dimethylpropanamide IR ν (Nujol) cm$^{-1}$; 3258, 1655. $^1$H-NMR (DMSO-d$_6$) δ (ppm); 0.10-1.10 (5H, m), 1.21 (9H, s), 1.99 (3H, s), 2.10 (3H, s), 2.78 (2H, t, J=8.1 Hz), 2.78 (3H, s), 3.48 (2H, d, J=6.5 Hz), 3.07 (2H, t, J=8.1 Hz), 8.52 (1H, br-s), 8.68 (1H, br-s).

Example 43

N-(1-cyclopentyl-4,6-dimethyl-5-sulfamoylaminoindolin-7-yl)-2,2-dimethylpropanamide hydrochloride IR ν (Nujol) cm$^{-1}$; 3200, 2480, 1705, 1665, 1502, 1335, 1151. $^1$H-NMR (DMSO-d$_6$) δ (ppm); 1.28 (9H, s), 1.37-1.85 (8H, m), 2.13 (3H, s), 2.27 (3H, s), 3.00-4.00 (3H, br), 3.11 (2H, br-t), 3.78 (2H, br-t), 6.70-7.00 (1H, br), 8.50 (1H, br-s), 9.23 (1H, br-s).

Example 44

N-[5-(N-acetylsulfamoylamino)-4,6-dimethyl-1-propylindolin-7-yl]-2,2-dimethylpropanamide IR ν (Nujol) cm$^{-1}$; 3350, 3080, 1699, 1639, 1514, 1344, 1231, 1159. $^1$H-NMR (DMSO-d$_6$) δ (ppm); 0.82 (3H, t, J=7.1 Hz), 1.21 (9H, s), 1.92 (6H, s), 1.46 (2H, sextet, J=8.1 Hz), 2.04 (3H, s), 2.77 (2H, t, J=8.3 Hz), 3.08 (2H, t, J=8.3 Hz), 3.28-3.39 (2H, m), 8.67 (1H, br-s), 9.26 (1H, br-s), 11.29 (1H, br-s).

Example 45

N-[5-methanesulfonylamino-4,6-dimethyl-1-(3-methyl-2-butenyl)indolin-7-yl]-2,2-dimethylpropanamide IR ν (Nujol) cm$^{-1}$; 3130, 1641, 1600. $^1$H-NMR (DMSO-d$_6$) δ (ppm); 1.19 (9H, s), 1.61 (3H, s), 1.65 (3H, s), 2.00 (3H, s), 2.10 (3H, s), 2.74 (2H, br-t), 2.89 (3H, s), 3.34 (2H, br-t), 3.78 (2H, d, J=6.3 Hz), 5.00-5.30 (1H, m), 8.53 (1H, br-s), 8.69 (1H, br-s).

Example 46

N-[1-(2-ethoxyethyl)-4,6-dimethyl-5-sulfamoylaminoindolin-7-yl]-2,2-dimethylpropanamide hydrochloride (1) N-(4,6-Dimethyl-5-nitroindolin-7-yl)-2,2-dimethylpropanamide (800 mg) was dissolved in N,N-dimethylformamide (8.0 mL) and diisopropylethylamine (0.93 mL) and bromomethyl ethyl ether (0.62 mL) were added under a nitrogen atmosphere. The mixture was stirred at 100° C. for 16 hr. Ethyl acetate (100 mL) was added to the reaction mixture and the mixture was washed successively with 5% aqueous citric acid, water and saturated brine (each 50 mL) and dried over sodium sulfate. The obtained residue was purified by silica gel column chromatography to give N-[1-(2-ethoxyethyl)-4,6-dimethyl-5-nitroindolin-7-yl]-2,2-dimethylpropanamide as crystals (820 mg).

IR ν (Nujol) cm$^{-1}$; 3279, 1651, 1593, 1512. $^1$H-NMR (CDCl$_3$) δ (ppm); 1.16 (3H, t, J=6.8 Hz), 1.31 (9H, s), 2.01 (3H, s), 2.10 (3H, s), 2.70-3.00 (2H, m), 3.40-3.70 (8H, m), 7.97 (1H, br-s).

(2) The compound (800 mg) obtained in (1) was dissolved in methanol (16 mL), and 5% palladium-carbon (200 mg) was added. The mixture was subjected to catalytic hydrogenation at 35° C., 3 kgf/cm$^2$ for 11 hr. Palladium-carbon was filtered off, and the solvent was evaporated under reduced pressure. Diethyl ether (20 mL) was added to the obtained crystalline residue, and the crystals were washed by stirring the mixture and collected by filtration to give N-[5-amino-i-(2-ethoxyethyl)-4,6-dimethylindolin-7-yl]-2,2-dimethylpropanamide as crystals (570 mg).

IR ν (Nujol) cm$^{-1}$; 3273, 1651, 1504, 1481. $^1$H-NMR (CDCl$_3$) δ (ppm); 1.16 (3H, t, J=7.0 Hz), 1.34 (9H, s), 1.90 (3H, s), 2.03 (3H, s), 2.70-3.00 (2H, m), 3.00-3.70 (10H, m), 7.45 (1H, br-s).

(3) tert-Butanol (0.23 mL) was dissolved in methylene chloride (4 mL) and chlorosulfonyl isocyanate (0.21 mL) was added dropwise at −10° C. The mixture was stirred at the same temperature for 20 min. The compound (400 mg) obtained in (2) and triethylamine (0.33 mL) were added, and the mixture was stirred at the same temperature for 15 min. Ethyl acetate (50 mL) was added to the reaction mixture and the mixture was washed successively with 5% aqueous citric acid, 5% aqueous sodium hydrogencarbonate and saturated brine (each 50 mL) and dried over sodium sulfate. The solvent was evaporated under reduced pressure and the obtained residue was purified by silica gel column chromatography to give N-[5-(N-tert-butoxycarbonyl)sulfamoylamino-1-(2-ethoxyethyl)-4,6-dimethylindolin-7-yl]-2,2-dimethylpropanamide (440 mg).

IR ν (Nujol) cm$^{-1}$; 3263, 3103, 1728, 1660, 1597. $^1$H-NMR (CDCl$_3$) δ (ppm); 1.13 (3H, t, J=7.0 Hz), 1.31 (9H, s), 1.49 (9H, s), 2.03 (3H, s), 2.15 (3H, s), 2.70-3.00 (2H, m), 3.30-3.70 (8H, m), 6.47 (1H, br-s), 6.50-8.40 (1H, br), 7.80 (1H, br-s).

(4) The title compound was obtained as crystals (235 mg) by treating in the same manner as in Example 6 using the compound (420 mg) obtained in (3)

IR ν (Nujol) cm$^{-1}$; 3543, 3226, 3115, 1676, 1657, 1630, 1504. $^1$H-NMR (DMSO-d$_6$) δ (ppm); 1.12 (3H, t, J=7.1 Hz), 1.26 (9H, s), 2.11 (3H, s), 2.26 (3H, s), 3.05-3.15 (2H, m), 3.30-3.40 (2H, m), 3.44 (2H, q, J=7.1 Hz), 3.50-5.00 (1H, br), 3.66 (2H, br-t), 3.78 (2H, br-t), 6.50-7.50 (2H, br), 8.46 (1H, br-s), 9.15 (1H, br-s).

Example 47

N-[1-(2-methoxyethyl)-4,6-dimethyl-5-sulfamoylaminoindolin-7-yl]-2,2-dimethylpropanamide hydrochloride IR ν (Nujol) cm$^{-1}$; 3363, 3136, 1680, 1628, 1504, 1339, 1178, 1161, 1126. $^1$H-NMR (DMSO-d$_6$) δ (ppm); 1.25 (9H, s), 2.10 (3H, s), 2.24 (3H, s), 2.96-3.11 (2H, m), 3.27 (3H, s), 3.20-4.40 (8H, m), 6.50-7.10 (1H, br), 8.30-8.50 (1H, br), 8.90-9.10 (1H, m).

Example 48

N-[1-(2-ethoxyethyl)-5-methanesulfonylamino-4,6-dimethylindolin-7-yl]-2,2-dimethylpropanamide IR ν (Nujol) cm$^{-1}$; 3350, 3200, 1663, 1506, 1317, 1190, 1151, 1123, 1109. $^1$H-NMR (CDCl$_3$) δ (ppm); 1.16 (3H, t, J=7.1 Hz), 1.32 (9H, s), 2.10 (3H, s), 2.19 (3H, s), 2.88 (2H, t, J=8.6 Hz), 2.98 (3H, s), 3.49 (2H, q, J=7.1 Hz), 3.50 (2H, t, J=8.6 Hz), 3.47-3.60 (4H, m), 5.70-5.90 (1H, m), 7.87 (1H, br-s).

Example 49

N-[1-(2-methoxyethyl)-5-methanesulfonylamino-4,6-dimethylindolin-7-yl]-2,2-dimethylpropanamide IR ν (Nujol) cm$^{-1}$; 3360, 3200, 1662, 1600, 1505, 1318, 1190, 1151, 1114. $^1$H-NMR (CDCl$_3$) δ (ppm); 1.31 (9H, s), 2.09 (3H, s), 2.17 (3H, s), 2.88 (2H, t, J=8.8 Hz), 2.98 (3H, s), 3.36 (3H, s), 3.43-3.62 (6H, m), 5.78-6.00 (1H, m), 7.73 (1H, br-s).

Example 50

N-(2-methoxymethyl-4,6-dimethyl-1-propyl-5-sulfamoylaminoindolin-7-yl)-2,2-dimethylpropanamide hydrochloride (1) 2-Hydroxymethyl-4,6-dimethylindole (14.5 g) was dissolved in acetic acid (145 mL) and sodium cyanoborohydride (11.6 g) was added in portions at 10° C. The mixture was stirred at the same temperature for 1 hr. A solution of sodium hydroxide (101 g) in water (400 mL) was added dropwise, and the mixture was extracted with ethyl acetate (1 L), washed successively with water and saturated brine (each 500 mL) and dried over sodium sulfate. Ethyl acetate was evaporated under reduced pressure to give 2-hydroxymethyl-4,6-dimethylindoline as an oil (13.8 g). The obtained oil was dissolved in chloroform (138 mL), and acetic anhydride (22 mL) and triethylamine (32.6 mL) were added under ice-cooling. The mixture was stirred at room temperature for 2, days. The reaction mixture was washed successively with 5% aqueous citric acid, water and saturated brine (each 200 mL) and dried over sodium sulfate. Chloroform was evaporated under reduced pressure to give 2-acetoxymethyl-1-acetyl-4,6-dimethylindoline as an oil (18.3 g). The obtained oil was dissolved in methanol (200 mL) and 1M aqueous solution of lithium hydroxide (93 mL) was added under ice-cooling. The mixture was stirred at the same temperature for 30 min. The reaction mixture was adjusted to pH 4 with 2M hydrochloric acid and methanol was evaporated under reduced pressure. Diethyl ether (100 mL) was added to the obtained residue and, after stirring under ice-cooling for 30 min, the precipitated crystals were collected by filtration to give 1-acetyl-2-hydroxymethyl-4,6-dimethylindoline (12.18 g).

IR ν (Nujol) cm$^{-1}$; 3327, 1626, 1589. $^1$H-NMR (CDCl$_3$) δ (ppm); 1.50-2.20 (1H, br), 2.19 (3H, s), 2.31 (3H, s), 2.40 (3H, s), 2.30-2.80 (1H, m), 3.00-3.40 (1H, m), 3.65 (2H, d, J=6.4 Hz), 4.50-5.20 (1H, br), 6.20-8.00 (1H, br), 6.70 (1H, s).

(2) The compound (8.34 g) obtained in (1) was dissolved in N,N-dimethylformamide (83 mL), and sodium hydride (60% oil suspension) (1.39 g) was added in portions under a nitrogen atmosphere and under ice-cooling. The mixture was stirred at room temperature for 10 min and methyl iodide (11.8 mL) was added. The mixture was stirred at 80° C. for 2 hr. Ethyl acetate (500 mL) was added, and the mixture was washed successively with 5% aqueous citric acid, water and saturated brine (each 500 mL) and dried over sodium sulfate. Ethyl acetate was evaporated under reduced pressure and the obtained residue was purified by silica gel column chromatography to give 1-acetyl-2-methoxymethyl-4,6-dimethylindoline as crystals. (3.95 g).

IR ν (Nujol) cm$^{-1}$; 1660, 1597. $^1$H-NMR (CDCl$_3$) δ (ppm); 2.20 (3H, s), 2.31 (6H, s), 2.70-2.90 (1H, m), 3.00-3.20 (1H, m), 3.25-3.35 (1H, m), 3.34 (3H, s), 3.40-3.65 (1H, m), 4.54, 4.98 (1H, br-s, br-s), 6.69 (1H, s), 6.60-6.90, 7.70-7.90 (1H, br, br).

(3) The compound (4.17 g) obtained in (2) was dissolved in chloroform (60 mL), and bromine (1.0 mL) was added dropwise under ice-cooling. The mixture was stirred at the same temperature for 20 min. The reaction solution was washed successively with 5% aqueous sodium hydrogensulfite, 5% aqueous sodium hydrogencarbonate and saturated brine (each 50 mL) and dried over sodium sulfate.

Chloroform was evaporated under reduced pressure to give 1-acetyl-5-bromo-2-methoxymethyl-4,6-dimethylindoline (5.21 g).

IR ν (Nujol) cm$^{-1}$; 1662, 1585. $^1$H-NMR (CDCl$_3$) δ (ppm); 2.31 (6H, s), 2.40 (3H, s), 2.70-3.00 (1H, m), 3.10-3.25 (1H, m), 3.25-3.35 (1H, m), 3.34 (3H, s), 3.35-3.50 (1H, m), 4.50-4.60, 4.80-5.10 (1H, br, br), 6.70-7.00, 7.80-8.00 (1H, br, br).

(4) The compound (5.21 g) obtained in (3) was dissolved in acetic acid (52 mL), and concentrated sulfuric acid (1.78 mL) and fumed nitric acid (1.12 mL) were added at 15° C. The mixture was stirred at the same temperature for 20 min. The reaction solution was poured into ice water (300 mL) and the precipitated crystals were collected by filtration. The obtained crystals were dissolved in chloroform (100 mL) and the solution was washed successively with 5% aqueous sodium hydrogencarbonate and saturated brine and dried over sodium sulfate. Chloroform was evaporated under reduced pressure to give 1-acetyl-5-bromo-2-methoxymethyl-4,6-dimethyl-7-nitroindoline as crystals (5.9 g).

IR ν (Nujol) cm$^{-1}$; 1672, 1537. $^1$H-NMR (CDCl$_3$) δ (ppm); 2.29 (3H, s), 2.37 (3H, s), 2.49 (3H, s), 2.82 (1H, d, J=16.1 Hz), 3.30 (1H, dd, J=16.1, 8.6 Hz), 3.35-3.45 (1H, m), 3.39 (3H, s), 3.49 (1H, dd, J=9.8, 6.8 Hz), 4.55-4.65 (1H, m).

(5) The compound (5.9 g) obtained in (4) was dissolved in methanol (185 mL), and 5% palladium-carbon (1.78 g) was added. The mixture was subjected to catalytic hydrogenation at 35° C., 3 kgf/cm$^2$ for 16 hr. Palladium-carbon was filtered off, and the solvent was evaporated under reduced pressure. Ethyl acetate (50 mL) was added to the obtained crystalline residue and the crystals were washed by stirring the mixture and collected by filtration to give 1-acetyl-7-amino-2-methoxymethyl-4,6-dimethylindoline hydrobromide as crystals (4.95 g). The obtained crystals were dissolved in methylene chloride (50 mL), and pivaloyl chloride (1.94 mL) was added and triethylamine (4.4 mL) was added dropwise under ice-cooling. The mixture was stirred at the same temperature for 1 hr, and the reaction mixture was washed successively with 5% aqueous citric acid, water and saturated brine (each 50 mL) and dried over sodium sulfate. Methylene chloride was evaporated under reduced pressure and the obtained residue was purified by silica gel column chromatography to give N-(1-acetyl-2-methoxymethyl-4,6-dimethylindolin-7-yl)-2,2-dimethylpropanamide (4.87 g).

IR ν (Nujol) cm$^{-1}$; 3253, 1739, 1676, 1647, 1589. $^1$H-NMR (CDCl$_3$) δ (ppm); 1.26 (9H, s), 2.17 (3H, s), 2.19 (3H, s), 2.38 (3H, s), 2.54 (1H, d, J=15.6 Hz), 3.18 (1H, dd, J=15.6, 8.0 Hz), 3.29 (3H, s), 3.30-3.37 (2H, m), 4.55-4.65 (1H, m), 6.88 (1H, s), 8.93 (1H, s).

(6) The compound (1.5 g) obtained in (5) was dissolved in acetic acid (7.5 mL), and concentrated sulfuric acid (0.48 mL) and fumed nitric acid (0.28 mL) were added at 15° C. The mixture was stirred at the same temperature for 20 min. The reaction solution was poured into ice water (150 mL) and the precipitated crystals were collected by filtration. The obtained crystals were dissolved in chloroform (50 mL), washed successively with 5% aqueous sodium hydrogencarbonate and saturated brine (each 50 mL) and dried over sodium sulfate. Chloroform was evaporated under reduced pressure to give N-(1-acetyl-2-methoxymethyl-4,6-dimethyl-5-nitroindolin-7-yl)-2,2-dimethylpropanamide as crystals (1.44 g).

IR ν (Nujol) cm$^{-1}$; 3253, 1684, 1649, 1585, 1520. $^1$H-NMR (CDCl$_3$) δ (ppm); 1.26 (9H, s), 2.13 (3H, s), 2.16 (3H, s), 2.41 (3H, s), 2.62 (1H, d, J=16.1 Hz), 3.26 (1H, dd, J=16.1, 8.3 Hz), 3.30 (3H, s), 3.30-3.40 (2H, m), 4.65-4.70 (1H, m), 8.92 (1H, s).

(7) The compound (1.44 g) obtained in (6) was dissolved in ethanol (14.4 mL), and 2M aqueous sodium hydroxide solution (4.77 mL) was added. The mixture was stirred at 60° C. for 1 hr. The solvent was evaporated under reduced pressure and the obtained residue was dissolved in ethyl acetate (50 mL), washed successively with saturated aqueous sodium hydrogencarbonate and saturated brine (each 50 mL) and dried over sodium sulfate. Ethyl acetate was evaporated under reduced pressure and diisopropyl ether (20 mL) was added to the obtained crystalline residue. The crystals were washed by stirring the mixture and collected by filtration to give N-(2-methoxymethyl-4,6-dimethyl-5-nitroindolin-7-yl)-2,2-dimethylpropanamide as crystals (1.26 g).

IR ν (Nujol) cm$^{-1}$; 3369, 3282, 1639, 1600, 1518. $^1$H-NMR (CDCl$_3$) δ (ppm); 1.35 (9H, s), 2.13 (3H, s), 2.15 (3H, s), 2.74 (1H, dd, J=16.1, 6.4 Hz), 3.12 (1H, dd, J=16.1, 9.5 Hz), 3.35-3.45 (2H, m), 3.40 (3H, s), 4.10-4.20 (1H, m), 4.74 (1H, br-s), 6.99 (1H, s).

(8) The compound (1.25 g) obtained in (7) was dissolved in N,N-dimethylformamide (6.25 mL), and diisopropylethylamine (0.95 mL) and propyl iodide (0.73 mL) were added under a nitrogen atmosphere. The mixture was stirred at 90° C. for 14 hr. Ethyl acetate (50 mL) was added to the reaction mixture and the mixture was washed successively with 5% aqueous citric acid, water and saturated brine (each 50 mL) and dried over sodium sulfate. The obtained residue was purified by silica gel column chromatography to give N-(2-methoxymethyl-4,6-dimethyl-5-nitro-1-propylindolin-7-yl)-2,2-dimethylpropanamide as crystals (840 mg).

IR ν (Nujol) cm$^{-1}$; 3279, 1647, 1591, 1508. $^1$H-NMR (CDCl$_3$) δ (ppm); 0.85 (3H, t, J=7.3 Hz), 1.34 (9H, s), 1.40-1.60 (2H, m), 2.02 (3H, s), 2.10 (3H, s), 2.66 (1H, dd, J=16.6, 5.6 Hz), 3.00-3.10 (1H, m), 3.12 (1H, dd, J=16.6, 10.0 Hz), 3.35-3.45 (2H, m), 3.38 (3H, s), 3.47 (1H, dd, J=9.3, 5.1 Hz), 3.85-3.90 (1H, m), 6.76 (1H, s).

(9) The compound (830 mg) obtained in (8) was dissolved in methanol (16.6 mL) and 5% palladium-carbon (170 mg) was added. The mixture was subjected to catalytic hydrogenation at 30° C., 3 kgf/cm$^2$ for 11 hr. Palladium-carbon was filtered off, and the solvent was evaporated under reduced pressure. To the obtained crystalline residue was added diisopropyl ether (20 mL), and the crystals were washed by stirring the mixture and collected by filtration to give N-(5-amino-2-methoxymethyl-4,6-dimethyl-1-propylindolin-7-yl)-2,2-dimethylpropanamide as crystals (590 mg).

IR ν (Nujol) cm$^{-1}$; 3265, 1652, 1508. $^1$H-NMR (CDCl$_3$) δ (ppm); 0.83 (3H, t, J=7.4 Hz), 1.34 (9H, s), 1.40-1.55 (2H, m), 1.91 (3H, s), 2.04 (3H, s), 2.62 (1H, dd, J=16.1, 3.9 Hz), 2.75-2.85 (1H, m), 2.90-3.00 (1H, m), 3.15-3.25 (2H, m), 3.32 (2H, br-s), 3.36 (3H, s), 3.38-3.44 (1H, m), 3.55-3.65 (1H, m), 6.94 (1H, s).

(10) tert-Butanol (0.295 mL) was dissolved in methylene chloride (7.2 mL) and chlorosulfonyl isocyanate (0.27 mL) was added dropwise at −10° C. The mixture was stirred at the same temperature for 20 min. A solution of the compound (540 mg) obtained in (9) in methylene chloride (7.2 mL) and triethylamine (0.43 mL) were added, and the mixture was stirred at the same temperature for 15 min. Ethyl acetate (50 mL) was added to the reaction mixture and the mixture was washed successively with 5% aqueous citric acid, 5% aqueous sodium hydrogencarbonate and saturated brine (each 50 mL) and dried over sodium sulfate. The solvent was evaporated under reduced pressure and the obtained residue was purified by silica gel column chromatography to give N-[5-(N-tert-butoxycarbonyl)sulfamoylamino-2-methoxymethyl-4,6-dimethyl-1-propylindolin-7-yl]-2,2-dimethylpropanamide (560 mg).

IR ν (Nujol) cm$^{-1}$; 3285, 1728, 1654, 1597. $^1$H-NMR (CDCl$_3$) δ (ppm); 0.83 (3H, d, J=7.4 Hz), 1.33 (9H, s), 1.40-1.60 (2H, m), 1.50 (9H, s), 2.08 (3H, s), 2.17 (3H, s), 2.61 (1H, dd, J=16.3, 6.1 Hz), 2.95-3.05 (1H, m), 3.13 (1H, dd, J=16.3, 10.2 Hz), 3.25-3.30 (1H, m), 3.30-3.35 (1H, m), 3.37 (3H, s), 3.47 (1H, dd, J=9.5, 5.4 Hz), 3.75-3.85 (1H, m), 6.45 (1H, s), 6.84 (1H, s), 7.52 (1H, br-s).

(11) The compound (550 mg) obtained in (10) was dissolved in formic acid (2.2 mL), and 8.7 M hydrogen chloride—2-propanol solution (0.38 mL) was added under ice-cooling. The mixture was stirred at the same temperature for 20 min. Diethyl ether (50 mL) was added and the precipitated crystals were collected by filtration to give the title compound as crystals (330 mg).

IR ν (Nujol) cm$^{-1}$; 3321, 3204, 1649, 1527. $^1$H-NMR (DMSO-d$_6$) δ (ppm); 0.80 (3H, t, J=7.3 Hz), 1.26 (9H, s), 1.40-1.70 (2H, m), 2.09 (3H, s), 2.20 (3H, s), 2.60-2.80 (1H, m), 2.95-3.05 (1H, m), 3.20-3.35 (2H, m), 3.30 (3H, s), 3.40-3.55 (2H, m), 3.50-4.50 (4H, m), 8.20-8.50 (1H, br), 9.00-9.40 (1H, br).

According to Example 50, the compound of Example 51 was synthesized.

Example 51

N-(2-ethoxymethyl-4,6-dimethyl-1-propyl-5-sulfamoylaminoindolin-7-yl)-2,2-dimethylpropanamide hydrochloride IR ν (Nujol) cm$^{-1}$; 3322, 3197, 2789, 2716, 1652, 1532, 1323, 1218, 1197, 1155, 1123. $^1$H-NMR (DMSO-d$_6$) δ (ppm); 0.82 (3H, t, J=7.1 Hz), 1.14 (3H, t, J=7.1 Hz), 1.26 (9H, s), 1.45-1.65 (2H, m), 2.12 (3H, s), 2.21 (3H, s), 2.63-2.78 (1H, m), 2.99 (0.5H, dd, J=10.3, 5.9 Hz), 3.02 (0.5H, dd, J=10.3, 6.4 Hz), 3.20-3.35 (2H, m), 3.50 (2H, d, J=7.1 Hz), 3.50 (2H, q, J=7.1 Hz), 3.50-4.60 (3H, br), 6.60-7.00 (1H, br), 8.20-8.45 (1H, br), 9.05-9.40 (1H, m).

Example 52

N-(1-butyryl-4,6-dimethyl-5-sulfamoylaminoindolin-7-yl)-2,2-dimethylpropanamide (1) N-(4,6-Dimethyl-5-nitroindolin-7-yl)-2,2-dimethylpropanamide (1.0 g) was dissolved in chloroform (10 mL), and triethylamine (0.69 mL) and butyryl chloride (0.52 mL) were added under ice-cooling. The mixture was stirred at the same temperature for 15 min. Ethyl acetate (100 mL) was added to the reaction mixture, and the mixture was washed successively with 5% aqueous citric acid, water and saturated brine (each 100 mL) and dried over sodium sulfate. Ethyl acetate was evaporated under reduced pressure and the obtained residue was purified by silica gel column chromatography to give N-(1-butyryl-4,6-dimethyl-5-nitroindolin-7-yl)-2,2-dimethylpropanamide as crystals (0.94 g).

IR ν (Nujol) cm$^{-1}$; 3194, 1670, 1645, 1583, 1529. $^1$H-NMR (CDCl$_3$) δ (ppm); 1.03 (3H, t, J=7.2 Hz), 1.27 (9H, s), 1.50-2.00 (2H, m), 2.10 (3H, s), 2.15 (3H, s), 2.52 (2H, t, J=7.7 Hz), 2.90-3.20 (2H, m), 4.16 (2H, br-t), 9.05 (1H, b-s).

(2) The compound (0.9 g) obtained in (1) was dissolved in methanol (20 mL), 5% palladium-carbon (200 mg) was added. The mixture was subjected to catalytic hydrogenation at 35° C., 3 kgf/cm$^2$ for 11 hr. Palladium-carbon was filtered off, and the solvent was evaporated under reduced pressure. Diethyl ether (20 mL) was added to the obtained crystalline residue, and the crystals were washed by stirring the mixture and collected by filtration to give N-(5-amino-1-butyryl-4,6-dimethylindolin-7-yl)-2,2-dimethylpropanamide as crystals (0.79 g).

IR ν (Nujol) cm$^{-1}$; 3356, 3192, 1676, 1626, 1593. $^1$H-NMR (CDCl$_3$) δ (ppm); 1.02 (3H, t, J=7.3 Hz), 1.28 (9H, s), 1.50-2.00 (2H, m), 1.97 (3H, s), 2.05 (3H, s), 2.48 (2H, t, J=6.8 Hz), 2.80-3.20 (2H, m), 3.57 (2H, br-s), 3.80-4.20 (2H, m), 9.37 (1H, br-s).

(3) N-[5-(N-tert-Butoxycarbonyl)sulfamoylamino-1-butyryl-4,6-dimethylindolin-7-yl]-2,2-dimethylpropanamide was obtained as crystals (548 mg) by treating in the same manner as in Example, 50 (10) using the compound (400 mg) obtained in (2).

IR ν (Nujol) cm$^{-1}$; 3283, 3141, 1741, 1720, 1676, 1625, 1583. $^1$H-NMR (CDCl$_3$) δ (ppm); 1.02 (3H, t, J=7.6 Hz), 1.26 (9H, s), 1.51(9H, s), 1.50-1.90 (2H, m), 2.19 (3H, s), 2.29 (3H, s), 2.45-2.55 (2H, m), 2.70-2.90, 3.10-3.40 (2H, br, br), 3.95-4.10, 4.15-4.30 (2H, br, br), 6.60 (1H, br-s), 7.50-7.80 (1H, s), 9.19 (1H, s).

(4) The title compound was obtained as crystals (618 mg) by treating in the same manner as in Example 6 using the compound (1.36 g) obtained in (3).

IR ν (Nujol) cm$^{-1}$; 3315, 3217, 1666, 1627, 1583. $^1$H-NMR (DMSO-d$_6$) δ (ppm); 0.96 (3H, t, J=7.3 Hz), 1.17 (9H, s), 1.55-1.70 (2H, m), 2.12 (3H, s), 2.24 (3H, s), 2.45-2.60 (2H, m), 2.75-3.20 (2H, br), 3.80-4.10, 4.20-4.40 (2H, br, br), 6.72 (2H, s), 8.36 (1H, br-s), 9.07 (1H, s).

Example 53

N-(2,4,6-trimethyl-1-propyl-5-sulfamoylaminoindolin-7-yl)-2,2-dimethylpropanamide hydrochloride (1) 1-Acetyl-2,4,6-trimethylindoline was obtained as crystals (520 mg) by treating in the same manner as in Example 1 (1) using 2,4,6-trimethylindole (480 mg).

IR ν (Nujol) cm$^{-1}$; 1653, 1593. $^1$H-NMR (CDCl$_3$) δ (ppm); 1.28 (3H, d, J=6.4 Hz), 2.19 (3H, s), 2.30 (6H, s), 2.40-3.40 (2H, m), 4.52 (1H, br), 6.83 (1H, s), 7.81 (1H, s).

(2) 1-Acetyl-5-bromo-2,4,6-trimethylindoline (10.85 g) was obtained by treating in the same manner as in Example 50 (3) using the compound (8.3 g) obtained in (1).

IR ν (Nujol) cm$^{-1}$; 3651, 1655. $^1$H-NMR (CDCl$_3$) δ (ppm); 1.29 (3H, d, J=6.4 Hz), 2.30 (6H, s), 2.41 (3H, s), 2.47-3.48 (2H, m), 4.54 (1H, br), 7.95 (1H, s).

(3) 1-Acetyl-5-bromo-2,4,6-trimethyl-7-nitroindoline was obtained as crystals (440 mg) by treating in the same manner as in Example 50 (4) using the compound (540 mg) obtained in (2).

IR ν (Nujol) cm$^{-1}$; 1676, 1533. $^1$H-NMR (CDCl$_3$) δ (ppm); 1.37 (3H, d, J=6.6 Hz), 2.23 (3H, s), 2.36 (3H, s), 2.48 (3H, s), 2.48-3.54 (2H, m), 4.48-4.64 (1H, m).

(4) N-(1-Acetyl-2,4,6-trimethylindolin-7-yl)-2,2-dimethylpropanamide (951 mg) was obtained by treating in the same manner as in Example 50 (5) using the compound (1.0 g) obtained in (3).

IR ν (Nujol) cm$^{-1}$; 3242, 1645. $^1$H-NMR (CDCl$_3$) δ (ppm); 1.27 (3H, d, J=6.6 Hz), 1.27 (9H, s), 2.18 (6H, s), 2.30 (3H, s), 2.35-3.45 (2H, m), 4.44-4.59 (1H, m), 6.88 (1H, s), 8.98 (1H, br).

(5) N-(1-Acetyl-2,4,6-trimethyl-5-nitroindolin-7-yl)-2,2-dimethylpropanamide was obtained as crystals (6.68 g) by treating in the same manner as in Example 50 (6) using the compound (6.94 g) obtained in (4).

(6) N-(2,4,6-Trimethyl-5-nitroindolin-7-yl)-2,2-dimethylpropanamide (2.56 g) was obtained by treating in the same manner as in Example 50 (7) using the compound (3.0 g) obtained in (5).

IR ν (Nujol) cm$^{-1}$; 3269, 1643, 1519. $^1$H-NMR (CDCl$_3$) δ (ppm); 1.29 (3H, d, J=6.6 Hz), 1.27 (9H, s), 2.11 (3H, s), 2.12 (3H, s), 2.33 (3H, s), 2.40-3.40 (2H, m), 4.40-4.60 (1H, m), 4.58 (1H, s), 7.03 (1H, s), 8.97 (1H, s).

(7) N-(2,4,6-Trimethyl-5-nitro-1-propylindolin-7-yl)-2,2-dimethylpropanamide as crystals (710 mg) was obtained by treating in the same manner as in Example 50 (8) using the compound (700 mg) obtained in (6).

IR ν (Nujol) cm$^{-1}$; 3274, 1651, 1593, 1512. $^1$H-NMR (CDCl$_3$) δ (ppm); 0.88 (3H, t, J=7.3 Hz), 1.26 (3H, d, J=6.1 Hz), 1.34 (9H, s), 1.40-1.65 (2H, m), 2.03 (3H, s), 2.10 (3H, s), 2.44 (1H, dd, J=16.1, 7.1 Hz), 2.95-3.05 (1H, m), 3.16 (1H, dd, J=16.1, 9.5 Hz), 3.35-3.45 (1H, m), 3.75-3.85 (1H, m), 6.73 (1H, s).

(8) The compound (686 mg) obtained in (7) was dissolved in methanol (15 mL), 5% palladium-carbon (170 mg) was added. The mixture was subjected to catalytic hydrogenation at 30° C., 3 kgf/cm$^2$ for 11 hr. Palladium-carbon was filtered off, and the solvent was evaporated under reduced pressure. Diisopropyl ether (20 mL) was added to the obtained crystalline residue and the crystals were washed by stirring the mixture and collected by filtration to give N-(5-amino-2,4,6-trimethyl-1-propylindolin-7-yl)-2,2-dimethylpropanamide as crystals (513 mg). tert-Butanol (0.18 mL) was dissolved in methylene chloride (1.8 mL) and chlorosulfonyl isocyanate (0.16 mL) was added dropwise at −10° C. The mixture was stirred at the same temperature for 20 min. The crystals (500 mg) obtained earlier and triethylamine (0.26 mL) were added, and the mixture was stirred at the same temperature for 1 hr. Ethyl acetate (50 mL) was added to the reaction mixture and the mixture was washed successively with 5% aqueous citric acid, 5% aqueous sodium hydrogencarbonate and saturated brine (each 50 mL) and dried over sodium sulfate. The solvent was evaporated under reduced pressure and the obtained residue was purified by silica gel column chromatography to give N-[5-(N-tert-butoxycarbonyl)sulfamoylamino-2,4,6-trimethyl-1-propylindolin-7-yl]-2,2-dimethylpropanamide (680 mg).

IR ν (Nujol) cm$^{-1}$; 3283, 3233, 1726, 1651, 1514. $^1$H-NMR (DMSO-d$_6$) δ (ppm); 0.79 (3H, t, J=7.1 Hz), 1.19 (3H, d, J=6.4 Hz), 1.22 (9H, s), 1.30-1.50 (2H, m), 1.43 (9H, s), 1.95 (3H, s), 2.05 (3H, s), 2.25-2.35 (1H, m), 2.85-2.95 (1H, m), 3.00-3.15 (1H, m), 3.20-3.40 (1H, m), 3.60-3.75 (1H, br), 8.65 (1H, s), 9.11 (1H, s), 10.77 (1H, br-s).

(9) The title compound obtained was obtained as crystals (384 mg) by treating in the same manner as in Example 6 using the compound (660 mg) obtained in (8)

IR ν (Nujol) cm$^{-1}$; 3204, 1666, 1504. $^1$H-NMR (DMSO-d$_6$) δ (ppm); 0.83 (3H, t, J=7.1 Hz), 1.29 (9H, s), 1.39 (3H, d, J=6.1 Hz), 1.50-1.90 (2H, m), 2.12 (3H, s), 2.26 (3H, s), 2.65-2.80 (1H, m), 2.95-3.05 (1H, m), 3.20-3.30 (1H, m), 3.35-4.00 (2H, m), 4.15-4.40 (1H, br), 6.50-7.50 (2H, br), 8.49 (1H, br-s), 9.30-9.70 (1H, br).

According to Example 53, the compounds of Examples 54 and 55 were synthesized.

Example 54

N-[1-(2-ethoxyethyl)-2,4,6-trimethyl-5-sulfamoylaminoindolin-7-yl]-2,2-dimethylpropanamide hydrochloride IR ν (Nujol) cm$^{-1}$; 3366, 3279, 1655, 1626, 1522, 1329, 1194, 1157. $^1$H-NMR (DMSO-d$_6$) δ (ppm); 1.12 (3H, t, J=7.1 Hz), 1.26 (9H, s), 1.34 (3H, d, J=5.9 Hz), 2.10 (3H, s), 2.22 (3H, s), 2.50-2.69 (1H, m), 3.16-3.28 (1H, m), 3.28-3.72 (7H, m), 3.72-4.60 (2H, br), 6.40-7.20 (1H, br), 8.25-8.50 (1H, br), 9.10-9.35 (1H, m).

Example 55

N-[1-(2-methoxyethyl)-2,4,6-trimethyl-5-sulfamoylaminoindolin-7-yl]-2,2-dimethylpropanamide hydrochloride IR ν (Nujol) cm$^{-1}$; 3339, 3258, 3180, 3040, 1653, 1624, 1528, 1339, 1165. $^1$H-NMR (DMSO-d$_6$) δ (ppm); 1.25 (9H, s), 1.34 (3H, d, J=6.1 Hz), 2.10 (3H, s), 2.22 (3H, s), 2.50-2.69 (1H, m), 3.15-3.70 (6H, m), 3.26 (3H, s), 3.40-4.70 (2H, br), 6.20-7.20 (1H, br), 8.25-8.50 (1H, br), 9.10-9.35 (1H, m).

Example 56

N-[3-(2-methoxyethyl)-4,6-dimethyl-1-propyl-5-sulfamoylaminoindolin-7-yl]-2,2-dimethylpropanamide hydrochloride (1) 4,6-Dimethyltryptophol (16.53 g) was dissolved in acetic acid (83 mL), and, sodium cyanoborohydride (10.7 g) was added in portions at 10° C. The mixture was stirred at the same temperature for 1 hr. A solution of sodium hydroxide (60 g) in water (200 mL) was added dropwise, and the mixture was extracted with ethyl acetate (1 L), washed successively with water and saturated brine (each 500 mL) and dried over sodium sulfate. Ethyl acetate was evaporated under reduced pressure to give 3-(2-hydroxyethyl)-4,6-dimethylindoline as crystals (16.34 g). The obtained crystal (16.34 g) were dissolved in tetrahydrofuran (160 mL) and di-tert-butyl dicarbonate (22.39 g) was added. The mixture was stirred at room temperature for 2 hr. Tetrahydrofuran was evaporated under reduced pressure and the obtained residue was purified by silica gel column chromatography to give 1-tert-butoxycarbonyl-3-(2-hydroxyethyl)-4,6-dimethylindoline (22.14 g).

IR ν (Nujol) cm$^{-1}$; 3439, 1739, 1705, 1596. $^1$H-NMR (CDCl$_3$) δ (ppm); 1.56 (9H, s), 1.37 (1H, br-s), 1.65-1.77 (1H, m), 1.85-1.95 (1H, m), 2.25 (3H, s), 2.29 (3H, s), 3.30-3.40 (1H, m), 3.70-3.80 (2H, m), 3.80-3.95 (2H, m), 6.60 (1H, s), 7.10-7.70 (1H, br).

(2) The compound (22.1 g) obtained in (1) and methyl iodide (9.47 mL) were dissolved in N,N-dimethylformamide (110 mL), and sodium hydride (60% oil suspension) (3.92 g) was added in portions under ice-cooling. The mixture was stirred at the same temperature for 30 min and ethyl acetate (500 mL) was added. The mixture was washed successively with 5% aqueous citric acid, water and saturated brine (each 500 mL) and dried over sodium sulfate. Ethyl acetate was evaporated under reduced pressure to give 1-tert-butoxycarbonyl-3-(2-methoxyethyl)-4,6-dimethylindoline (22.8 g).

IR ν (Nujol) cm$^{-1}$; 1741, 1705. $^1$H-NMR (CDCl$_3$) δ (ppm); 1.57 (9H, s), 1.60-1.70 (1H, m), 1.90-2.00 (1H, m), 2.24 (3H, s), 2.29 (3H, s), 3.25-3.35 (1H, m), 3.34 (3H, s), 3.35-3.45 (2H, m), 3.80-3.90 (2H, m), 6.60 (1H, s), 7.10-7.70 (1H, br).
(3) The compound (22.7 g) obtained in (2) was dissolved in formic acid (72 mL), and 8.7 M hydrogen chloride—2-propanol solution (29 mL) was added under ice-cooling. The mixture was stirred at the same temperature for 15 min. A mixture (500 mL) of n-hexane-diisopropyl ether (5-1) was added, and an oil was separated. The obtained oil was dissolved in water (500 mL) and the mixture was neutralized with sodium bicarbonate. The mixture was extracted with ethyl acetate (500 mL), successively with water and saturated brine (each 500 mL) and dried over sodium sulfate. Ethyl acetate was evaporated under reduced pressure to give 3-(2-methoxyethyl)-4,6-dimethylindoline as an oil (14.0 g). The obtained oil was dissolved in chloroform (155 mL) and acetic anhydride (10.7 mL) and triethylamine (15.8 mL) were added under ice-cooling. The mixture was stirred at room temperature for 1 hr. The reaction mixture was washed successively with 5% aqueous citric acid, 5% aqueous sodium hydrogencarbonate and saturated brine (each 200 mL) and dried over sodium sulfate. Chloroform was evaporated under reduced pressure and the obtained residue was purified by silica gel column chromatography to give 1-acetyl-3-(2-methoxyethyl)-4,6-dimethylindoline as an oil (19.7 g).
IR ν (Nujol) cm$^{-1}$; 1662, 1593. $^1$H-NMR (CDCl$_3$) δ (ppm); 1.60-1.75 (1H, m), 1.85-2.00 (1H, m), 2.22 (3H, s), 2.25 (3H, s), 2.31 (3H, s), 3.20-3.35 (1H, m), 3.32 (3H, s), 3.35-3.45 (2H, m), 3.85-3.95 (1H, m), 3.95-4.05 (1H, m), 6.68 (1H, s), 7.89 (1H, s).
(4) 1-Acetyl-5-bromo-3-(2-methoxyethyl)-4,6-dimethylindoline (26.7 g) was obtained by treating in the same manner as in Example 50 (3) using the compound (19.6 g) obtained in (3)
IR ν (Nujol) cm$^{-1}$; 1645, 1581. $^1$H-NMR (CDCl$_3$) δ (ppm); 1.60-1.75 (1H, m), 1.85-1.95 (1H, m), 2.21 (3H, s), 2.33 (3H, s), 2.40 (3H, s), 3.32 (3H, s), 3.35-3.50 (3H, m), 3.90-4.10 (2H, m), 8.00 (1H, s).
(5) 1-Acetyl-5-bromo-3-(2-methoxyethyl)-4,6-dimethyl-7-nitroindoline was obtained as crystals (19.4 g) by treating in the same manner as in Example 50 (4) using-the compound (26.6 g) obtained in (4).
IR ν (Nujol) cm$^{-1}$; 1737, 1681, 1533. $^1$H-NMR (CDCl$_3$) δ (ppm); 1.65-1.75 (1H, m), 1.80-1.90 (1H, m), 2.23 (3H, s), 2.39 (3H, s), 2.48 (3H, s), 3.25-3.45 (3H, m), 3.30 (3H, s), 4.10-4.20 (2H, m).
(6) N-[1-Acetyl-3-(2-methoxyethyl)-4,6-dimethylindolin-7-yl]-2,2-dimethylpropanamide (9.09 g) was obtained by treating in the same manner as in Example 50 (5) using the compound (10 g) obtained in (5).
IR ν (Nujol) cm$^{-1}$; 3234, 1668, 1641, 1585. $^1$H-NMR (CDCl$_3$) δ (ppm); 1.27 (9H, s), 1.65-1.80 (1H, m), 1.85-1.95 (1H, m), 2.18 (3H, s), 2.21 (3H, s), 2.28 (3H, s), 3.15-3.25 (1H, m), 3.29 (3H, s), 3.30-3.35. (1H, m), 3.35-3.45 (1H, m), 4.05-4.15 (2H, m), 6.88 (1H, s), 9.07 (1H, br-s).
(7) N-[1-Acetyl-3-(2-methoxyethyl)-4,6-dimethyl-5-nitroindolin-7-yl]-2,2-dimethylpropanamide as crystals (10.96 g) was obtained by treating in the same manner as in Example 50 (6) using the compound (9.0 g) obtained in (6).
IR ν (Nujol) cm$^{-1}$; 3219, 1683, 1649, 1583, 1529. $^1$H-NMR (CDCl$_3$) δ (ppm); 1.27 (9H, s), 1.70-1.80 (1H, m), 1.85-1.95 (1H, m), 2.11 (3H, s), 2.22 (3H, s), 2.31 (3H, s), 3.20-3.35 (2H, m), 3.28 (3H, s), 3.40-3.45 (1H, m), 4.05-4.25 (2H, m), 9.09 (1H, br-s).
(8) N-[3-(2-Methoxyethyl)-4,6-dimethyl-5-nitroindolin-7-yl]-2,2-dimethylpropanamide was obtained as crystals (6.08 g) by treating in the same manner as in Example 50 (7) using the compound (9.3 g) obtained in (7).
IR ν (Nujol) cm$^{-1}$; 3420, 3282, 1647, 1610, 1595. $^1$H-NMR (CDCl$_3$) δ (ppm); 1.35 (9H, s), 1.70-1.90 (2H, m), 2.14 (3H, s), 2.22 (3H, s), 3.34 (3H, s), 3.35-3.50 (4H, m), 3.69 (1H, d, J=9.5 Hz), 4.49 (1H, br-s), 7.03 (1H, br-s).
(9) N-[3-(2-Methoxyethyl)-4,6-dimethyl-5-nitro-1-propylindolin-7-yl]-2,2-dimethylpropanamide was obtained as crystals (1.44 g) by treating in the same manner as in Example 50 (8) using the compound (1.5 g) obtained in (8).
IR ν (Nujol) cm$^{-1}$; 3271, 1651, 1591, 1514. $^1$H-NMR (CDCl$_3$) δ (ppm); 0.91 (3H, t, J=7.3 Hz), 1.34 (9H, s), 1.45-1.60 (2H, m), 1.65-1.75 (1H, m), 1.75-1.85 (1H, m), 2.03 (3H, s), 2.17 (3H, s), 3.05-3.15 (1H, m), 3.25-3.50 (5H, m), 3.33 (3H, s), 3.52 (1H, t, J=9.3 Hz), 6.76 (1H, br-s).
(10) N-[5-Amino-3-(2-methoxyethyl)-4,6-dimethyl-1-propylindolin-7-yl]-2,2-dimethylpropanamide was obtained as crystals (1.3 g) by treating in the same manner as in Example 50 (9) using the compound (1.4 g) obtained in (9).
$^1$H-NMR (CDCl$_3$) δ (ppm); 0.89 (3H, t, J=7.3 Hz), 1.35 (9H, s), 1.45-1.60 (2H, m), 1.50-2.00 (2H, m), 1.60-1.70 (1H, m), 1.80-1.90 (1H, m), 1.93 (3H, s), 2.10 (3H, s), 2.75-2.85 (1H, m), 3.10-3.20 (1H, m), 3.20-3.30 (2H, m), 3.35 (3H, s), 3.35-3.50 (3H, m), 6.93 (1H, br-s).
(11) N-[5-(N-tert-Butoxycarbonyl)sulfamoylamino-3-(2-methoxyethyl)-4,6-dimethyl-1-propylindolin-7-yl]-2,2-dimethylpropanamide (1.77 g) was obtained by treating in the same manner as in Example 50 (10) using the compound (1.25 g) obtained in (10).
IR ν (Nujol) cm$^{-1}$; 3294, 1728, 1655, 1595. $^1$H-NMR (CDCl$_3$) δ (ppm); 0.90 (3H, t, J=7.3 Hz), 1.33 (9H, s) 1.40-1.80 (4H, m), 1.50 (9H, s), 2.09 (3H, s), 2.24 (3H, s), 2.95-3.05 (1H, m), 3.20-3.50 (6H, m), 3.33 (3H, s), 6.47 (1H, s), 6.87 (1H, s).
(12) The title compound was obtained as crystals (1.08 g) by treating in the same manner as in Example 6 using the compound (1.7 g) obtained in (11).
IR ν (Nujol) cm$^{-1}$; 3280, 3093, 1678. $^1$H-NMR (DMSO-d$_6$) δ (ppm); 0.87 (3H, t, J=7.3 Hz), 1.27 (9H, s), 1.60-1.80 (3H, m), 1.90-2.00 (1H, m), 2.12 (3H, s), 2.31 (3H, s), 3.00-3.10 (1H, m), 3.20-3.30 (1H, m), 3.27 (3H, s), 3.30-3.80 (5H, m), 6.50-7.50 (2H, m), 8.45 (1H, br-s), 9.16 (1H, br-s).

Example 57

N-(4,6-dimethyl-2-methylthiomethyl-1-propyl-5-sulfamoylaminoindolin-7-yl)-2,2-dimethylpropanamide hydrochloride (1) 4,6-Dimethyl-2-hydroxymethylindole (14.5 g) was dissolved in acetic acid (145 mL) and sodium cyanoborohydride (11.6 g) was added in portions at 10° C. The mixture was stirred at the same temperature for 1 hr. A solution of sodium hydroxide (101 g) in water (400 mL) was added dropwise and the mixture was extracted with ethyl acetate (1 L). The extract was washed successively with water and saturated brine (each 500 mL) and dried over sodium sulfate. Ethyl acetate was evaporated under reduced pressure to give 2-hydroxymethyl-4,6-dimethylindoline as an oil (13.8 g). The obtained oil was dissolved in chloroform (138 mL), and acetic anhydride (22 mL) and triethylamine (32.6 mL) were added under ice-cooling. The mixture was stirred at room temperature for 2 days. The reaction mixture was washed successively with 5% aqueous citric acid, water and saturated brine (each 200 mL) and dried over sodium sulfate. Chloroform was evaporated under reduced pressure to give 2-acetoxymethyl-1-acetyl-4,6-dimethylindoline as an oil (18.3 g).

$^1$H-NMR (CDCl$_3$) δ (ppm); 2.00 (3H, s), 2.19 (3H, s), 2.31 (3H, s), 2.36 (3H, s), 2.70 (1H, d, J=16.0 Hz), 3.15 (1H, dd, J=16.0, 8.6 Hz), 3.80-4.30 (2H, m), 4.40-5.20 (1H, m), 6.69 (1H, s), 7.40-8.00 (1H, br).

(2) 2-Acetoxymethyl-1-acetyl-5-bromo-4,6-dimethylindoline (9.46 g) was obtained by treating in the same manner as in Example 50

(3) using the compound (7.43 g) obtained in (1).

IR ν (Nujol) cm$^{-1}$; 1747, 1660, 1651. $^1$H-NMR (CDCl$_3$) δ (ppm); 1.95 (0.9H, br-s), 2.06 (2.1H, br-s), 2.31 (3H, s), 2.35 (3H, s), 2.41 (3H, s), 2.70-2.90 (1H, m), 3.10-3.30 (1H, m), 3.90 (0.6H, br-s), 4.19 (1.4H, br-s), 4.62 (0.7H, br-s), 4.90-5.20 (0.3H, br), 6.80-7.00 (0.3H, br), 7.91 (0.7H, br-s).

(3) 2-Acetoxymethyl-1-acetyl-5-bromo-4,6-dimethyl-7-nitroindoline was obtained as crystals (10.04 g) by treating in the same manner as in Example 50 (4) using the-compound (9.34 g) obtained in (2).

IR ν (Nujol) cm$^{-1}$; 1744, 1672, 1537. $^1$H-NMR (CDCl$_3$) δ (ppm); 2.09 (3H, s), 2.31 (3H, s), 2.38 (3H, s), 2.50 (3H, s), 2.81 (1H, d, J=16.1 Hz), 3.31 (1H, dd, J=16.1, 8.6 Hz), 4.00 (1H, dd, J=11.5, 7.1 Hz), 4,26 (1H, dd, J=11.5, 6.8 Hz), 4.70-4.80 (1H, m).

(4) N-(2-Acetoxymethyl-1-acetyl-4,6-dimethylindolin-7-yl)-2,2-dimethylpropanamide (7.7 g) was obtained by treating in the same manner as in Example 50 (5) using the compound (10.0 g) obtained in (3).

IR ν (Nujol) cm$^{-1}$; 3265, 1740, 1674, 1639, 1587. $^1$H-NMR (CDCl$_3$) δ (ppm); 1.26 (9H, s), 2.01 (3H, s), 2.18 (3H, s), 2.19 (3H, s), 2.38 (3H, s), 2.65 (1H, d, J=15.9 Hz), 3.25 (1H, dd, J=15.9, 8.3 Hz), 4.00-4.15 (2H, m), 4.60-4.70 (1H, m), 6.90 (1H, s), 8.84 (1H, br-s).

(5) N-(2-Acetoxymethyl-1-acetyl-4,6-dimethyl-5-nitroindolin-7-yl)-2,2-dimethylpropanamide was obtained as crystals (7.92 g) by treating in the same manner as in Example 50 (6) using the compound (7.7 g) obtained in (4).

IR ν (Nujol) cm$^{-1}$; 3284, 1735, 1685, 1639, 1585. $^1$H-NMR (CDCl$_3$) δ (ppm); 1.26 (9H, s), 1.99 (3H, s), 2.12 (3H, s), 2.18 (3H, s), 2.41 (3H, s), 2.65 (1H, d, J=15.9 Hz), 3.34 (1H, dd, J=15.9, 8.0 Hz), 4.12 (2H, d, J=6.3 Hz), 4.65-4.75 (1H, m), 8.82 (1H, b-s).

(6) The compound (7.87 g) obtained in (5) was dissolved in methanol (79 mL), and 1M aqueous solution of lithium hydroxide (29.1 mL) was added under ice-cooling. The mixture was stirred at the same temperature for 30 min. Chloroform (300 mL) was added to the reaction mixture and the mixture was washed successively with 10% aqueous citric acid, saturated aqueous sodium hydrogencarbonate and saturated brine (each 300 mL) and dried over sodium sulfate. Chloroform was evaporated under reduced pressure to give N-(2-hydroxymethyl-4,6-dimethyl-5-nitroindolin-7-yl)-2,2-dimethylpropanamide as crystals (5.7 g).

IR ν (Nujol) cm$^{-1}$; 3273, 1651, 1597, 1515. $^1$H-NMR (CDCl$_3$) δ (ppm); 1.36 (9H, s), 2.14 (3H, s), 2.15 (3H, s), 2.40-2.50 (1H, m), 2.80 (1H, dd, J=16.1, 5.6 Hz), 3.12 (1H, dd, J=16.1, 9.5 Hz), 3.50-3.60 (1H, m), 3.68 (1H, dd, J=11.2, 4.2 Hz), 4.05-4.15 (1H, m), 4.70 (1H, br-s), 7.12 (1H, br-s).

(7) The compound (5.34 g) obtained in (6) was dissolved in N,N-dimethylformamide (26 mL), and diisopropylethylamine (8.48 mL) and propyl iodide (6.48 mL) were added under a nitrogen atmosphere. The mixture was stirred at 110° C. for 13 hr. Ethyl acetate (200 mL) was added to the reaction mixture and the mixture was washed successively with 5% aqueous citric acid, water and saturated brine (each 200 mL) and-dried over sodium sulfate. Ethyl acetate was evaporated under reduced pressure and the obtained residue was purified by silica gel column chromatography to give N-(2-hydroxymethyl-4,6-dimethyl-5-nitro-1-propylindolin-7-yl)-2,2-dimethylpropanamide (3.72 g).

IR ν (Nujol) cm$^{-1}$; 3307, 1739, 1651, 1591, 1506. $^1$H-NMR (CDCl$_3$) δ (ppm); 0.85 (3H, t, J=7.3 Hz), 1.35 (9H, s), 1.40-1.55 (2H, m), 2.07 (3H, s), 2.12 (3H, s), 2.76 (1H, dd, J=16.1, 4.4 Hz), 2.85-3.00 (2H, m), 3.10-3.30 (2H, m), 3.40-3.50 (1H, m), 3.70-3.90 (2H, m), 6.94 (1H, b-s).

(8) The compound (3.7 g) obtained in (7) was dissolved in chloroform (37 mL), and methanesulfonyl chloride (1.57 mL) and triethylamine (2.84 mL) were added under ice-cooling. The mixture was stirred at the same temperature for 30 min. The reaction mixture was washed successively with 10% aqueous citric acid, saturated aqueous sodium hydrogencarbonate and saturated brine (each 50 mL) and dried over sodium sulfate. Chloroform was evaporated under reduced pressure and the obtained residue was purified by silica gel column chromatography to give N-(2-methanesulfonyloxymethyl-4,6-dimethyl-5-nitro-1-propylindolin-7-yl)-2,2-dimethylpropanamide as an oil (1.82 g). The obtained oil was dissolved in N,N-dimethylformamide (36 mL), and potassium thioacetate (942 mg) was added. The mixture was stirred at 70° C. for 1 hr. Ethyl acetate (200 mL) was added to the reaction mixture and the mixture was washed successively with water and saturated brine (each 200 mL) and dried over sodium sulfate. Ethyl acetate was evaporated under reduced pressure to give N-(2-acetylthiomethyl-4,6-dimethyl-5-nitro-1-propylindolin-7-yl)-2,2-dimethylpropanamide (1.39 g).

IR ν (Nujol) cm$^{-1}$; 3319, 1695, 1651, 1593, 1512. $^1$H-NMR (CDCl$_3$) δ; (ppm); 0.87 (3H, t, J=7.3 Hz), 1.34 (9H, s), 1.40-1.60 (2H, m), 2.03 (3H, s), 2.10 (3H, s), 2.37 (3H, s), 2.55 (1H, dd, J=16.4, 4.9 Hz), 2.85 (1H, dd, J=13.7, 7.8 Hz), 3.00-3.10 (1H, m), 3.20 (1H, dd, J=16.4, 10.0 Hz), 3.24 (1H, dd, J=13.7, 4.1 Hz), 3.30-3.40 (1H, m), 3.80-3.90 (1H, m), 6.76 (1H, br-s).

(9) The compound (690 mg) obtained in (8) was dissolved in methanol (20.7 mL), and 1M aqueous sodium hydroxide solution (1.96 mL) was added under ice-cooling. The mixture was stirred at the same temperature for 1 hr. Ethyl acetate (100 mL) was added to the reaction mixture and the mixture was washed successively with water and saturated brine (each 100 mL) and dried over sodium sulfate. Ethyl acetate was evaporated under reduced pressure to give N-(2-mercaptomethyl-4,6-dimethyl-5-nitro-1-propylindolin-7-yl)-2,2-dimethylpropanamide (570 mg).

IR ν (Nujol) cm$^{-1}$; 3288, 1651, 1593, 1516. $^1$H-NMR (CDCl$_3$) δ (ppm); 0.86 (3H, t, J=7.3 Hz), 1.34 (9H, s), 1.40-1.65 (2H, m), 1.50-1.80 (1H, br), 2.04 (3H, s), 2.12 (3H, s), 2.60-2.75 (2H, m), 2.79 (1H, dd, J=16.6, 5.2 Hz), 2.90-3.00 (1H, m), 3.21 (1H, dd, J=16.6, 10.0 Hz), 3.30-3.40 (1H, m), 3.85-3.95 (1H, m), 6.77 (1H, br-s).

(10) The compound (550 mg) obtained in (9) was dissolved in N,N-dimethylformamide (5.5 mL), and diisopropylethylamine (0.32 mL) and methyl iodide (0.12 mL) were added under a nitrogen atmosphere. The mixture was stirred at room temperature for 30 min. Ethyl acetate (50 mL) was added to the reaction mixture and the mixture was washed successively with water and saturated brine (each 50 mL) and dried over sodium sulfate. Ethyl acetate was evaporated under reduced pressure to give N-(4,6-dimethyl-2-methylthiomethyl-5-nitro-1-propylindolin-7-yl)-2,2-dimethylpropanamide (530 mg).

IR ν (Nujol) cm$^{-1}$; 3304, 1651, 1593, 1514. $^1$H-NMR (CDCl$_3$) δ (ppm); 0.87 (3H, t, J=7.3 Hz), 1.34 (9H, s), 1.40-

1.60 (2H, m), 2.02 (3H, s), 2.12 (3H, s), 2.16 (3H, s), 2.57 (1H, dd, J=12.7, 8.6 Hz), 2.70-2.80 (2H, m), 2.95-3.05 (1H, m), 3.23 (1H, dd, J=16.4, 9.7 Hz), 3.35-3.45 (1H, m), 3.80-3.90 (1H, m), 6.77 (1H, br-s).

(11) N-[5-(N-tert-Butoxycarbonyl)sulfamoylamino-4,6-dimethyl-2-methylthiomethyl-1-propylindolin-7-yl]-2,2-dimethylpropanamide (430 mg) was obtained by treating in the same manner as in Example 53 (8) using the compound (520 mg) obtained in (10).

IR ν (Nujol) cm$^{-1}$; 3242, 1728, 1651, 1597, 1514. $^1$H-NMR (DMSO-d$_6$) δ (ppm); 0.85 (3H, t, J=7.3 Hz), 1.33 (9H, s), 1.50 (9H, s), 1.70-1.90 (2H, m), 2.09 (3H, s), 2.16 (3H, s), 2.19 (3H, s), 2.55 (1H, dd, J=12.7, 8.8 Hz), 2.69 (1H, dd, J=16.4, 4.9 Hz), 2.75 (1H, dd, J=12.7, 4.2 Hz), 2.90-3.00 (1H, m), 3.20-3.35 (2H, m), 3.70-3.80 (1H, m), 6.53 (1H, s), 6.89 (1H, s), 7.85-8.15 (1H, br).

(12) The title compound was obtained as crystals (327 mg) by treating in the same manner as in Example 6 using the compound (410 mg) obtained in (11).

IR ν (Nujol) cm$^{-1}$; 3155, 1657, 1504, 1344, 1194, 1161. $^1$H-NMR (DMSO-d$_6$) δ (ppm); 0.81 (3H, t, J=7.3 Hz), 1.26 (9H, s), 1.42-1.70 (2H, m), 2.08 (3H, s), 2.14 (3H, s), 2.21 (3H, s), 2.57 (1H, dd, J=13.7, 8.8 Hz), 2.73-2.87 (1H, m), 2.89-3.06 (2H, m), 3.20-4.40 (2H, br), 3.22-3.37 (2H, m), 4.00-4.15 (1H, m), 5.80-7.40 (1H, m), 8.20-8.40 (1H, br), 9.00-9.20 (1H, br).

Example 58

N-[1-(6-hydroxyhexyl)-4,6-dimethyl-5-sulfamoylaminoindolin-7-yl]-2,2-dimethylpropanamide hydrochloride (1) N-(4,6-Dimethyl-5-nitroindolin-7-yl)-2,2-dimethylpropanamide (3.15 g) was dissolved in N,N-dimethylformamide (30 mL) and diisopropylethylamine (2.2 mL) and 6-bromo-1-hexanol (1.7 mL) were added under a nitrogen atmosphere. The mixture was stirred at 100° C. for 14 hr. Ethyl acetate (200 mL) was added to the reaction mixture, and the mixture was washed successively with 5% aqueous citric acid, water and saturated brine (each 100 mL) and dried over sodium sulfate. Ethyl acetate was evaporated under reduced pressure and the obtained residue was purified by silica gel column chromatography to give N-[1-(6-hydroxyhexyl)-4,6-dimethyl-5-nitroindolin-7-yl]-2,2-dimethylpropanamide as crystals (1.6 g).

$^1$H-NMR (CDCl$_3$) δ (ppm); 1.25-1.45 (4H, m), 1.33 (9H, s), 1.45-1.60 (4H, m), 2.02 (3H, s), 2.11 (3H, s), 2.90 (2H, t, J=9.0 Hz), 3.24 (2H, t, J=7.6 Hz), 3.54 (2H, t, J=8.8 Hz), 3.60-3.70 (2H, m), 6.83 (1H, s).

(2) The compound (1.57 g) obtained in (1) was dissolved in N,N-dimethylformamide (8 mL) and imidazole (600 mg) and tert-butyldimethylsilyl chloride (664 mg) were added. The mixture was stirred at room temperature for 0.5 hr. Ethyl acetate (200 mL) was added to the reaction mixture, and the mixture was washed successively with water and saturated brine (each 100 mL) and dried over sodium sulfate. Ethyl acetate was evaporated under reduced pressure and the obtained residue was purified by silica gel column chromatography to give N-[1-(6-tert-butyldimethylsilyloxyhexyl)-4,6-dimethyl-5-nitroindolin-7-yl]-2,2-dimethylpropanamide (1.89 g).

IR ν (Nujol) cm$^{-1}$; 3290, 1647, 1593, 1508. $^1$H-NMR (CDCl$_3$) δ (ppm); 0.05 (6H, s), 0.85 (9H, s), 1.10-1.70 (8H, m), 1.29 (9H, s), 1.98 (3H, s), 2.06 (3H, s), 2.70-3.00 (2H, m), 3.10-3.30 (2H, m), 3.30-3.70 (4H, m), 6.70 (1H, s).

(3) The compound (1.85 g) obtained in (2) was dissolved in methanol (40 mL), and 5% palladium-carbon (370 mg) was added. The mixture was subjected to catalytic hydrogenation at 35° C., 3 kgf/cm$^2$ for 11 hr. Palladium-carbon was filtered off, and the solvent was evaporated under reduced pressure. Diethyl ether (20 mL) was added to the obtained crystalline residue, and the crystals were washed by stirring the mixture and collected by filtration to give N-(5-amino-1-(6-tert-butyldimethylsilyloxyhexyl)-4,6-dimethylindolin-7-yl)-2,2-dimethylpropanamide as crystals (1.60 g).

IR ν (Nujol) cm$^{-1}$; 3284, 1657, 1506. $^1$H-NMR (CDCl$_3$) δ (ppm); 0.05 (6H, s), 0.90 (9H, s), 1.10-1.70 (8H, m), 1.35 (9H, s), 1.93 (3H, s), 2.06 (3H, s), 2.70-3.10 (4H, m), 3.00-3.80 (2H, br), 3.20-3.50 (2H, m), 3.50-3.70 (2H, m), 6.92 (1H, s)

(4) N-[5-(N-tert-Butoxycarbonyl)sulfamoylamino-1-(6-tert-butyldimethylsilyloxyhexyl)-4,6-dimethylindolin-7-yl]-2,2-dimethylpropanamide (440 mg) was obtained by treating in the same manner as in Example 5 using the compound (400 mg) obtained in (3).

IR ν (Nujol) cm$^{-1}$; 3371, 3184, 1755, 1657, 1512. $^1$H-NMR (CDCl$_3$) δ (ppm); 0.04 (6H, s), 0.81 (9H, s), 1.20-1.45 (4H, m), 1.38 (9H, s), 1.40-1.70 (4H, m), 1.52 (9H, s), 2.06 (3H, s), 2.17 (3H, s), 2.83 (2H, t, J=8.3 Hz), 3.16 (2H, t, J=7.6 Hz), 3.40-3.50 (2H, m), 3.58 (2H, t, J=6.6 Hz), 6.46 (1H, s), 6.92 (1H, s). 7.70-7.80 (1H, br).

(5) The title compound was obtained as crystals (650 mg) by treating in the same manner as in Example 6 using the compound (1.35 g) obtained in (4).

IR ν (Nujol) cm$^{-1}$; 3379, 3244, 3117, 1703, 1682, 1508. $^1$H-NMR (DMSO-d$_6$) δ (ppm); 1.20-1.40 (4H, m), 1.28 (9H, s), 1.50-1.60 (2H, m), 1.60-1.75 (2H, br), 2.13 (3H, s), 2.28 (3H, s), 3.05-3.25 (4H, m), 3.30-4.30 (1H, br), 3.70-3.85 (2H, m), 4.06 (2H, t, J=6.4 Hz), 6.70-7.00 (2H, br), 8.19 (1H, s), 8.53 (1H, s), 9.24 (1H, s).

According to Example 57, the compound of Example 59 was synthesized.

Example 59

N-(2-ethylthiomethyl-4,6-dimethyl-1-propyl-5-sulfamoylaminoindolin-7-yl)-2,2-dimethylpropanamide hydrochloride IR ν (Nujol) cm$^{-1}$; 3146, 3063, 1651, 1504, 1339, 1192, 1159. $^1$H-NMR (DMSO-d$_6$) δ (ppm); 0.81 (3H, t, J=7.2 Hz), 1.20 (3H, t, J=7.3 Hz), 1.25 (9H, s), 1.40-1.70 (2H, m), 2.08 (3H, s), 2.21 (3H, s), 2.50-2.70 (1H, m), 2.61 (2H, q, J=7.3 Hz), 2.70-2.90 (1H, m), 2.90-3.10 (2H, m), 3.20-3.40 (2H, m), 3.40-4.40 (1H, br), 4.00-4.20 (1H, m), 6.50-7.50 (2H, br), 8.30 (1H, br-s), 9.08 (1H, br-s).

Example 60

N-[1-(2-ethylthioethyl)-4,6-dimethyl-5-sulfamoylaminoindolin-7-yl]-2,2-dimethylpropanamide hydrochloride (1) N-[1-(2-Hydroxyethyl)-4,6-dimethyl-5-nitroindolin-7-yl]-2,2-dimethylpropanamide was obtained as crystals (6.21 g) by treating in the same manner as in Example 50 (8) using the compound (8.0 g) obtained in Example 1 (6) and 2-bromoethanol (5.8 mL).

IR ν (Nujol) cm$^{-1}$; 3346, 3233, 1641, 1587, 1506. $^1$H-NMR (DMSO-d$_6$) δ (ppm); 1.21 (9H, s), 1.87 (3H, s), 2.04 (3H, s), 2.89 (2H, t, J=8.8 Hz), 3.30-3.40 (2H, m), 3.50-3.60 (2H, br), 4.65 (2H, t, J=8.8 Hz), 4.79 (1H, t, J=4.9 Hz), 8.85 (1H, s).

(2) N-[1-(2-Acetylthioethyl)-4,6-dimethyl-5-nitroindolin-7-yl]-2,2-dimethylpropanamide was obtained as crystals (6.53 g) by treating in the same manner as in Example 57 (8) using the compound (6.21 g) obtained in (1).

IR ν (Nujol) cm$^{-1}$; 3267, 1703, 1645, 1589, 1506. $^1$H-NMR (CDCl$_3$) δ (ppm); 1.32 (9H, s), 2.05 (3H, s), 2.12 (3H, s), 2.35 (3H, s), 2.94 (2H, t, J=9.0 Hz), 2.97 (2H, t, J=7.8 Hz), 3.35-3.45 (2H, m), 3.63 (2H, t, J=9.0 Hz), 7.07 (1H, s).

(3) N-[1-(2-Mercaptoethyl)-4,6-dimethyl-5-nitroindolin-7-yl]-2,2-dimethylpropanamide was obtained as crystals (5.54 g) by treating in the same manner as in Example 57 (9) using the compound (6.5 g) obtained in (2).

IR ν (Nujol) cm$^{-1}$; 3279, 1645, 1593, 1506. $^1$H-NMR (CDCl$_3$) δ (ppm); 1.36 (9H, s), 1.43 (1H, t, J=7.0 Hz), 2.02 (3H, s), 2.11 (3H, s), 2.67 (2H, q, J=7.0 Hz), 2.94 (2H, t, J=9.0 Hz), 3.50 (2H, t, J=7.3 Hz), 3.57 (2H, t, J=9.0 Hz), 6.97 (1H, s).

(4) N-[1-(2-Ethylthioethyl)-4,6-dimethyl-5-nitroindolin-7-yl]-2,2-dimethylpropanamide was obtained as crystals (1.4 g) by treating in the same manner as in Example 57 (10) using the compound (1.5 g) obtained in (3) and ethyl iodide (0.65 mL).

IR ν (Nujol) cm$^{-1}$; 3277, 1645, 1591, 1510. $^1$H-NMR (CDCl$_3$) δ (ppm); 1.25 (3H, t, J=7.4 Hz), 1.36 (9H, s), 2.03 (3H, s), 2.11 (3H, s), 2.55 (2H, q, J=7.4 Hz), 2.68 (2H, t, J=7.3 Hz), 2.93 (2H, t, J=9.0 Hz), 3.51 (2H, t, J=7.3 Hz), 3.60 (2H, t, J=9.0 Hz), 7.00 (1H, s).

(5) N-[5-(N-tert-Butoxycarbonyl)sulfamoylamino-1-(2-ethylthioethyl)-4,6-dimethyl-7-yl]-2,2-dimethylpropanamide was obtained as crystals (940 mg) by treating in the same manner as in Example 53 (8) using the compound (780 mg) obtained in (4).

IR ν (Nujol) cm$^{-1}$; 3346, 1732, 1653, 1518. $^1$H-NMR (CDCl$_3$) δ (ppm); 1.24 (3H, t, J=7.3 Hz), 1.35 (9H, s), 1.50 (9H, s), 2.06 (3H, s), 2.18 (3H, s), 2.54 (2H, q, J=7.3 Hz), 2.65 (2H, t, J=7.6 Hz), 2.87 (2H, t, J=8.8 Hz), 3.43 (2H, t, J=7.6 Hz), 3.52 (2H, t, J=8.8 Hz), 6.56 (1H, s), 7.08 (1H, br-s), 7.90-8.05 (1H, br).

(6) The title compound was obtained as crystals (680 mg) by treating in the same manner as in Example 6 using the compound (920 mg) obtained in (5).

IR ν (Nujol) cm$^{-1}$; 3558, 3483, 3246, 3163, 1665, 1630, 1504. $^1$H-NMR (DMSO-d$_6$) δ (ppm); 1.16 (3H, t, J=7.3 Hz), 1.27 (9H, s), 2.09 (3H, s), 2.24 (3H, s), 2.53 (2H, q, J=7.3 Hz), 2.70-2.80 (2H, m), 3.06 (2H, br-t), 3.30-3.40 (2H, m), 3.40-4.20 (2H, br), 3.70 (2H, t, J=7.8 Hz), 6.30-7.20 (1H, br), 8.39 (1H, s), 9.05 (1H, s).

Example 61

N-[4,6-dimethyl-1-(2-methylthioethyl)-5-sulfamoylaminoindolin-7-yl]-2,2-dimethylpropanamide hydrochloride (1) N-[4,6-Dimethyl-1-(2-methylthioethyl)-5-nitroindolin-7-yl]-2,2-dimethylpropanamide was obtained as crystals (1.42 g) by treating in the same manner as in Example 57 (10) using the compound (1.5 g) obtained in Example 60 (3) and methyl iodide (0.53 mL).

IR ν (Nujol) cm$^{-1}$; 3280, 1732, 1647, 1593, 1516. $^1$H-NMR (CDCl$_3$) δ (ppm); 1.36 (9H, s), 2.03 (3H, s), 2.11 (3H, s), 2.13 (3H, s), 2.66 (2H, t, J=7.3 Hz), 2.93 (2H, t, J=8.8 Hz), 3.52 (2H, t, J=7.3 Hz), 3.61 (2H, t, J=8.8 Hz), 6.98 (1H, s).

(2) N-[5-(N-tert-Butoxycarbonyl)sulfamoylamino-4,6-dimethyl-1-(2-methylthioethyl)indolin-7-yl]-2,2-dimethylpropanamide was obtained as crystals (1.25 g) by treating in the same manner as in Example 53 (8) using the compound (1.0 g) obtained in (1).

IR ν (Nujol) cm$^{-1}$; 3254, 1728, 1651, 1599, 1508. $^1$H-NMR (CDCl$_3$) δ (ppm); 1.35 (9H, s), 1.50 (9H, s), 2.05 (3H, s), 2.11 (3H, s), 2.17 (3H, s), 2.62 (2H, t, J=7.6 Hz), 2.86 (2H, t, J=8.6 Hz), 3.44 (2H, t, J=7.6 Hz), 3.51 (2H, t, J=8.6 Hz), 6.60 (1H, s), 7.12 (1H, br-s), 7.90-8.15 (1H, br).

(3) The title compound was obtained as crystals (915 mg) by treating in the same manner as in Example 6 using the compound (1.22 g) obtained in (2).

IR ν (Nujol) cm$^{-1}$; 3257, 3143, 1674, 1487. $^1$H-NMR (DMSO-d$_6$) δ (ppm); 1.26 (9H, s), 2.07 (3H, s), 2.09 (3H, s), 2.23 (3H, s), 2.65-2.75 (2H, m), 3.02 (2H, br-t), 3.30-3.40 (2H, m), 3.40-4.20 (2H, br), 3.68 (2H, t, J=8.0 Hz), 6.50-7.00 (1H, br), 8.35 (1H, s), 9.00 (1H, s).

According to Example 53, the compounds of Examples 62 and 63 were synthesized.

Example 62

N-(2-butyl-1,4,6-trimethyl-5-sulfamoylaminoindolin-7-yl)-2,2-dimethylpropanamide hydrochloride IR ν (Nujol) cm$^{-1}$; 3361, 3275, 3138, 1672. $^1$H-NMR (CDCl$_3$) δ (ppm); 0.89 (3H, br-t), 1.26 (9H, s), 1.30-1.40 (4H, m), 1.50-1.65 (1H, br), 1.85-2.00 (1H, br), 2.10 (3H, s), 2.25 (3H, s), 2.70-2.90 (1H, m), 2.83 (3H, s), 3.40-4.00 (3H, m), 3.27 (1H, dd, J=15.6, 7.1 Hz), 6.40-7.20 (1H, br), 8.44 (1H, br-s), 9.24 (1H, br-s).

Example 63

N-(2-butyl-4,6-dimethyl-5-sulfamoylaminoindolin-7-yl)-2,2-dimethylpropanamide

IR ν (Nujol) cm$^{-1}$; 3337, 3271, 1638. $^1$H-NMR (CDCl$_3$) δ (ppm); 0.91 (3H, br-t), 1.35 (9H, s), 1.50-1.70 (6H, m), 2.02 (3H, s), 2.06 (3H, s), 2.59 (1H, dd, J=15.4, 8.3 Hz), 3.12 (1H, dd, J=15.6, 8.6 Hz), 3.15-3.35 (2H, br), 3.75-3.85 (1H, m), 3.90-4.30 (1H, br), 7.07 (1H, br-s).

Then, to clarify the superior characteristic of the compound of the present invention, its inhibitory effects on hepatic ACAT activity, foam cell formation of THP-1 cell-derived macrophages, mouse hepatic lipid secretion amd in vitro LDL peroxidation were determined and its plasma concentration after oral administration were measured as in the following.

Experimental Example 1

Hepatic ACAT Inhibitory Activity

A high cholesterol feed [a feed added with cholesterol (1%), Clea Japan, Inc.] was fed to male Japanese white rabbits weighing 2-2.5 kg at 100 g per day and the rabbits were bred for 4 weeks. The rabbits were killed by bleeding under anesthesia and liver was removed. The liver was homogenated, and the homogenate was centrifuged at 4° C. and 10,000 rpm for 15 min. The obtained supernatant was further centrifuged at 4° C. and 41,000 rpm for 60 minutes to give microsomal fractions. The microsomal suspension as an enzyme sample, dimethyl sulfoxide (DMSO, 5 μl) or a test compound dissolved in DMSO (test compound solution 3 μl), and reaction substrate [1-$^{14}$C]-oleoyl CoA were added to 0.15 M phosphate buffer to the total amount of 300 μl. After incubation at 37° C. for 20 minutes, a chloroform-methanol mixture was added to stop the reaction. Water was added thereto and mixed, and the chloroform layer was separated. The solvent was evaporated to dryness, and the residue was redissolved in n-hexane. The mixture was subjected to thin layer chromatography using a silica gel plate. The spots of cholesteryl oleate on the silica gel plate were scraped, and quantitatively assayed on lo a liquid scintillation counter. The hepatic ACAT inhibitory activity of the test compound was expressed as a proportion (%) of inhibition of cholesteryl oleate, namely, the proportion of inhibition of cholesteryl oleate production as compared to control, the results of which are shown in Table 1.

TABLE 1

| Test compound | Hepatic ACAT inhibitory ratio (%) (Concentration: $10^{-6}$ M) |
|---|---|
| Example 1 | 97.4 |
| Example 2 | 94.8 |
| Example 3 | 89.3 |
| Example 4 | 75.8 |
| Example 6 | 97.4 |
| Example 7 | 95.7 |
| Example 8 | 96.3 |
| Example 10 | 87.3 |
| Example 11 | 97.4 |
| Example 12 | 96.4 |
| Example 13 | 96.9 |
| Example 14 | 90.6 |
| Example 15 | 96.1 |
| Example 16 | 71.9 |
| Example 17 | 86.4 |
| Example 18 | 96.7 |
| Example 19 | 93.4 |
| Example 20 | 95.7 |
| Example 21 | 92.7 |
| Example 22 | 97.9 |
| Example 23 | 96.2 |
| Example 24 | 95.7 |
| Example 25 | 94.3 |
| Example 26 | 95.4 |
| Example 27 | 78.6 |
| Example 29 | 79.5 |
| Example 39 | 97.0 |
| Example 40 | 97.8 |
| Example 41 | 97.3 |
| Example 43 | 90.9 |
| Example 45 | 97.3 |
| Example 46 | 89.2 |
| Example 50 | 86.2 |
| Example 57 | 94.2 |
| Example 59 | 98.1 |
| Example 60 | 97.2 |
| Example 61 | 95.4 |

Experimental Example 2

THP-1 Cell-derived Macrophage Foam Cell Formation Suppressing Effect (Cholesterol Ester Accumulation Inhibitory Effect)

THP-1 (Dainippon Pharmaceutical Co., Ltd.) cells were passage cultured in RPMI-1640 medium supplemented with 10% fetal bovine serum (FBS), and the cells of passages 6-13 after purchase were used. The cells were suspended in FBS-containing RPMI-1640 medium to give a suspension having a concentration of $4\times10^5$ cells/mL. The cell suspension was inoculated to a 12 well microplate by 1 mL, and treated with phorbol 12-myristate 13-acetate (PMA, 200 nM) as a differentiation inducing agent into macrophage. Then acetyl LDL 400 μg/mL prepared separately from plasma-derived LDL of genetically hyperlipidemia rabbit (KHC rabbit, Japan Laboratory Animals, Inc.) was added. In addition, a test compound dissolved in DMSO and diluted with FBS-containing RPMI-1640 medium or a control solvent was added. After culture in a carbon dioxide incubator for 3 days, the cells were washed with phosphate buffered physiological saline (pH 7.0), and the lipid was extracted with n-hexane/isopropanol (3:2). The cells were dissolved in 1M-NaOH and the protein amount was measured. The free cholesterol and cholesterol ester in a lipid extraction sample was measured by the method of Kunitomo et al. (1983). The cholesterol ester was compared between the control cell and the test compound-treated cells, and the cholesterol ester accumulation inhibitory rate of the test compound was calculated. The results are shown in Table 2.

TABLE 2

| Test compound | foam cell formation inhibitory rate (%) (Concentration: $10^{-6}$ M) |
|---|---|
| Example 2 | 92.1 |
| Example 6 | 91.2 |
| Example 7 | 90.9 |
| Example 8 | 89.2 |
| Example 9 | 70.9 |
| Example 11 | 95.2 |
| Example 12 | 77.3 |
| Example 13 | 95.5 |
| Example 14 | 59.0 |
| Example 15 | 84.3 |
| Example 18 | 93.0 |
| Example 19 | 73.3 |
| Example 20 | 74.7 |
| Example 21 | 77.1 |
| Example 22 | 87.7 |
| Example 23 | 90.5 |
| Example 24 | 90.5 |
| Example 25 | 89.4 |
| Example 26 | 75.3 |
| Example 39 | 78.7 |
| Example 40 | 80.7 |
| Example 41 | 76.5 |
| Example 43 | 58.7 |
| Example 45 | 86.2 |
| Example 46 | 59.1 |
| Example 50 | 73.6 |
| Example 51 | 86.0 |
| Example 53 | 70.0 |
| Example 54 | 64.5 |
| Example 57 | 79.9 |
| Example 59 | 92.1 |

Experimental Example 3

Mouse Hepatic Lipid Secretion Inhibitory Effect (Triton WR-1339 Method)

About 5 week-old male Slc:ICR mice (Japan SLC) were fed only in the daytime (9:00-18:00) and preliminarily bred for one week. During this period, free access to tap water was allowed during the nighttime, too. The mice were divided into a control group and a test compound group at 6 mice per group, such that the average and standard deviation of the body weight became almost the same. The blood (ca 80 μL) was drawn from the orbital venous plexus using a glass capillary under anesthesia, and at 30 min after blood drawing, a test compound suspended in 5% gum arabic solution in advance was orally administered at a dose of 10 mg/kg. At 30 min after the administration, Triton WR-1339 60 mg/mL solution prepared with physiological saline in advance was administered to the tail vein at a dose of 5 mL/kg. At 3 hr after the Triton WR-1339 administration, the blood was drawn again from the orbital venous plexus. Plasma was separated from the drawn blood, and plasma TC was measured using a commercially available measurement kit (Wako Pure Chemical Industries, Ltd.). Changes in blood-concentration in 3 hr after Triton WR-1339 administration were calculated and taken as the rate of cholesterol secretion from the liver. The rate of secretion was compared between the control group and the test compound group and the secretion inhibitory rate of the test compound was calculated. The results are shown in Table 3.

TABLE 3

| Test compound | Cholesterol secretion inhibitory rate (%) 10 mg/kg/day |
|---|---|
| Example 2 | 39.0 |
| Example 11 | 40.7 |
| Example 12 | 49.8 |
| Example 13 | 53.9 |
| Example 14 | 41.7 |
| Example 15 | 42.0 |
| Example 16 | 40.9 |
| Example 17 | 44.4 |
| Example 18 | 41.4 |
| Example 22 | 39.9 |
| Example 39 | 57.7 |
| Example 41 | 58.5 |
| Example 45 | 54.8 |

Experimental Example 4

In Vitro LDL Peroxidation Inhibitory Effect

The blood was drawn from the auricular artery of KHC rabbits weighing about 3 kg and LDL was separated by a conventional method. A solution (5 µL) of test compound in DMSO or DMSO was added (final concentration $10^{-5}$ M) to LDL suspension (0.5 mg protein/mL, 0.5 mL), aqueous copper sulfate solution (5 µL, final concentration 5 µM) was added, and the mixture was incubated at 37° C. for 1 hr. After the completion of the incubation, EDTA·2Na solution (5 µL, final concentration 1 mM) was added, and lipoperoxide concentration in the-sample was measured by the Yagi's method. To be specific, lipoperoxide in the sample was color developed by the thiobarbituric acid method, measured as malondialdehyde and the activity of the test compound was shown by malondialdehyde production inhibitory rate (%) [to what level the production of malondialdehyde was inhibited as compared to control]. The results are shown in Table 4.

TABLE 4

| Test compound | LDL peroxidation inhibitory ratio (%) (Concentration: $10^{-5}$ M) |
|---|---|
| Example 2 | 81.9 |
| Example 11 | 77.2 |
| Example 12 | 68.5 |
| Example 13 | 77.1 |
| Example 14 | 68.8 |
| Example 15 | 69.5 |
| Example 16 | 59.5 |
| Example 22 | 79.0 |
| Probucol | 33.8 |

Experimental Example 5

Oral Administration

A test compound (10 mg/kg) suspended in 5% gum arabic solution was forcibly administered orally to SD male rats weighing 200-250 g. At 0.5, 1, 3, 5 and 8 hours after administration, blood was taken without anesthesia and heparinized plasma was separated by conventional method. The concentration of the test compound in the plasma was determined by high performance liquid chromatography, the results of which are shown in Table 5.

TABLE 5

| Test compound | Maximum concentration in blood (µg/mL) |
|---|---|
| Example 11 | 1.98 |
| Example 12 | 3.05 |
| Example 13 | 1.36 |
| Example 14 | 2.30 |
| Example 15 | 1.68 |
| Example 16 | 2.90 |
| Example 22 | 1.12 |
| Example 41 | 2.03 |
| Example 53 | 1.31 |

INDUSTRIAL APPLICABILITY

The compound of the present invention (I) and a pharmaceutically acceptable salt thereof show superior ACAT inhibitory effect and lipoperoxidation inhibitory effect in mammals (human, bovine, horse, dog, cat, rabbit, rat, mouse, hamster etc.), and are useful as an ACAT inhibitor and a lipoperoxidation inhibitor. In other words, they are useful for the prophylaxis or treatment of arteriosclerosis, hyperlipidemia, arteriosclerotic lesion in diabetes, ischemic diseases of brain and heart and the like, and the like.

This application is based on Japanese Patent Application No. 2002-208878, which was filed in Japan, and the contents of which are hereby incorporated by reference.

The invention claimed is:

1. An indoline compound represented by the formula (I)

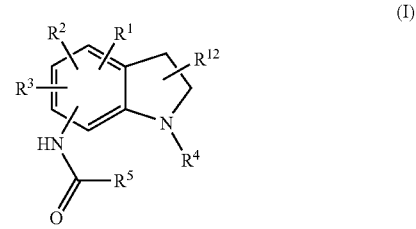

(I)

wherein
R$^1$ and R$^3$
are the same or different and each is hydrogen atom, lower alkyl group or lower alkoxy group,
R$^2$ is —NHSO$_2$R$^6$ [R$^6$ is alkyl group, aryl group or —NHR$^7$ (R$^7$ is hydrogen atom, —COR$^{13}$ (R$^{13}$ is hydrogen atom or lower alkyl group) or lower alkoxycarbonyl group)], —NHCONH$_2$ or lower alkyl group substituted by —NHSO$_2$R$^6$ [R$^6$ is alkyl group, aryl group or —NHR$^7$ (R$^7$ is hydrogen atom, —COR$^{13}$ (R$^{13}$ is hydrogen atom or lower alkyl group) or lower alkoxycarbonyl group)], R⁴ is alkyl group optionally substituted by hydroxy group, —COR¹³ (R¹³ is hydrogen atom or lower alkyl group), lower alkenyl group, lower alkoxy lower alkyl group, lower alkylthio lower alkyl group, cycloalkyl group or cycloalkylalkyl group, R⁵ is alkyl group, cycloalkyl group or aryl group, R⁶ is hydrogen atom, lower alkyl group, lower alkoxy lower alkyl group or lower alkylthio lower alkyl group, or a pharmaceutically acceptable salt thereof.

2. The indoline compound of claim 1, wherein, in the formula (I),

R¹ and R³ are the same or different and each is hydrogen atom, lower alkyl group or lower alkoxy group, R² is —NHSO₂R⁶ [R⁶ is alkyl group, aryl group or —NHR⁷ (R⁷ is hydrogen atom, —COR¹³ (R¹³ is hydrogen atom or lower alkyl group) or lower alkoxycarbonyl group)], —NHCONH₂ or lower alkyl group substituted by —NHSO₂R⁶ [R⁶ is alkyl group, aryl group or —NHR⁷ (R⁷ is hydrogen atom, —COR¹³ (R¹³ is hydrogen atom or lower alkyl group) or lower alkoxycarbonyl group)], R⁴ is alkyl group, cycloalkyl group or cycloalkylalkyl group, R⁵ is alkyl group, cycloalkyl group or aryl group, and R¹² is hydrogen atom, or a pharmaceutically acceptable salt thereof.

3. The indoline compound of claim 1, wherein, in the formula (I), R² is —NHSO₂R⁶ [R⁶ is alkyl group or —NHR⁷ (R⁷ is hydrogen atom)], R⁴ is alkyl group optionally substituted by hydroxy group, —COR¹³ (R¹³ is hydrogen atom or lower alkyl group), lower alkenyl group, lower alkoxy lower alkyl group or lower alkylthio lower alkyl group, R⁵ is alkyl group, and R¹² is hydrogen atom, lower alkyl group, lower alkoxy lower alkyl group or lower alkylthio lower alkyl group, or a pharmaceutically acceptable salt thereof.

4. The indoline compound of claim 2, wherein, in the formula (I), R² is —NHSO₂R⁶ [R⁶ is alkyl group or —NHR⁷ (R⁷ is hydrogen atom)]or —NHCONH₂, or a pharmaceutically acceptable salt thereof.

5. The indoline compound of claim 2, wherein, in the formula (I), R² or —NHCOR⁵ is bonded to the 5-position of indoline, and the other is bonded to the 7-position of indoline, or a pharmaceutically acceptable salt thereof.

6. The indoline compound of claim 3, wherein, in the formula (I), R² is bonded to the 5-position of indoline, and —NHCOR⁵ is bonded to the 7-position of indoline, or a pharmaceutically acceptable salt thereof.

7. The indoline compound of claim 4, wherein, in the formula (I), R² is bonded to the 5-position of indoline, and —NHCOR⁵ is bonded to the 7-position of indoline, or a pharmaceutically acceptable salt thereof.

8. The indoline compound of claim 6, wherein, in the formula (I), R⁴ is lower alkoxy lower alkyl group or lower alkylthio lower alkyl group, and R¹² is hydrogen atom or lower alkyl group, or a pharmaceutically acceptable salt thereof.

9. The indoline compound of claim 8, wherein, in the formula (I), R¹ and R³ are lower alkyl groups, or a pharmaceutically acceptable salt thereof.

10. The indoline compound of claim 6, wherein, in the formula (I), R¹² is bonded to the 2-position of indoline, or a pharmaceutically acceptable salt thereof.

11. The indoline compound of claim 10, wherein, in the formula (I), R⁴ is alkyl group, R¹² is lower alkoxy lower alkyl group or lower alkylthio lower alkyl group, or a pharmaceutically acceptable salt thereof.

12. The indoline compound of claim 11, wherein, in the formula (I), R¹ and R³ are lower alkyl groups, or a pharmaceutically acceptable salt thereof.

13. The indoline compound of claim 7, wherein, in the formula (I), R¹ and R³ are lower alkyl groups, and R⁵ is alkyl group, or a pharmaceutically acceptable salt thereof.

14. The indoline compound of claim 13, wherein, in the formula (I), R² is —NHSO₂R⁶ (R⁶ is alkyl group), or a pharmaceutically acceptable salt thereof.

15. The indoline compound of claim 13, wherein, in the formula (I), R² is —NHSO₂R⁶ [R⁶ is —NHR⁷ (R⁷ is hydrogen atom)], or a pharmaceutically acceptable salt thereof.

16. The indoline compound of claim 13, wherein, in the formula (I), R² is —NHCONH₂, or a pharmaceutically acceptable salt thereof.

17. The indoline compound of claim 2, wherein the compound of the formula (I) is any of the following (1)-(5), or a pharmaceutically acceptable salt thereof:
 (1) N-(5-methanesulfonylamino-4,6-dimethyl-1-propylindolin-7-yl)-2,2-dimethylpropanamide,
 (2) N-[5-methanesulfonylamino-4,6-dimethyl-1-(2-methylpropyl)indolin-7-yl]-2,2-dimethylpropanamide,
 (3) N-(1-butyl-5-methanesulfonylamino-4,6-dimethylindolin-7-yl)-2,2-dimethylpropanamide,
 (4) N-[5-methanesulfonylamino-4,6-dimethyl-1-(3-methylbutyl)indolin-7-yl]-2,2-dimethylpropanamide,
 (5) N-(5-methanesulfonylamino-4,6-dimethyl-1-pentylindolin-7-yl)-2,2-dimethylpropanamide.

18. The indoline compound of claim 2, wherein the compound of the formula (I) is the following (1) or (2), or a pharmaceutically acceptable salt thereof:
 (1) N-(5-methanesulfonylamino-4,6-dimethyl-1-octylindolin-7-yl)-2,2-dimethylpropanamide,
 (2) N-(1-hexyl-5-methanesulfonylamino-4,6-dimethylindolin-7-yl)-2,2-dimethylpropanamide.

19. The indoline compound of claim 2, wherein the compound of the formula (I) is the following (1) or (2), or a pharmaceutically acceptable salt thereof:
 (1) N-(1-ethyl-5-methanesulfonylamino-4,6-dimethylindolin-7-yl)-2,2-dimethylpropanamide,
 (2) N-(5-methanesulfonylamino-1,4,6-trimethylindolin-7-yl)-2,2-dimethylpropanamide.

20. The indoline compound of claim 2, wherein the compound of the formula (I) is any of the following (1)-(6), or a pharmaceutically acceptable salt thereof:
 (1) N-(4,6-dimethyl-1-octyl-5-sulfamoylaminoindolin-7-yl)-2,2-dimethylpropanamide,
 (2) N-(4,6-dimethyl-1-propyl-5-sulfamoylaminoindolin-7-yl)-2,2-dimethylpropanamide,
 (3) N-(4,6-dimethyl-1-pentyl-5-sulfamoylaminoindolin-7-yl)-2,2-dimethylpropanamide,
 (4) N-[4,6-dimethyl-1-(2-methylpropyl)-5-sulfamoylaminoindolin-7-yl]-2,2-dimethylpropanamide,
 (5) N-(1-butyl-4,6-dimethyl-5-sulfamoylaminoindolin-7-yl)-2,2-dimethylpropanamide,
 (6) N-[4,6-dimethyl-1-(3-methylbutyl)-5-sulfamoylaminoindolin-7-yl]-2,2-dimethylpropanamide.

21. The indoline compound of claim 2, wherein the compound of the formula (I) is N-(7-methanesulfonylamino-1,4,6-trimethylindolin-5-yl)-2,2-dimethylundecanamide, or a pharmaceutically acceptable salt thereof.

22. The indoline compound of claim 2, wherein the compound of the formula (I) is any of the following (1)-(4), or a pharmaceutically acceptable salt thereof:
- (1) N-(5-methanesulfonylaminomethyl-4,6-dimethyl-1-octylindolin-7-yl)-2,2-dimethylpropanamide,
- (2) N-(4,6-dimethyl-1-octyl-5-ureidoindolin-7-yl)-2,2-dimethylpropanamide,
- (3) N-[5-(N-acetylsulfamoylamino)-4,6-dimethyl-1-octylindolin-7-yl]-2,2-dimethylpropanamide,
- (4) N-[5-(N-methoxycarbonylsulfamoylamino)-4,6-dimethyl-1-octylindolin-7-yl]-2,2-dimethylpropanamide.

23. The indoline compound of claim 9, wherein, in the formula (I), $R^2$ is —$NHSO_2R^6$ ($R^6$ is alkyl group), or a pharmaceutically acceptable salt thereof.

24. The indoline compound of claim 9, wherein, in the formula (I), $R^2$ is —$NHSO_2R^6$ [$R^6$ is —$NHR^7$ ($R^7$ is hydrogen atom)], or a pharmaceutically acceptable salt thereof.

25. The indoline compound of claim 2, wherein the compound of the formula (I) is any of the following (1)-(6), or a pharmaceutically acceptable salt thereof:
- (1) N-(1-isopropyl-5-methanesulfonylamino-4,6-dimethylindoline 7-yl)-2,2-dimethylpropanamide,
- (2) N-[1-(2,2-dimethylpropyl)-5-methanesulfonylamino-4,6-dimethylindolin-7-yl]-2,2-dimethylpropanamide,
- (3) N-(1-cyclobutylmethyl-5-methanesulfonylamino-4,6-dimethylindolin-7-yl)-2,2-dimethylpropanamide,
- (4) N-(1-cyclopentyl-5-methanesulfonylamino-4,6-dimethylindolin-7-yl)-2,2-dimethylpropanamide,
- (5) N-(1-cyclopentyl-4,6-dimethyl-5-sulfamoylaminoindolin-7-yl)-2,2-dimethylpropanamide,
- (6) N-(1-cyclopropylmethyl-5-methanesulfonylamino-4,6-dimethylindolin-7-yl)-2,2-dimethylpropanamide.

26. The indoline compound of claim 3, wherein the compound of the formula (I) is N-[5-methanesulfonylamino-4,6-dimethyl-1-(3-methyl-2-butenyl)indolin-7-yl]-2,2-dimethylpropanamide, or a pharmaceutically acceptable salt thereof.

27. The indoline compound of claim 3, wherein the compound of the formula (I) any of the following (1)-(6), or a pharmaceutically acceptable salt thereof:
- (1) N-[1-(2-ethoxyethyl)-4,6-dimethyl-5-sulfamoylaminoindolin-7-yl]-2,2-dimethylpropanamide,
- (2) N-[1-(2-ethoxyethyl)-2,4,6-trimethyl-5-sulfamoylaminoindolin-7-yl]-2,2-dimethylpropanamide,
- (3) N-[1-(2-methoxyethyl)-4,6-dimethyl-5-sulfamoylaminoindolin-7-yl]-2,2-dimethylpropanamide,
- (4) N-[1-(2-methoxyethyl)-2,4,6-trimethyl-5-sulfamoylaminoindolin-7-yl]-2,2-dimethylpropanamide,
- (5) N-[1-(2-ethylthioethyl)-4,6-dimethyl-5-sulfamoylaminoindolin-7-yl]-2,2-dimethylpropanamide hydrochloride,
- (6) N-[4,6-dimethyl-1-(methylthioethyl)-5-sulfamoylaminoindolin-7-yl]-2,2-dimethylpropanamide hydrochloride.

28. The indoline compound of claim 3, wherein the compound of the formula (I) is any of the following (1)-(4), or a pharmaceutically acceptable salt thereof:
- (1) N-(2-methoxymethyl-4,6-dimethyl-1-propyl-5-sulfamoylaminoindolin-7-yl)-2,2-dimethylpropanamide,
- (2) N-(2-ethoxymethyl-4,6-dimethyl-1-propyl-5-sulfamoylaminoindolin-7-yl)-2,2-dimethylpropanamide,
- (3) N-(2-methylthiomethyl-4,6-dimethyl-1-propyl-5-sulfamoylaminoindolin-7-yl)-2,2-dimethylpropanamide,
- (4) N-(2-ethylthiomethyl-4,6-dimethyl-1-propyl-5-sulfamoylaminoindolin-7-yl)-2,2-dimethylpropanamide.

29. The indoline compound of claim 3, wherein the compound of the formula (I) is the following (1) or (2), or a pharmaceutically acceptable salt thereof:
- (1) N-[1-(2-ethoxyethyl)-5-methanesulfonylamino-4,6-dimethylindolin-7-yl]-2,2-dimethylpropanamide,
- (2) N-[1-(2-methoxyethyl)-5-methanesulfonylamino-4,6-dimethylindolin-7-yl]-2,2-dimethylpropanamide.

30. A pharmaceutical composition comprising the indoline compound of claim 1, or a pharmaceutically acceptable salt thereof.

31. An acyl-coenzyme A: cholesterol acyl transferase inhibitor comprising the indoline compound of claim 1, or a pharmaceutically acceptable salt thereof.

32. A lipoperoxidation inhibitor comprising the indoline compound of claim 1, or a pharmaceutically acceptable salt thereof.

33. The indoline compound of claim 12, wherein, in the formula (I), $R^2$ is —$NHSO_2R^6$ ($R^6$ is alkyl group), or a pharmaceutically acceptable salt thereof.

34. The indoline compound of claim 12, wherein, in the formula (I), $R^2$ is —$NHSO_2R^6$ [$R^6$ is —$NHR^7$ ($R^7$ is hydrogen atom)], or a pharmaceutically acceptable salt thereof.

* * * * *